United States Patent
Li et al.

(10) Patent No.: US 10,465,002 B2
(45) Date of Patent: Nov. 5, 2019

(54) NUCLEIC ACIDS ENCODING ANTIBODIES TO KALLIDIN AND DES-ARG$_{10}$-KALLIDIN AND HOST CELLS COMPRISING THE SAME

(71) Applicant: Sanofi, Paris (FR)

(72) Inventors: Han Li, Yardley, PA (US); Dorothea Kominos, Millington, NJ (US); Jie Zhang, Cambridge, MA (US); Alla Pritsker, Cambridge, MA (US); Matthew Davison, Cambridge, MA (US); Nicolas Baurin, Arpajon (FR); Govindan Subramanian, Belle Mead, NJ (US); Xin Chen, Edison, NJ (US)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/844,883

(22) Filed: Dec. 18, 2017

(65) Prior Publication Data
US 2018/0222967 A1   Aug. 9, 2018

Related U.S. Application Data

(62) Division of application No. 15/163,883, filed on May 25, 2016, now Pat. No. 9,879,079, which is a division of application No. 14/382,798, filed as application No. PCT/US2013/031836 on Mar. 15, 2013, now Pat. No. 9,376,494.

(60) Provisional application No. 61/616,845, filed on Mar. 28, 2012.

(30) Foreign Application Priority Data

Feb. 4, 2013 (FR) .................... 13 50953

(51) Int. Cl.
| | | |
|---|---|---|
| *C07H 21/04* | (2006.01) |
| *C12N 15/11* | (2006.01) |
| *C12N 15/63* | (2006.01) |
| *A61K 39/395* | (2006.01) |
| *C07K 16/22* | (2006.01) |
| *C07K 16/18* | (2006.01) |
| *C07K 16/26* | (2006.01) |
| *A61K 47/51* | (2017.01) |
| *A61K 47/68* | (2017.01) |
| *A61P 29/00* | (2006.01) |
| *C07K 7/06* | (2006.01) |
| *C07K 7/18* | (2006.01) |
| *A61K 39/00* | (2006.01) |

(52) U.S. Cl.
CPC .......... *C07K 16/18* (2013.01); *A61K 39/3955* (2013.01); *A61K 47/51* (2017.08); *A61K 47/6843* (2017.08); *C07H 21/04* (2013.01); *C07K 16/22* (2013.01); *C07K 16/26* (2013.01); *C12N 15/11* (2013.01); *C12N 15/63* (2013.01); *A61K 2039/505* (2013.01); *A61P 29/00* (2018.01); *C07K 7/06* (2013.01); *C07K 7/18* (2013.01); *C07K 2299/00* (2013.01); *C07K 2317/24* (2013.01); *C07K 2317/33* (2013.01); *C07K 2317/34* (2013.01); *C07K 2317/56* (2013.01); *C07K 2317/76* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

| JP | 2008-543810 A | 12/2008 |
|---|---|---|
| WO | 2006/134125 A9 | 5/2007 |

OTHER PUBLICATIONS

Bedi et al. (1985) "Monoclonal antibodies to bradykinin inhibit smooth muscle contractile action of bradykinin," Biochimica et Biophysica Acta (BBA)-General Subjects. 842(1):90-99.
Benjamini et al. (1991) Immunology: A Short Course. 2nd Ed. p. 40.
Campbell (1984) "General properties and applications of monoclonal antibodies," Ch. 1 In; Laboratory Techniques in Biochemistry and Molecular Biology. vol. 13. pp. 1-32.
Carretero et al. (1976) "Measurement of urinary kallikrein activity by kinin radioimmunoassay," Biochemical Pharmacology. 25(20):2265-2270.
Casset et al. (2003) "A peptide mimetic of an anti-CD4 monoclonal antibody by rational design," Biochemical and Biophysical Research Communications. 307:198-205.
Chen et al. (1999) "Selection and analysis of an optimized anti-VEGF antibody: crystal structure of an affinity-matured Fab in complex with antigen," Journal of Molecular Biology. 293:865-881.
Debnath et al. (2010) "immunoassays," Ch. 11 In; Molecular Diagnostics: Promises and Possibilities. pp. 171-180.

(Continued)

*Primary Examiner* — Zachary C Howard
(74) *Attorney, Agent, or Firm* — Lathrop Gage LLP; James H. Velema, Esq.

(57) ABSTRACT

The invention provides antibodies that specifically bind to Kallidin or des-Arg10-Kallidin. The invention also provides pharmaceutical compositions, as well as nucleic acids encoding anti-Kallidin or des-Arg10-Kallidin antibodies, recombinant expression vectors and host cells for making such antibodies, or fragments thereof. Methods of using antibodies of the invention to modulate Kallidin or des-Arg10-Kallidin activity or detect Kallidin or des-Arg10-Kallidin, either in vitro or in vivo, are also provided by the invention. The invention further provides methods of making antibodies that specifically bind to des-Arg$_9$-Bradykinin and des-Arg$_{10}$-Kallidin-like peptide.

15 Claims, 17 Drawing Sheets

Specification includes a Sequence Listing.

(56) References Cited

OTHER PUBLICATIONS

Duncan et al. (2000) "Kinins in humans," Am. J. Physiol. Regul. Integr. Physiol. 278:R897-R904.

Fernandez-Sanchez (2009) "Mouse monoclonal antibodies to pneumococcal C-polysaccharide backbone show restricted usage of VH-DH-JH gene segments and share the same kappa chain," Immunol. Lett. 123(2):125-131.

Geppetti et al. (1991) "Kallidin applied to the human nasal mucosa produces algesic response not blocked by capsaicin desensitization," Regulatory Peptides. 33(3):321-329.

Haaseman et al. (1991) "Anti-Idiotypic Antibodies Bearing the Internal Image of a Bradykinin Epitope, Production, characterization, and interaction with the kinin receptor," J. Immunol. 147:3382-3892.

Hilgenfeldt et al. (1995) "Strategy of measuring bradykinin and kallidin and their concentration in plasma and urine," Analytical Biochemistry. 228(1):35-41.

Holm et al. (2007) "Functional mapping and single chain construction of the anti-cytokeratin 8 monoclonal antibody TS1," Molecular Immunology. 44:1075-1084.

MacCallum et al. (1996) "Antibody-antigen interactions: contact analysis and binding site topography," Journal of Molecular Biology. 262:732-745.

Odya et al. (1990) "Enzyme-Linked Immunosorbent Assays for Kinins Using High-Affinity Monoclonal Kinin Antibodies," Biochem. Pharma. 40(2):235-251.

Odya et al. (1993) "Immunoassays for des-Arg9-Bradykinin," J. Immunoassay. 14(4):227-240.

Pascalis et al. (2002) "Grafting of 'abbreviated' complementarity-determining regions containing specificity-determining residues essential for ligand contact to engineer a less immunogenic humanized monoclonal antibody," Journal of Immunology. 169:3076-3084.

Rudikoff et al. (1982) "Single amino acid substitution altering antigen-binding specificity," Proc. Natl. Acad. Sci. USA. 79:1979-1983.

Vajdos et al. (2002) "Comprehensive functional maps of the antigen-binding site of an anti-ErbB2 antibody obtained with shotgun scanning mutagenesis," Journal of Molecular Biology. 320:415-428.

Wu et al. (1999) "Humanization of a murine monoclonal antibody by simultaneous optimization of framework and CDR residues," Journal of Molecular Biology. 294:151-162.

International Search Report and Written Opinion of the International Searching Authority for International Application No. PCT/US2013/031836, dated Jun. 5, 2013.

Heavy Chain Alignment

Parental:    EIQLQQSGPELVKPGTSVKVSCKASGYSFTDYNIYWKQSHGKSLEWIGYFDPYNGNTGY
             +IQL QSG E+ KPG SVKVSCKASGYSFTDYNIYWV+Q+ G+ LEWIGYFDPYNGNTGY
Humanized:   QIQLVQSGAEVKKPGASVKVSCKASGYSFTDYNIYWVRQAPGQGLEWIGYFDPYNGNTGY Parental:    NQKFRGKATLTVDKSSSTAFMHLSSLTSDDSAVYYCANYYRYDDHAMDYWGQTSVTVSS
             NQKFRG+ ATLTVDKS+STA+M L SL SDD+AVYYCANYYRYDDHAMDYWGQGT VTVSS
Humanized:   NQKFRGRATLTVDKSTSTAYMELRSLRSDDTAVYYCANYYRYDDHAMDYWGQGTLVTVSS Light Chain Alignment Parental:    DIVMSQSPSSLAVSVGEKVTMSCKSSQSLLYSSNQKNYLAWYQQKPGQSPKPLIYWASTR
             DIVM+QSP SLAVS+GE+ T++CKSSQSLLYSSNQKNYLAWYQQKPGQ PKPLIYWASTR
Humanized:   DIVMTQSPDSLAVSLGERATINCKSSQSLLYSSNQKNYLAWYQQKPGQPPKPLIYWASTR Parental:    ESGVPDRFTGSGSGTDFTLTISSVKAEDLAIYYCQQYYSYPWTFGGGTKLEIK
             ESGVPDRF+GSGSGTDFTLTISS++AED+A+YYCQQYYSYPWTFG GTK+EIK
Humanized:   ESGVPDRFSGSGSGTDFTLTISSLQAEDVAVYYCQQYYSYPWTFGQGTKVEIK

```
              10        20        30        40        50        60
F151LC DIVMSQSPSSLAVSVGEKVTMSCKSSQSLLYSSNQKNYLAWYQQKPGQSPKPLIYWASTR
       ::       :::::::         :::::                 :::  :::
VK1    DIQMTQSPSSLSASVGDRVTITCRASQSI------SSYLNWYQQKPGKAPKLLIYAASSL
              10        20          30        40        50

70        80        90       100       110
F151LC ESGVPDRKFTGSGSGTDFTLTISSVKAEDLAIYYCQQYYSYPWTFGGGTKLE    (SEQ ID NO: 111)
       :::::: :::::::::::::::::: :: ::::::::  : :: :::: ::
VK1    QSGVPSRFSGSGSGTDFTLTISSLQPEDLATYYCQQSYSTPPTFGQGTKVE     (SEQ ID NO: 112)
              60        70        80        90       100
```

B.

```
              10        20        30        40        50        60
F151HC EIQLQQSGPELVKPGTSVKVSCKASGYSFTDYNIYWVKQSHGKSLEWIGYFDPYNGNIGY
       : :: ::: :: ::: :::::::::: ::    ::::: :: :::: : ::  ::::::
VH1b   QVQLVQSGAEVKKPGASVKVSCKASGYTFTSYYMHWVRQAPGQGLEWMGWINPNSGGTNY
              10        20        30        40        50        60

70        80        90       100       110
F151HC NQKFRGKATLTVDKSSSTAFMHLSSLTSDDSAVYYCANY-YRYD--DHAMDYWGQGTSVT
        :::    : : ::::::: ::::::  :::::::: :  ::     :::::::::::
VH1b   AQKFQGRVTMTRDKSSSTAYMELSSLRSEDTAVYYCARWGYDYDVFYYAMDYWGQGTLVT
              70        80        90       100       110       120

120
F151HC VSS    (SEQ ID NO: 113)
       :::
VH1b   VSS    (SEQ ID NO: 114)
```

mF151-LC:              DIVMSQSPSSLAVSVGEKVTMSCKSSQSLLYSSNQKNYLAWYQQKPGQSPKPLIYWASTRES
Z46615-1-V-X67858-1-J: DIVMTQSPDSLAVSLGERATINCKSSQSVLYSSNNKNYLAWYQQKPGQPPKLLIYWASTRES

GVPDRFTGSGSGTDFTLTISSVKAEDLAIYYCQQYYSYPWTFGGGTKLEIK (SEQ ID NO:26)
GVPDRFSGSGSGTDFTLTISSLQAEDVAVYYCQQYYSTPWTFGQGTKVEIK (SEQ ID NO:115)

B.

mF151-HC:                  EIQLQQSGPELVKPGTSVKVSCKASGYSFTDYNIYWVKQSHGKSLEWIGY
Z12316-1-VX97051-4-D-X97051-5-J: QVQLVQSGAEVKKPGASVKVSCKASGYTFTSYGISWVRQAPGQGLEWMGW

FDPYNGNTGYNQKFRGKATLTVDKSSSTAFMHLSSLTSDDSAVYYCANYYRYDDHAMDYWGQGTSVTVSS (SEQ ID NO:19)
ISAYNGNTNYAQKLQGRVTMTTDTSTSTAYMELRSLRSDDTAVYYCAREYSSSSDAFDIWGQGTMVTVSS (SEQ ID NO:116)

Figure 16

NUCLEIC ACIDS ENCODING ANTIBODIES TO KALLIDIN AND DES-ARG$_{10}$-KALLIDIN AND HOST CELLS COMPRISING THE SAME

RELATED APPLICATIONS

This application is a division of U.S. patent application Ser. No. 15/163,883, filed May 25, 2016, now U.S. Pat. No. 9,879,079, which is a division of U.S. patent application Ser. No. 14/382,798, filed Sep. 4, 2014, now U.S. Pat. No. 9,376,494, which is a 35 U.S.C. § 371 filing of International Patent Application No. PCT/US13/31836, filed on Mar. 15, 2013, which claims priority to U.S. Provisional Patent Application Ser. No. 61/616,845, filed Mar. 28, 2012, and French Patent Application Number 1350953, filed Feb. 4, 2013. The contents of these applications are each hereby incorporated by reference in their entireties.

BACKGROUND OF THE INVENTION

The bradykinin B1 receptor has been implicated in pathogenesis of inflammatory disease and chronic pain. By modulating tissue inflammation and renal fibrosis, the B1 receptor has also been associated with pathogenesis of acute kidney injury as well as chronic kidney diseases which are the main causes of end-stage renal failure.

In humans, the major agonists of the bradykinin B1 receptor are the kinins. Kinins are bioactive peptides produced from the proteolytic cleavage of kininogen proteins. The major kinin agonists of bradykinin B1 receptor are the decapeptide Kallidin, and the nonapeptide des-Arg$_{10}$-Kallidin (formed by the proteolytic cleavage the c-terminal arginine form Kallidin). Therefore, agents that can inhibit the binding of Kallidin and des-Arg$_{10}$-Kallidin to the bradykinin B1 receptor have the potential to treat or prevent bradykinin B1 receptor-mediated pathologies.

Accordingly, there is a need in the art for novel agents that inhibit the binding of Kallidin and des-Arg$_{10}$-Kallidin to the bradykinin B1 receptor for use in the treatment of bradykinin B1 receptor-mediated human pathologies.

SUMMARY OF THE INVENTION

The present invention provides antibodies, or antigen binding fragments thereof, that specifically bind Kallidin and des-Arg$_{10}$-Kallidin and prevent binding to the bradykinin B1 receptor. Such antibodies are particularly useful for treating Kallidin and des-Arg$_{10}$-Kallidin-associated diseases or disorders (e.g., pain or fibrosis). The invention also provides pharmaceutical compositions, as well as nucleic acids encoding anti-Kallidin and des-Arg$_{10}$-Kallidin antibodies, recombinant expression vectors and host cells for making such antibodies, or fragments thereof. Methods of using antibodies, or fragments thereof, of the invention to detect Kallidin and des-Arg$_{10}$-Kallidin or to modulate Kallidin and des-Arg$_{10}$-Kallidin activity, either in vitro or in vivo, are also encompassed by the invention. The invention also provides methods of making antibodies that specifically bind to des-Arg$_9$-Bradykinin and des-Arg$_{10}$-Kallidin-like peptide.

Accordingly, in one aspect the invention provides an isolated monoclonal antibody or antigen binding fragment thereof that:
a) specifically binds to Kallidin or des-Arg$_{10}$-Kallidin but not to Bradykinin or des-Arg$_9$-Bradykinin;
b) specifically binds to Kallidin or des-Arg$_{10}$-Kallidin with a KD of less than $1 \times 10^{-10}$ M;
c) specifically binds to Kallidin or des-Arg$_{10}$-Kallidin with a K$_{off}$ of less than $1 \times 10^4$ s$^{-1}$; or
d) specifically binds to Kallidin or des-Arg$_{10}$-Kallidin and inhibits binding to the bradykinin B1 receptor.

In one embodiment, the antibody or antigen binding fragment thereof binds to the N-terminal Lysine residue of Kallidin or des-Arg$_{10}$-Kallidin.

In another embodiment, the antibody or antigen binding fragment thereof inhibits the binding of Kallidin or des-Arg$_{10}$-Kallidin to a bradykinin B1 receptor.

In another embodiment, the antibody or antigen binding fragment thereof binds specifically to mouse Kallidin-like peptide (KLP).

In another embodiment, the antibody or antigen binding fragment thereof comprises a heavy chain variable domain comprising an HCDR3 amino acid sequence selected from the group consisting of:
a) SEQ ID NO: 7 [X$_1$Y X$_2$ X$_3$D X$_4$HAM X$_5$Y], wherein
   X$_1$ is Y, F or H,
   X$_2$ is R, D, A, V, L, I, M, F, Y or W,
   X$_3$ is Y, F, W or H,
   X$_4$ is D, E or Y, and,
   X$_5$ is D or E;
b) SEQ ID NO: 63 [X$_1$ EYDGX$_2$YX$_3$X$_4$LDX$_5$], wherein
   X$_1$ is W or F,
   X$_2$ is N or no amino acid;
   X$_3$ is Y or S,
   X$_4$ is D or P, and
   X$_5$ is F or Y;
c) SEQ ID NO: 13;
d) SEQ ID NO: 32;
e) SEQ ID NO: 40;
f) SEQ ID NO: 47; and
g) SEQ ID NO: 55.

In another embodiment, the antibody or antigen binding fragment thereof comprises an HCDR2 amino acid sequence selected from the group consisting of:
a) SEQ ID NO: 8 [YFX$_1$PX$_2$NGNTGYNQKFRG], wherein
   X$_1$ is D, R, A, V, L, I, M, F, Y or W, and
   X$_2$ is Y, D, E, N, or Q;
b) SEQ ID NO: 64 [WX$_1$DPENGDX$_2$X$_3$YAPKFQG], wherein
   X$_1$ is I, or V,
   X$_2$ is T, or S, and
   X$_3$ is G, or D;
c) SEQ ID NO: 14
d) SEQ ID NO: 33;
e) SEQ ID NO: 41;
f) SEQ ID NO: 48; and
g) SEQ ID NO: 56.

In another embodiment, the antibody or antigen binding fragment thereof comprises an HCDR1 amino acid sequence selected from the group consisting of:
a) SEQ ID NO: 9 [GYSFTDYX$_1$IY], wherein X$_1$ is N, W or Y;
b) SEQ ID NO: 65 [GFNIKDYYX$_1$H], wherein X$_1$ is L, or M;
c) SEQ ID NO: 15;
d) SEQ ID NO: 34;
e) SEQ ID NO: 42;
f) SEQ ID NO: 49; and
g) SEQ ID NO: 57.

In another embodiment, the antibody or antigen binding fragment thereof comprises a light chain variable domain comprising an LCDR3 amino acid sequence selected from the group consisting of:
a) SEQ ID NO: 10 [QQ $X_1$ $X_2$S $X_3$P $X_4$T], wherein
$X_1$ is Y, F or H,
$X_2$ is Y, F, H or W,
$X_3$ is Y, F, T or H, and,
$X_4$ is W, Y, F, H or L;
b) SEQ ID NO: 66 [Q$X_1X_2X_3$S$X_4$P$X_5$T], wherein
$X_1$ is Q or N,
$X_2$ is Y, F, D or H,
$X_3$ is Y, F, H or W,
$X_4$ is Y, F, T or H, and
$X_5$ is W, Y, F, H or L;
c) SEQ ID NO: 69 [$X_1$QGTHFPYT], wherein $X_1$ is L or M;
d) SEQ ID NO: 16;
e) SEQ ID NO: 35;
f) SEQ ID NO: 43;
g) SEQ ID NO: 50; and
h) SEQ ID NO: 58.

In another embodiment, the antibody or antigen binding fragment thereof comprises an LCDR2 amino acid sequence selected from the group consisting of:
a) SEQ ID NO: 11 [WASTR$X_1$], wherein $X_1$ is E, D, Q or N;
b) SEQ ID NO: 67 [$X_1$ASTR$X_2$], wherein
$X_1$ is W or G, and
$X_2$ is E, D, Q or N;
c) SEQ ID NO: 17;
d) SEQ ID NO: 36;
e) SEQ ID NO: 51; and
f) SEQ ID NO: 59.

In another embodiment, the antibody or antigen binding fragment thereof comprises an LCDR1 amino acid sequence selected from the group consisting of:
a) SEQ ID NO: 12 [KSSQSLL $X_1$SSNQKN $X_2$LA], wherein
$X_1$ is W, H, Y or F, and
$X_2$ is H or Y;
b) SEQ ID NO: 68 [KSSQSLL$X_1X_2$S$X_3$Q$X_4$N$X_5$LA], wherein
$X_1$ is W, H, Y or F,
$X_2$ is S or G,
$X_3$ is N or D,
$X_4$ is K or R,
$X_5$ is H or Y.
c) SEQ ID NO: 70 [KSSQSLLYSNG$X_1$TYLN], wherein
$X_1$ is K or E;
b) SEQ ID NO: 18;
c) SEQ ID NO: 37;
d) SEQ ID NO: 44;
e) SEQ ID NO: 52; and
f) SEQ ID NO: 60.

In another embodiment, the antibody or antigen binding fragment comprises a light chain variable domain comprising an LCDR3 amino acid sequence selected from the group consisting of:
a) SEQ ID NO: 10 [QQ $X_1$ $X_2$S $X_3$P $X_4$T], wherein
$X_1$ is Y, F or H,
$X_2$ is Y, F, H or W,
$X_3$ is Y, F, T or H, and,
$X_4$ is W, Y, F, H or L;
b) SEQ ID NO: 66 [Q$X_1X_2X_3$S$X_4$P$X_5$T], wherein
$X_1$ is Q or N,
$X_2$ is Y, F, D or H,
$X_3$ is Y, F, H or W,
$X_4$ is Y, F, T or H, and
$X_5$ is W, Y, F, H or L;
c) SEQ ID NO: 69 [$X_1$QGTHFPYT], wherein $X_1$ is L or M;
d) SEQ ID NO: 16;
e) SEQ ID NO: 35;
f) SEQ ID NO: 43;
g) SEQ ID NO: 50; and
h) SEQ ID NO: 58.

In another embodiment, the antibody or antigen binding fragment thereof comprises an LCDR2 amino acid sequence selected from the group consisting of:
a) SEQ ID NO: 11 [WASTR$X_1$], wherein $X_1$ is E, D, Q or N;
b) SEQ ID NO: 67 [$X_1$ASTR$X_2$], wherein
$X_1$ is W or G, and
$X_2$ is E, D, Q or N;
c) SEQ ID NO: 17;
d) SEQ ID NO: 36;
e) SEQ ID NO: 51; and
f) SEQ ID NO: 59.

In another embodiment, the antibody or antigen binding fragment thereof comprises an LCDR1 amino acid sequence selected from the group consisting of:
a) SEQ ID NO: 12 [KSSQSLL $X_1$SSNQKN $X_2$LA], wherein
$X_1$ is W, H, Y or F, and
$X_2$ is H or Y;
b) SEQ ID NO: 68 [KSSQSLL$X_1X_2$S$X_3$Q$X_4$N$X_5$LA], wherein
$X_1$ is W, H, Y or F,
$X_2$ is S or G,
$X_3$ is N or D,
$X_4$ is K or R,
$X_5$ is H or Y.
c) SEQ ID NO: 70 [KSSQSLLYSNG$X_1$TYLN], wherein
$X_1$ is K or E;
b) SEQ ID NO: 18;
c) SEQ ID NO: 37;
d) SEQ ID NO: 44;
e) SEQ ID NO: 52; and
f) SEQ ID NO: 60.

In another embodiment, the antibody or antigen binding fragment thereof comprises a heavy chain variable region comprising the HCDR3, HCDR2 and HCDR1 region amino acid sequences set forth in SEQ ID NOs 13, 14, and 15, respectively, and one or more amino acid substitutions at positions selected from the group consisting of H1, H5, H9, H11, H12, H16, H38, H40, H41, H43, H44, H66, H75, H79, H81, H82A, H83, H87, and H108 according to Kabat.

In another embodiment, the antibody or antigen binding fragment thereof comprises a light chain variable region comprising the LCDR3, LCDR2 and LCDR1 region amino acid sequences set forth in SEQ ID NOs 16, 17, and 18, respectively, and one or more amino acid substitution at positions selected from the group consisting of L5, L9, L15, L18, L19, L21, L22, L43, L63, L78, L79, L83, L85, L100 and L104, according to Kabat.

In another embodiment, the antibody or antigen binding fragment thereof comprises a heavy chain variable region amino acid sequence with at least 90% identity to an amino acid sequence selected from the group consisting of SEQ ID NOs: 19, 20, 21, 22, 24, 25, 38, 45, 53, and 61.

In another embodiment, the antibody or antigen binding fragment thereof comprises a light chain variable domain amino acid sequence with at least 90% identity to an amino acid sequence selected from the group consisting of SEQ ID NOs: 26, 27, 28, 29, 29, 30, 31, 39, 46, 54, and 62.

In another embodiment, the antibody or antigen binding fragment thereof comprises a light chain variable region amino acid sequence with at least 90% identity to an amino acid sequence selected from the group consisting of SEQ ID NOs: 26, 27, 28, 29, 29, 30, 31, 39, 46, 54, and 62.

In another embodiment, the antibody or antigen binding fragment thereof comprises a heavy chain variable domain comprising an amino acid sequence selected from the group consisting of: SEQ ID NO: 19, 20, 21, 22, 24, 25, 38, 45, 53, and 61.

In another embodiment, the antibody or antigen binding fragment thereof comprises a light chain variable domain amino acid sequence selected from the group consisting of: SEQ ID NO: 26, 27, 28, 29, 29, 30, 31, 39, 46, 54, and 62.

In another embodiment, the antibody or antigen binding fragment thereof comprises an amino acid sequence selected from the group consisting of: SEQ ID NO: 26, 27, 28, 29, 29, 30, 31, 39, 46, 54, and 62.

In another embodiment, the antibody or antigen binding fragment thereof comprises the heavy chain and light chain variable region amino acid sequences set forth in SEQ ID NO: 19 and 26, SEQ ID NO: 20 and 27, SEQ ID NO: 21 and 28; SEQ ID NO: 22 and 28; SEQ ID NO: 23 and 29; SEQ ID NO: 24 and 30; SEQ ID NO: 25 and 31; SEQ ID NO: 38 and 39, SEQ ID NO: 45 and 46, SEQ ID NO: 53 and 54, or SEQ ID NO: 61 and 62, respectively.

In another aspect, the invention provides an antibody, or antigen binding fragment thereof, that specifically binds to Kallidin and des-Arg$_{10}$-Kallidin, wherein the antibody, or antigen binding fragment thereof, competes for binding to Kallidin and des-Arg$_{10}$-Kallidin with an antibody comprising the heavy chain and light chain variable region amino acid sequences set forth in SEQ ID NO: 19 and 26, SEQ ID NO: 38 and 39, SEQ ID NO: 45 and 46, SEQ ID NO: 53 and 54, or SEQ ID NO: 61 and 62, respectively.

In another aspect, the invention provides an isolated monoclonal antibody or antigen binding fragment thereof that competes for binding to Kallidin or des-Arg$_{10}$-Kallidin with the antibody of any one of the preceding claims, and does not bind to Bradykinin or desArg$_9$-Bradykinin.

In another aspect, the invention provides an isolated monoclonal antibody or antigen binding fragment thereof that specifically binds to a conformational epitope of Kallidin (KD) or desArg10-Kallidin (DAKD) which adopts a Pro4 kink conformation comprising a type II tight turn at Proline 4 of the KD or DAKD). In one embodiment, the Pro4 kink conformation of KD or DAKD further comprises amino acid repeats of a sigmoid shape which align the hydrophobic side chains of the amino acids in a spatially stacking mode. In another embodiment, the antibody or antigen binding fragment thereof comprises (a) specifically binds Kallidin or des-Arg$_{10}$-Kallidin but not to Bradykinin or des-Arg$_9$-Bradykinin; b) specifically binds to Kallidin or des-Arg$_{10}$-Kallidin with a KD of less than $1\times10^{-10}$ M; c) specifically binds to Kallidin or des-Arg$_{10}$-Kallidin with a $K_{off}$ of less than $1\times10^4$ s$^{-1}$; or d) specifically binds to Kallidin or des-Arg$_{10}$-Kallidin and inhibits binding to the bradykinin B1 receptor.

In another aspect, the antibody or antigen binding fragment of the invention is conjugated to a diagnostic or therapeutic agent.

In another aspect, the invention provides isolated nucleic acid encoding the amino acid sequence of the antibody, or antigen binding fragment thereof, of the invention.

In another aspect, the invention provides recombinant expression vector comprising the nucleic acid of the invention.

In another aspect, the invention provides a host cell comprising the recombinant expression vector of the invention.

In another aspect, the invention provides a method of producing an antibody that binds specifically to Kallidin and des-Arg$_{10}$-Kallidin, comprising culturing the host cell of the invention under conditions such that an antibody that binds specifically to Kallidin and des-Arg$_{10}$-Kallidin is produced by the host cell.

In another aspect, the invention provides a pharmaceutical composition comprising the antibody, or antigen binding fragment thereof, of the invention and one or more pharmaceutically acceptable carriers.

In another aspect, the invention provides a method for treating a disease or disorder Kallidin or des-Arg$_{10}$-Kallidin-associated disease or disorder, the method comprising administering to a subject in need of thereof the pharmaceutical composition of the invention.

In one embodiment, the disease or disorder is chronic pain.

In another aspect, the invention provides a method of generating an antibody that specifically binds to des-Arg$_9$-Bradykinin and des-Arg$_{10}$-Kallidin-like peptide comprising: immunizing an animal with an immunogen comprising a peptide, wherein the peptide consists of the amino acid sequence set forth in SEQ ID No.11, and wherein the amino terminal arginine of the peptide is indirectly coupled to a carrier moiety through a linker moiety, such that an antibody that specifically binds to des-Arg$_9$-Bradykinin, des-Arg$_{10}$-Kallidin and des-Arg$_{10}$-Kallidin-like peptide is produced by the immune system of the animal.

In another embodiment, the method further comprises isolating from the animal, the antibody, a nucleic isolating encoding the antibody, or an immune cell expressing the antibody.

In one embodiment, the carrier moiety is a protein. In another embodiment, the protein is Keyhole limpet hemocyanin (KLH). In another embodiment, wherein the linker moiety comprises [Gly-Gly-Gly]n, wherein n is at least 1.

BRIEF DESCRIPTION OF THE DRAWINGS

FIG. 3 depicts amino acid sequence alignments of the variable regions of the murine and humanized F151 antibody. All identical residues are listed in the alignment, while homologous residues are identified by "+" sign and non-homologous residues are left blank. Figure discloses SEQ ID NOS 19, 24, 26, and 30, respectively, in order of appearance.

FIG. 7 depicts an amino acid sequence alignment of the light chain variable regions of exemplary murine anti-kallidin antibodies of the invention. Amino acid residues that interact with kallidin are marked with asterisks. Figure discloses SEQ ID NOS 134, 125, 124, 123, 126, and 131, respectively, in order of appearance.

FIG. 15 depicts an alignment of the F151 heavy chain (A) and light chain (B) amino acid sequences with the closest human germline amino acid sequences.

FIG. 16 depicts an alignment of the F151 heavy chain (A) and light chain (B) with a heavy chain locus (1-08 & 1-18) and light chain (V☐IV-B3) locus of the VH1 sub-family. CDR regions and Vernier regions are indicated in boldface and humanizing mutations are underlined.

DETAILED DESCRIPTION

Figure 1:
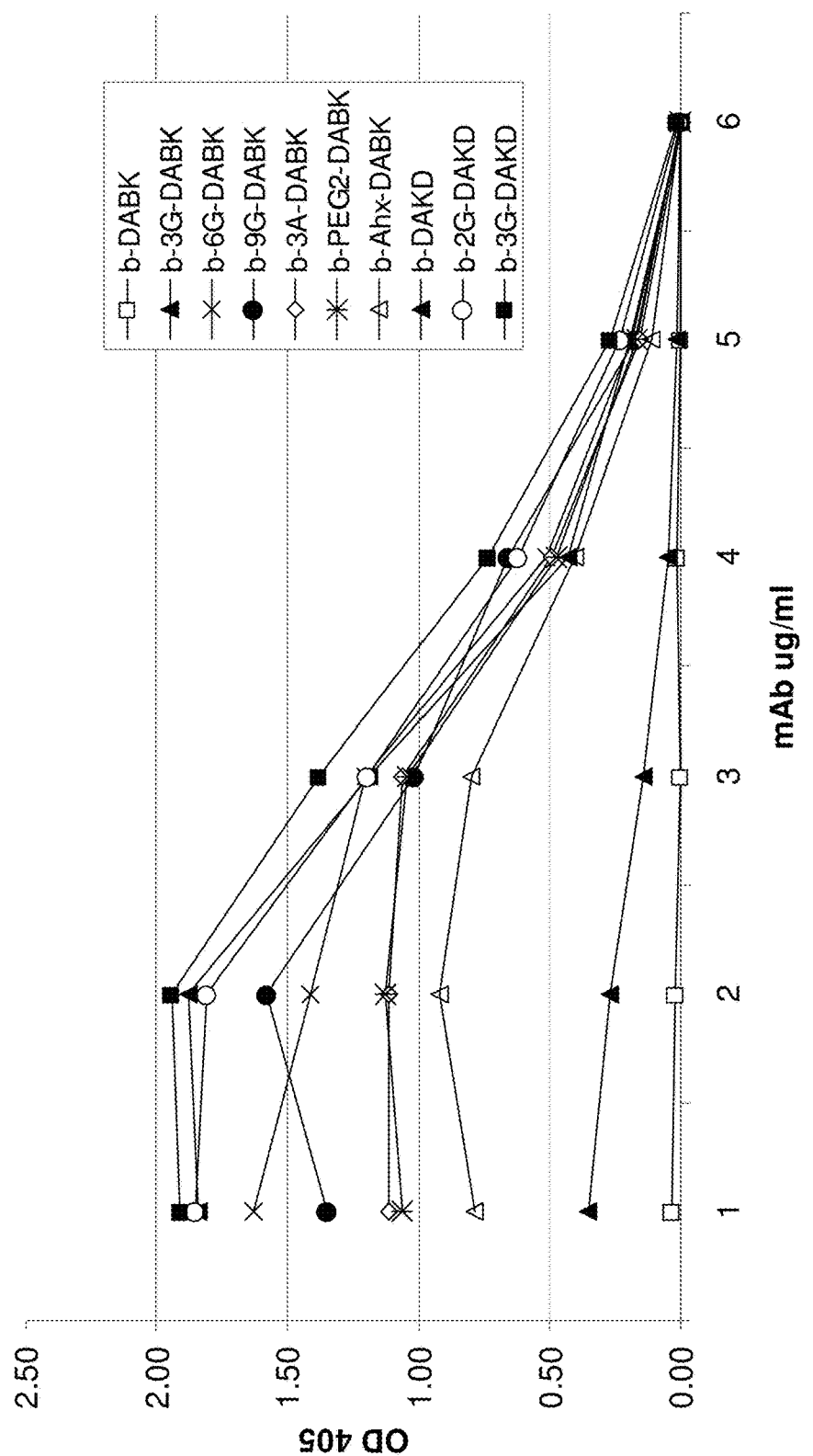
FIG. 1 depicts the results of ELISA assays demonstrating binding of EE1 antibody to kinin peptides.

The present invention provides antibodies that specifically bind to Kallidin and des-$Arg_{10}$-Kallidin and prevent binding to the bradykinin B1 receptor. Such antibodies are particularly useful for treating Kallidin and des-$Arg_{10}$-Kallidin-associated disease or disorders (e.g., pain). The invention also provides pharmaceutical compositions, as well as nucleic acids encoding anti-Kallidin and des-$Arg_{10}$-Kallidin antibodies, recombinant expression vectors and host cells for making such antibodies, or fragments thereof. Methods of using antibodies of the invention to detect Kallidin and des-$Arg_{10}$-Kallidin or to modulate Kallidin and des-$Arg_{10}$-Kallidin activity, either in vitro or in vivo, are also encompassed by the invention.

I. Definitions

In order that the present invention may be more readily understood, certain terms are first defined.

As used herein, the term "Kallidin" refers to a peptide comprising or consisting of the amino acid sequence KRPPGFSPFR (SEQ ID NO. 1).

As used herein, the term "des-$Arg_{10}$-Kallidin" refers to a peptide comprising or consisting of the amino acid sequence KRPPGFSPF (SEQ ID NO. 2).

As used herein, the term "mouse Kallidin" or "Kallidin-like peptide" refers to a peptide comprising or consisting of the amino acid sequence RRPPGFSPFR (SEQ ID NO. 3)

As used herein, the term "mouse des-$Arg_{10}$-Kallidin" or "des-$Arg_{10}$Kallidin-like peptide" refers to a peptide comprising or consisting of the amino acid sequence RRPPGFSPF (SEQ ID NO. 4).

As used herein, the term "Bradykinin" refers to a peptide comprising or consisting of the amino acid sequence RPPGFSPFR (SEQ ID NO. 5).

As used herein, the term "des-$Arg_9$-Bradykinin" refers to a peptide comprising or consisting of the amino acid sequence RPPGFSPF (SEQ ID NO. 6).

As used herein, the term "antibody" refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated $V_H$ or VH) and a heavy chain constant region ($C_H$ or CH). The heavy chain constant region comprises three domains, $C_H1$, $C_H2$ and $C_H3$. Each light chain comprises a light chain variable region (abbreviated $V_L$) and a light chain constant region ($C_L$ or CL). The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

As used herein, the term "antigen-binding fragment" of an antibody includes any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding portions include: (i) Fab fragments; (ii) F(ab.)$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment."

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. In an embodiment of the invention, the term "CDR" is a CDR as defined by Kabat, based on sequence comparisons.

As used herein the term "framework (FR) amino acid residues" refers to those amino acids in the framework region of an Ig chain. The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs.

As used herein, the term "specifically binds to" refers to the ability of an antibody or an antigen-binding fragment thereof to bind to an antigen with an Kd of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more. The term also encompasses refers to the ability of an antibody or an antigen-binding fragment thereof to bind to an antigen with an affinity that is at least two-fold greater than its affinity for a nonspecific antigen. It shall be understood, however, that an antibody, or an antigen-binding fragment thereof, is capable of specifically binding to two or more antigens which are related in sequence (e.g., Kallidin or des-Arg10-Kallidin and mouse Kallidin or des-Arg10-Kallidin).

As used herein, the term "antigen" refers to the binding site or epitope recognized by an antibody or antigen binding fragment thereof.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a recombinant expression vector has been introduced. It should be understood that this term is intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "treat," "treating," and "treatment" refer to therapeutic or preventative measures described herein. The methods of "treatment" employ administration to a subject, an antibody or antigen binding fragment of the present invention, for example, a subject having a Kallidin and des-Arg$_{10}$-Kallidin-associated disease or disorder (e.g. an inflammatory disease) or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "Kallidin or des-Arg$_{10}$-Kallidin-associated disease or disorder" includes disease states and/or symptoms associated with a disease state, where altered levels or activity of Kallidin or des-Arg$_{10}$-Kallidin are found. Exemplary Kallidin or des-Arg$_{10}$-Kallidin-associated diseases or disorders include, but are not limited to, pain and fibrosis.

As used herein, the term "effective amount" refers to that amount of an antibody or an antigen binding fragment thereof that binds Kallidin or des-Arg$_{10}$-Kallidin, which is sufficient to effect treatment, prognosis or diagnosis of a Kallidin or des-Arg$_{10}$-Kallidin-associated disease or disorder, as described herein, when administered to a subject. A therapeutically effective amount will vary depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 1 ug to about 5,000 mg, about 1 mg to about 1,000 mg, about 10 mg to about 100 mg, of an antibody or antigen binding fragment thereof, according to the invention. Dosage regiments may be adjusted to provide the optimum therapeutic response. An effective amount is also one in which any toxic or detrimental effects (i.e., side effects) of an antibody or antigen binding fragment thereof are minimized or outweighed by the beneficial effects.

As used herein, the term "subject" includes any human or non-human animal.

As used herein, the term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain.

It is noted here that, as used in this specification and the appended claims, the singular forms "a," "an," and "the" include plural reference unless the context clearly dictates otherwise.

II. Anti-Kallidin or des-Arg$_{10}$-Kallidin Antibodies

In one aspect the invention provides antibodies, or antigen binding fragments thereof, that specifically bind to Kallidin or des-Arg$_{10}$-Kallidin. Exemplary VH, VL and CDR amino acid sequences of the antibodies of the invention are set forth in Table 1.

TABLE 1

VH, VL and CDR amino acid sequences of exemplary
anti-Kallidin or des-Arg₁₀-Kallidin antibodies.

| Antibody Clone | Sequence | SEQ ID NO. |
|---|---|---|
| F151 HCDR3 consensus | X₁YX₂X₃DX₄HAMX₅Y<br>where:<br>X₁ is Y, F or H;<br>X₂ is R, D, A, V, L, I, M, F, Y or W;<br>X₃ is Y, F, W or H;<br>X₄ is D, E or Y; and<br>X₅ is D or E. | 7 |
| F151 HCDR2 consensus | YFX₁PX₂NGNTGYNQKFRG<br>where:<br>X₁ is D, R, A, V, L, I, M, F, Y or W; and<br>X₂ is Y, D, E, N, or Q. | 8 |
| F151 HCDR1 consensus | GYSFTDYX₁IY<br>Where X₁ is N, W or Y. | 9 |
| F151 LCDR3 consensus | QQX₁X₂SX₃PX₄T<br>where:<br>X₁ is Y, F or H;<br>X₂ is Y, F, H or W;<br>X₃ is Y, F, T or H; and<br>X₄ is W, Y, F, H or L. | 10 |
| F151 LCDR2 consensus | WASTRX₁<br>where X₁ is E, D, Q or N. | 11 |
| F151 LCDR1 consensus | KSSQSLLX₁SSNQKNX₂LA<br>where:<br>X₁ is W, H, Y or F; and<br>X₂ is H or Y. | 12 |
| F151 HCDR3 | YYRYDDHAMDY | 13 |
| F151 HCDR2 | YFDPYNGNTGYNQKFRG | 14 |
| F151 HCDR1 | GYSFTDYNIY | 15 |
| F151 LCDR3 | QQYYSYPWT | 16 |
| F151 LCDR2 | WASTRES | 17 |
| F151 LCDR1 | KSSQSLLYSSNQKNYLA | 18 |
| F151 VH | EIQLQQSGPELVKPGTSVKVSCKASGYSFTDYNIYWVKQSHGKSLEWIGYFDPYNGNTGYNQKFRGKATLTVDKSSSTAFMHLSSLTSDDSAVYYCANYYRYDDHAMDYWGQGTSVTVSS | 19 |
| F151 Humanized HC1 | EIQLVQSGPEVKKPGASVKVSCKASGYSFTDYNIYWVKQSPGKSLEWIGYFDPYNGNTGYNQKFRGKATLTVDKSSSTAFMHLSSLTSEDSAVYYCANYYRYDDHAMDYWGQGTSVTVSS | 20 |
| F151 Humanized HC2a | QIQLVQSGAEVKKPGASVKVSCKASGYSFTDYNIYWVKQSPGKGLEWIGYFDPYNGNTGYNQKFRGKATLTVDKSSSTAYMHLSSLTSEESAVYYCANYYRYDDHAMDYWGQGTSVTVSS | 21 |
| F151 Humanized HC2b | QIQLVQSGAEVKKPGASVKVSCKASGYSFTDYNIYWVKQSPGKGLEWIGYFDPYNGNTGYNEKFRGKATLTVDKSSSTAYMHLSSLTSEESAVYYCANYYRYDDHAMDYWGQGTSVTVSS | 22 |
| F151 Humanized HC2c | QIQLVQSGAEVKKPGASVKVSCKASGYSFTDYNIYWVKQSPGKGLEWIGYFDPYNGNTGYNQKFRGKATLTVDKSSSTAYMHLSSKTSEESAVYYCANYYRYDDHAMDYWGQGTSVTVSS | 23 |
| F151 Humanized HC3a | QIQLVQSGAEVKKPGASVKVSCKASGYSFTDYNIYWVRQAPGQGLEWIGYFDPYNGNTGYNQKFRGRATLTVDKSTSTAYMELRSLRSDDTAVYYCANYYRYDDHAMDYWGQGTLVTVSS | 24 |

TABLE 1-continued

VH, VL and CDR amino acid sequences of exemplary anti-Kallidin or des-Arg$_{10}$-Kallidin antibodies.

| Antibody Clone | Sequence | SEQ ID NO. |
|---|---|---|
| F151 Humanized HC3b | QVQLVQSGAEVKKPGASVKVSCKASGYSFTDYNIYWVRQ APGQGLEWMGYFDPYNGNTGYNQKFRGRVTMTTDTSTST AYMELRSLRSDDTAVYYCANYYRYDDHAMDYWGQGTLVT VSS | 25 |
| F151 VL | DIVMSQSPSSLAVSVGEKVTMSCKSSQSLLYSSNQKNYL AWYQQKPGQSPKPLIYWASTRESGVPDRFTGSGSGTDFT LTISSVKAEDLAIYYCQQYYSYPWTEGGGTKLEIK | 26 |
| F151 Humanized LC1 | DIVMSQSPSSLAASVGDRVTMSCKSSQSLLYSSNQKNYL AWYQQKPGKSPKPLIYWASTRESGVPDRFTGSGSGTDFT LTISSVQAEDLAIYYCQQYYSYPWTEGGGTKLEIK | 27 |
| F151 Humanized LC2a | DIVMTQSPSSLSASVGDRVTISCKSSQSLLYSSNQKNYL AWYQQKPGKSPKPLIYWASTRESGVPDRFSGSGSGTDFT LTISSVQAEDLATYYCQQYYSYPWTFGGGTKLEIK | 28 |
| F151 Humanized LC2b | DIVMTQSPSSLSASVGDRVTISCKSSQSLLYSSNQKNYL AWYQQKPGKSPKPLIYWASTRESGVPDRFSGSGSGTDFT LTISSVQAEDKATYYCQQYYSYPWTFGGGTKLEIK | 29 |
| F151 Humanized LC3a | DIVMTQSPDSLAVSLGERATINCKSSQSLLYSSNQKNYL AWYQQKPGQPPKPLIYWASTRESGVPDRFSGSGSGTDFT LTISSLQAEDVAVYYCQQYYSYPWTFGQGTKVEIK | 30 |
| F151 Humanized LC3b | DIVMTQSPDSLAVSLGERATINCKSSQSLLYSSNQKNYL AWYQQKPGQPPKLLIYWASTRESGVPDRFSGSGSGTDFT LTISSLQAEDVAVYYCQQYYSYPWTFGQGTKVEIK | 31 |
| B21 HCDR3 | WEYDGYYDLDY | 32 |
| B21 HCDR2 | WIDPENGDTGYARKFQG | 33 |
| B21 HCDR1 | GFNIKDYYLH | 34 |
| B21 LCDR3 | LQGTHFPYT | 35 |
| B21 LCDR2 | LVSKLDS | 36 |
| B21 LCDR1 | KSSQSLLYSNGKTYLN | 37 |
| B21 VH | EVQLQQSGAELVRSGASVKLSCTASGFNIKDYYLHWVKQ RPEQGLEWIGWIDPENGDTGYARKFQGKATMTADTSSNT VYLHLSSLTSEDTAVYYFNAWEYDGYYDLDYWGQGTSVT VSS | 38 |
| B21 VL | DVVMTQTPLTLSVTIGQPASISCKSSQSLLYSNGKTYLN WLLQRPGQSPKRLIYLVSKLDSGVPDRFTGSGSGTDFTL KIIRVEAEDLGVYYCLQGTHFPYTEGGGTKLEIK | 39 |
| C63 HCDR3 | EDYGGDY | 40 |
| C63 HCDR2 | EIRSKSNNYATHYAESVKG | 41 |
| C63 HCDR1 | GETESNYWMN | 42 |
| C63 LCDR3 | QQYYSYPYT | 43 |
| C63 LCDR2 | WASTRES | 17 |
| C63 LCDR1 | KSSQSLLYSSDQRNYLA | 44 |
| C63 VH | EVKLEESGGGLVQPGGSMKLSCVASGFTFSNYWMNWVRQ SPEKGLEWVAEIRSKSNNYATHYAESVKGRFTISRDDSK SSVYLQMNNLRAEDTGIYYCIGEDYGGDYWGQGTSVTVS S | 45 |
| C63 VL | DIVMSQSPSSLAVSVGEKVTMSCKSSQSLLYSSDQRNYL AWYQQRSGQSPKLLIYWASTRESGVPDRFTGSGSGTDFT LTISSVKAEDLAVYYCQQYYSYPYTEGGGTKLEIK | 46 |
| I22 HCDR3 | FEYDGNYSPLDF | 47 |
| I22 HCDR2 | WVDPENGDSDYAPKFQ | 48 |

TABLE 1-continued

VH, VL and CDR amino acid sequences of exemplary anti-Kallidin or des-Arg$_{10}$-Kallidin antibodies.

| Antibody Clone | Sequence | SEQ ID NO. |
|---|---|---|
| I22 HCDR1 | GFNIKDYYMH | 49 |
| I22 LCDR3 | QNDHSYPLT | 50 |
| I22 LCDR2 | GASTRES | 51 |
| I22 LCDR1 | KSSQSLLNSGNQKNYLA | 52 |
| I22 VH | EVQLQQSGAELVRSGASVKLSCTASGFNIKDYYMHWVKQRPEQGLEWIGWVDPENGDSDYAPKFQGKATMTADTSSNTVYLQFSSLTSEDTAVYYCNAFEYDGNYSPLDFWGQGTSVTVSS | 53 |
| I22 VL | DIVMTQSPSSLSVSAGEKVTMSCKSSQSLLNSGNQKNYLAWYQQKPGQPPKLLIYGASTRESGVPDRFTGSGSGTDFTLTISSVQAEDLAVYYCQNDHSYPLTFGAGTKLELK | 54 |
| I54 HCDR3 | FEYDGNYSPLDF | 55 |
| I54 HCDR2 | WVDPENGDSDYAPKFQG | 56 |
| I54 HCDR1 | GFNIKDYYMH | 57 |
| I54 LCDR3 | MQGTHFPYT | 58 |
| I54 LCDR2 | LVSKLDS | 59 |
| I54 LCDR1 | KSSQSLLYSNGETYLN | 60 |
| I54 VH | EVQLQQSGAELVRSGASVKLSCTASGFNIKDYYMHWVKQRPEQGLEWIGWVDPENGDSDYAPKFQGKATMTADTSSNTVYLQFSSLTSEDTAVYYCNAFEYDGNYSPLDFWGQGTSVTVSS | 61 |
| I54 VL | DVVMTQTPLTLSVPIGQPASISCKSSQSLLYSNGETYLNWLLQRPGQSPKRLIYLVSKLDSGVPDRFTGSRSGTDFTLKISRVESEDLGVYYCMQGTHFPYTFGGGTKLEIK | 62 |
| B21/I22/I54 HCDR3 consensus | X$_1$EYDGX$_2$YX$_3$X$_4$LDX$_5$ where:<br>X$_1$ is W or F;<br>X$_2$ is N or no amino acid;<br>X$_3$ is Y or S;<br>X$_4$ is D or P; and<br>X$_5$ is F or Y. | 63 |
| B21/I22/I54 HCDR2 consensus | WX$_1$DPENGDX$_2$X$_3$YAPKFQG where:<br>X$_1$ is I, or V;<br>X$_2$ is T, or S; and<br>X$_3$ is G, or D. | 64 |
| B21/I22/I54 HCDR1 consensus | GFNIKDYYX$_1$H where X$_1$ is L, or M. | 65 |
| F151/C63/I22 LCDR3 consensus | QX$_1$X$_2$X$_3$SX$_4$PX$_5$T where:<br>X$_1$ is Q or N;<br>X$_2$ is Y, F, D or H;<br>X$_3$ is Y, F, H or W;<br>X$_4$ is Y, F, T or H; and<br>X$_5$ is W, Y, F, H or L. | 66 |
| F151/C63/I22 LCDR2 | X$_1$ASTRX$_2$ consensus where:<br>X$_1$ is W or G; and<br>X$_2$ is E, D, Q or N | 67 |

TABLE 1-continued

VH, VL and CDR amino acid sequences of exemplary
anti-Kallidin or des-Arg$_{10}$-Kallidin antibodies.

| Antibody Clone | Sequence | SEQ ID NO. |
|---|---|---|
| F151/C63/I22 LCDR1 | KSSQSLLX$_1$X$_2$SX$_3$QX$_4$NX$_5$LA consensus where: X$_1$ is W, H, Y or F; X$_2$ is S or G; X$_3$ is N or D; X$_4$ is K or R; X$_5$ is H or Y. | 68 |
| B21/I54 LCDR3 consensus | X$_1$QGTHFPYT where: X$_1$ is L or M; | 69 |
| B21/I54 LCDR2 both identical | LVSKLDS | 36 |
| B21/I54 LCDR1 consensus | KSSQSLLYSNGX$_1$TYLN where: X$_1$ is K or E; | 70 |

In certain embodiments, the antibody, or antigen binding fragment thereof, comprises one or more CDR region amino acid sequence selected from the group consisting of SEQ ID NO: 7, 8, 9, 10, 11, 12, 13, 14, 15, 16, 17, 18, 32, 33, 34, 35, 36, 37, 40, 41, 42, 43, 44, 47, 48, 49, 50, 51 52, 55, 56, 57, 58, 59, 60, 61, 62, 63, 64, 65, 66, 67, 68, 69, and 70.

In other embodiments, the antibody, or antigen binding fragment thereof, comprises HCDR3, HCDR2 and HCDR1 region amino acid sequences selected from the group consisting of:
 a) SEQ ID NO: 7, 8, and 9;
 b) SEQ ID NO: 13, 14, and 15;
 c) SEQ ID NO: 32, 33, and 34;
 d) SEQ ID NO: 40, 41, and 42;
 e) SEQ ID NO: 47, 48, and 49;
 f) SEQ ID NO: 55, 56, and 57; and
 g) SEQ ID NO: 63, 64, and 65, respectively.

In other embodiments, the antibody, or antigen binding fragment thereof, comprises the LCDR3, LCDR2 and LCDR1 region amino acid sequences selected from the group consisting of:
 a) SEQ ID NO: 10, 11, and 12;
 b) SEQ ID NO: 16, 17, and 18;
 c) SEQ ID NO: 35, 36, and 37;
 d) SEQ ID NO: 43, 17, and 44;
 e) SEQ ID NO: 50, 51, and 52;
 f) SEQ ID NO: 58, 59, and 60;
 g) SEQ ID NO: 66, 67, and 68; and
 h) SEQ ID NO: 69, 25, and 70, respectively.

In other embodiments, the antibody, or antigen binding fragment thereof, comprises the HCDR3, HCDR2, HCDR1, LCDR3, LCDR2 and LCDR1 region amino acid sequences selected from the group consisting of:
 a) SEQ ID NO: 7, 8, 9, 10, 11, and 12;
 b) SEQ ID NO: 13, 14, 15, 16, 17, and 18;
 c) SEQ ID NO: 32, 33, 34, 35, 36 and 37;
 d) SEQ ID NO: 40, 41, 42, 43, 17, and 44;
 e) SEQ ID NO: 47, 48, 49, 50, 51, and 52; and
 f) SEQ ID NO: 55, 56, 57, 58, 59, and 60, respectively.

In other embodiment, the invention provides humanized antibodies, or antigen binding fragments thereof, comprising one or more CDR regions (or conservatively modified variants thereof) from the murine antibodies disclosed herein. Any method of humanization can be employed to generate the humanized antibodies of the invention. Suitable methods are disclosed herein and specifically exemplified in Example 4.

In a one particular embodiment, the humanized antibody, or antigen binding fragment thereof comprises:
 a heavy chain variable region comprising the HCDR3, HCDR2 and HCDR1 region amino sequences set forth in 13, 14, and 15, respectively, and one or more amino acid substitution at positions selected from the group consisting of H1, H5, H9, H11, H12, H16, H38, H40, H41, H43, H44, H66, H75, H79, H81, H82A, H83, H87, and H108; and/or
 a light chain variable region comprising the LCDR3, LCDR2 and LCDR1 region amino sequences set forth in 16, 17, and 18, respectively, and one or more amino acid substitution at positions selected from the group consisting of L5, L9, L15, L18, L19, L21, L22, L43, L63, L78, L79, L83, L85, L100 and L104 (according to the Kabat numbering convention).

In other embodiments, the antibody, or antigen binding fragment thereof, comprises the VH region amino acid sequences set forth in SEQ ID NO: 19, 20, 21, 22, 24, 25, 38, 45, 53, and/or 61.

In other embodiments, the antibody, or antigen binding fragment thereof, comprises the VL region amino acid sequences set forth in SEQ ID NO: 26, 27, 28, 29, 29, 30, 31, 39, 46, 54, and/or 62.

In other embodiments, the antibody, or antigen binding fragment thereof, comprises the VH and VL region amino acid sequences selected from the group consisting of: SEQ ID NO: 19 and 26, SEQ ID NO: 20 and 27, SEQ ID NO: 21 and 28; SEQ ID NO: 22 and 28; SEQ ID NO: 23 and 29; SEQ ID NO: 24 and 30; SEQ ID NO: 25 and 31; SEQ ID NO: 38 and 39, SEQ ID NO: 45 and 46, SEQ ID NO: 53 and 54, or SEQ ID NO: 61 and 62, respectively.

In certain embodiments, the antibody, or antigen binding fragment thereof, comprises one or more CDR region amino acid sequence selected from the group consisting of SEQ ID NO: 7, 8, 9, 10, 11, 12, 13, 14, 15, 16, 17, 18, 32, 33, 34, 35, 36, 37, 40, 41, 42, 43, 44, 47, 48, 49, 50, 51 52, 55, 56, 57, 58, 59 and 60, wherein the one or more CDR region amino acid sequences comprises at least one or more conservative amino acid substitutions.

The present invention also encompasses "conservative amino acid substitutions" in the CDR amino acid sequences (e.g., SEQ ID NOs: 8, 9, 10, 11, 12, 13, 14, 15, 16, 17, 18, 32, 33, 34, 35, 36, 37, 40, 41, 42, 43, 44, 47, 48, 49, 50, 51 52, 55, 56, 57, 58, 59 and 60) of the antibodies of the invention, i.e., amino acid sequence modifications which do not abrogate the binding of the antibody to the antigen, e.g., Kallidin or des-Arg10-Kallidin. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in an anti-Kallidin or des-Arg10-Kallidin antibody is preferably replaced with another amino acid residue from the same class. Methods of identifying amino acid conservative substitutions which do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:412-417 (1997)).

In another embodiment, the present invention provides anti-Kallidin or des-Arg10-Kallidin antibodies, or antigen binding fragment thereof, that comprise a VH and/or VL region amino acid sequence with about 80%, 85%, 86%, 87%, 88%, 89%, 90%, 91%, 92%, 93%, 94%, 95%, 96%, 97%, 98%, or 99%, identity to the VH region amino acid sequence set forth in SEQ ID NO: 19, 20, 21, 22, 24, 25, 38, 45, 53, or 61, or the VL region amino acid sequence set forth in SEQ ID NO: 26, 27, 28, 29, 29, 30, 31, 39, 46, 54, or 62, respectively.

In another embodiment, the present invention provides anti-Kallidin or des-Arg10-Kallidin antibodies that bind to the same epitope and/or cross compete with an antibody, or antigen binding fragment thereof comprising the VH and VL region amino acid sequences set forth in SEQ ID NO: 19 and 25, SEQ ID NO: 38 and 39, SEQ ID NO: 45 and 46, SEQ ID NO: 53 and 54, or SEQ ID NO: 61 and 62, respectively. Such antibodies can be identified using routine competition binding assays including, for example, surface plasmon resonance (SPR)-based competition assays.

Figure 17:
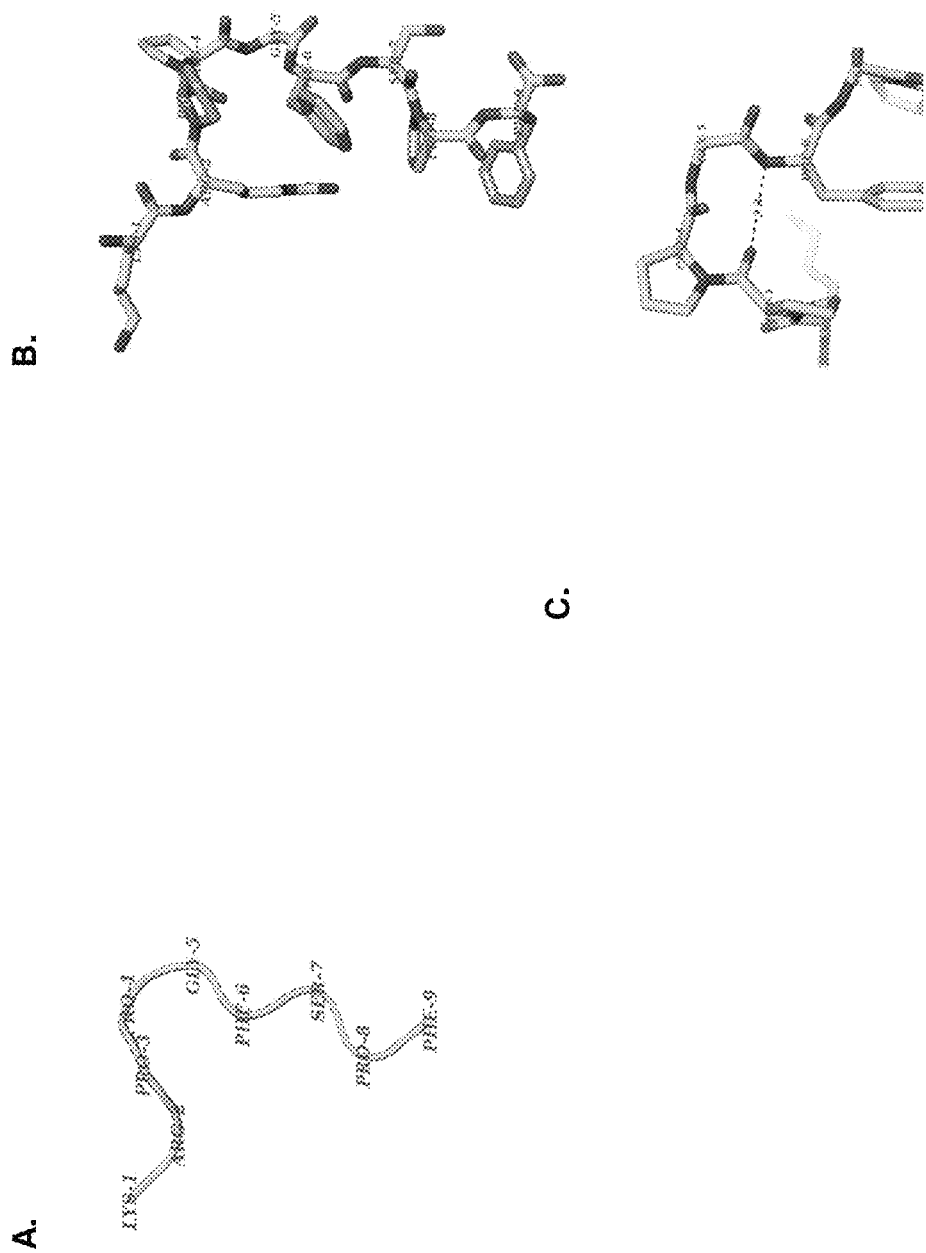
FIG. 17 depicts (A) the secondary and (B) tertiary structure of the main chain polypeptide backbone conformation of kallidin (KD) as bound to F151 antibody which comprises a type II tight turn at Proline 4 (C). Figure discloses SEQ ID NOS 2, 2, and 133, respectively, in order of appearance.

In certain embodiments, the antibodies of the invention bind a conformational epitope of Kallidin (KD) or des-Arg10-Kallidin (DAKD) which adopts a "Pro4 kink" conformation. As depicted in FIG. 17, a hallmark of the "Pro4 kink" conformation is a type II tight turn in the main chain polypeptide backbone of KD or DAKD at Proline 4. As known to those of skill in the art, a type II tight turn conformation comprises three residues (X1-X2-X3) with the carbonyl of residue Xl forming a hydrogen bond with the amide N of residue X3, which is typically a glycine (see Richardson J S. "The anatomy and taxonomy of protein structure." Adv Protein Chem. 1981; 34:167-339, which is incorporated by reference herein). Accordingly, in certain embodiments, a type II tight turn conformation is formed by the Pro3-Pro4-Gly5 motif of KD or DADK. In more specific embodiments, the "Pro4 kink" conformation is further defined by all or substantially all of the remaining amino acids of KD (1-2 and 6-9) or DAKD adopting repeats of a sigmoid shape which align the hydrophobic side chains in a spatially stacking mode.

III. Modified Anti-Kallidin or des-Arg$_{10}$-Kallidin Antibodies

In certain embodiments, anti-Kallidin or des-Arg10-Kallidin antibodies of the invention may comprise one or more modifications. Modified forms of anti-Kallidin or des-Arg10-Kallidin antibodies of the invention can be made using any techniques known in the art.

i) Reducing Immunogenicity

In certain embodiments, anti-Kallidin or des-Arg10-Kallidin antibodies, or antigen binding fragments thereof, of the invention are modified to reduce their immunogenicity using art-recognized techniques. For example, antibodies, or fragments thereof, can be chimericized, humanized, and/or deimmunized.

In one embodiment, an antibody, or antigen binding fragments thereof, of the invention may be chimeric. A chimeric antibody is an antibody in which different portions of the antibody are derived from different animal species, such as antibodies having a variable region derived from a murine monoclonal antibody and a human immunoglobulin constant region. Methods for producing chimeric antibodies, or fragments thereof, are known in the art. See, e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397, which are incorporated herein by reference in their entireties. Techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) may be employed for the synthesis of said molecules. For example, a genetic sequence encoding a binding specificity of a mouse anti-Kallidin or des-Arg10-Kallidin antibody molecule may be fused together with a sequence from a human antibody molecule of appropriate biological activity. As used herein, a chimeric antibody is a molecule in which different portions are derived from different animal species, such as those having a variable region derived from a murine monoclonal antibody and a human immunoglobulin constant region, e.g., humanized antibodies.

In another embodiment, an antibody, or antigen binding fragment thereof, of the invention is humanized. Humanized antibodies, have a binding specificity comprising one or more complementarity determining regions (CDRs) from a non-human antibody and framework regions from a human antibody molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585, 089), veneering or resurfacing (EP 592,106; EP 519,596; Padlan, Molecular Immunology 28(4/5):489-498 (1991);

Studnicka et al., Protein Engineering 7(6):805-814 (1994); Roguska. et al., PNAS 91:969-973 (1994)), and chain shuffling (U.S. Pat. No. 5,565,332).

In a particular embodiment, a humanization method is employed that is based on the impact of the molecular flexibility of the antibody during and at immune recognition (see WO2009/032661, which is incorporated herein by reference in its entirety). Protein flexibility is related to the molecular motion of the protein molecule. Protein flexibility is the ability of a whole protein, a part of a protein or a single amino acid residue to adopt an ensemble of conformations which differ significantly from each other. Information about protein flexibility can be obtained by performing protein X-ray crystallography experiments (see, for example, Kundu et al. 2002, Biophys J 83:723-732.), nuclear magnetic resonance experiments (see, for example, Freedberg et al., J Am Chem Soc 1998, 120(31):7916-7923) or by running molecular dynamics (MD) simulations. An MD simulation of a protein is done on a computer and allows one to determine the motion of all protein atoms over a period of time by calculating the physical interactions of the atoms with each other. The output of a MD simulation is the trajectory of the studied protein over the period of time of the simulation. The trajectory is an ensemble of protein conformations, also called snapshots, which are periodically sampled over the period of the simulation, e.g. every 1 picosecond (ps). It is by analyzing the ensemble of snapshots that one can quantify the flexibility of the protein amino acid residues. Thus, a flexible residue is one which adopts an ensemble of different conformations in the context of the polypeptide within which that residue resides. MD methods are known in the art, see, e.g., Brooks et al. "Proteins: A Theoretical Perspective of Dynamics, Structure and Thermodynamics" (Wiley, New York, 1988). Several software enable MD simulations, such as Amber (see Case et al. (2005) J Comp Chem 26:1668-1688), Charmm (see Brooks et al. (1983) J Comp Chem 4:187-217; and MacKerell et al. (1998) in "The Encyclopedia of Computational Chemistry" vol. 1:271-177, Schleyer et al., eds. Chichester: John Wiley & Sons) or Impact (see Rizzo et al. J Am Chem Soc; 2000; 122(51):12898-12900.)

Most protein complexes share a relatively large and planar buried surface and it has been shown that flexibility of binding partners provides the origin for their plasticity, enabling them to conformationally adapt to each other (Structure (2000) 8, R137-R142). As such, examples of "induced fit" have been shown to play a dominant role in protein-protein interfaces. In addition, there is a steadily increasing body of data showing that proteins actually bind ligands of diverse shapes sizes and composition (Protein Science (2002) 11:184-187) and that the conformational diversity appears to be an essential component of the ability to recognize different partners (Science (2003) 299, 1362-1367). Flexible residues are involved in the binding of protein-protein partners (Structure (2006) 14, 683-693).

The flexible residues can adopt a variety of conformations that provide an ensemble of interaction areas that are likely to be recognized by memory B cells and to trigger an immunogenic response. Thus, an antibody can be humanized by modifying a number of residues from the framework so that the ensemble of conformations and of recognition areas displayed by the modified antibody resemble as much as possible those adopted by a human antibody. That can be achieved by modifying a limited number of residues by: (1) building a homology model of the parent mAb and running an MD simulation; (2) analyzing the flexible residues and identification of the most flexible residues of a non-human antibody molecule, as well as identifying residues or motifs likely to be a source of heterogeneity or of degradation reaction; (3) identifying a human antibody which displays the most similar ensemble of recognition areas as the parent antibody; (4) determining the flexible residues to be mutated, residues or motifs likely to be a source of heterogeneity and degradation are also mutated; and (5) checking for the presence of known T cell or B cell epitopes. The flexible residues can be found using an MD calculation as taught herein using an implicit solvent model, which accounts for the interaction of the water solvent with the protein atoms over the period of time of the simulation.

Once the set of flexible residues has been identified within the variable light and heavy chains, a set of human heavy and light chain variable region frameworks that closely resemble that of the antibody of interest are identified. That can be done, for example, using a BLAST search on the set of flexible residues against a database of antibody human germ line sequence. It can also be done by comparing the dynamics of the parent mAb with the dynamics of a library of germ line canonical structures. The CDR residues and neighboring residues are excluded from the search to ensure high affinity for the antigen is preserved. Flexible residues then are replaced.

When several human residues show similar homologies, the selection is driven also by the nature of the residues that are likely to affect the solution behavior of the humanized antibody. For instance, polar residues will be preferred in exposed flexible loops over hydrophobic residues. Residues which are a potential source of instability and heterogeneity are also mutated even if there are found in the CDRs. That will include exposed methionines as sulfoxide formation can result from oxygen radicals, proteolytic cleavage of acid labile bonds such as those of the Asp-Pro dipeptide (Drug Dev Res (2004) 61:137-154), deamidation sites found with an exposed asparagine residue followed by a small amino acid, such as Gly, Ser, Ala, H is, Asn or Cys (J Chromatog (2006) 837:35-43) and N-glycosylation sites, such as the Asn-X-Ser/Thr site. Typically, exposed methionines will be substituted by a Leu, exposed asparagines will be replaced by a glutamine or by an aspartate, or the subsequent residue will be changed. For the glycosylation site (Asn-X-Ser/Thr), either the Asn or the Ser/Thr residue will be changed.

The resulting composite antibody sequence is checked for the presence of known B cell or linear T-cell epitopes. A search is performed, for example, with the publicly available Immune Epitope Data Base (IEDB) (PLos Biol (2005) 3(3)e91). If a known epitope is found within the composite sequence, another set of human sequences is retrieved and substituted. Thus, unlike the resurfacing method of U.S. Pat. No. 5,639,641, both B-cell-mediated and T-cell-mediated immunogenic responses are addressed by the method. The method also avoids the issue of loss of activity that is sometimes observed with CDR grafting (U.S. Pat. No. 5,530,101). In addition, stability and solubility issues also are considered in the engineering and selection process, resulting in an antibody that is optimized for low immunogenicity, high antigen affinity and improved biophysical properties.

In some embodiments, de-immunization can be used to decrease the immunogenicity of and antibody, or antigen binding fragment thereof. As used herein, the term "de-immunization" includes alteration of an antibody, or antigen binding fragment thereof, to modify T cell epitopes (see, e.g., WO9852976A1, WO0034317A2). For example, VH and VL sequences from the starting antibody may be analyzed and a human T cell epitope "map" may be generated from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of Kallidin or des-Arg10-Kallidin-specific antibodies or fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

ii) Effector Functions and Fc Modifications

Anti-Kallidin or des-Arg10-Kallidin antibodies of the invention may comprise an antibody constant region (e.g. an IgG constant region e.g., a human IgG constant region, e.g., a human IgG1 or IgG4 constant region) which mediates one or more effector functions. For example, binding of the C1 component of complement to an antibody constant region may activate the complement system. Activation of complement is important in the opsonisation and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. In preferred embodiments, the antibodies, or fragments thereof, of the invention bind to an Fc-gamma receptor. In alternative embodiments, anti-Kallidin or des-Arg10-Kallidin antibodies of the invention may comprise a constant region which is devoid of one or more effector functions (e.g., ADCC activity) and/or is unable to bind Fc□ receptor.

Certain embodiments of the invention include anti-Kallidin or des-Arg10-Kallidin antibodies in which at least one amino acid in one or more of the constant region domains has been deleted or otherwise altered so as to provide desired biochemical characteristics such as reduced or enhanced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies, or fragments thereof, for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain other embodiments, anti-Kallidin or des-Arg10-Kallidin antibodies comprise constant regions derived from different antibody isotypes (e.g., constant regions from two or more of a human IgG1, IgG2, IgG3, or IgG4). In other embodiments, anti-Kallidin or des-Arg10-Kallidin antibodies comprises a chimeric hinge (i.e., a hinge comprising hinge portions derived from hinge domains of different antibody isotypes, e.g., an upper hinge domain from an IgG4 molecule and an IgG1 middle hinge domain). In one embodiment, an anti-Kallidin or des-Arg10-Kallidin antibodies comprises an Fc region or portion thereof from a human IgG4 molecule and a Ser228Pro mutation (EU numbering) in the core hinge region of the molecule.

In certain anti-Kallidin or des-Arg10-Kallidin antibodies, the Fc portion may be mutated to increase or decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or flexibility. The resulting physiological profile, bioavailability and other biochemical effects of the modifications, such as tumor localization, biodistribution and serum half-life, may easily be measured and quantified using well know immunological techniques without undue experimentation.

In certain embodiments, an Fc domain employed in an antibody of the invention is an Fc variant. As used herein, the term "Fc variant" refers to an Fc domain having at least one amino acid substitution relative to the wild-type Fc domain from which said Fc domain is derived. For example, wherein the Fc domain is derived from a human IgG1 antibody, the Fc variant of said human IgG1 Fc domain comprises at least one amino acid substitution relative to said Fc domain.

The amino acid substitution(s) of an Fc variant may be located at any position (i.e., any EU convention amino acid position) within the Fc domain. In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

The antibodies of the invention may employ any art-recognized Fc variant which is known to impart an improvement (e.g., reduction or enhancement) in effector function and/or FcR binding. Said Fc variants may include, for example, any one of the amino acid substitutions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO05/

070963A1, WO05/077981A2, WO05/092925A2, WO05/123780A2, WO06/019447A1, WO06/047350A2, and WO06/085967A2 or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784, each of which is incorporated by reference herein. In one exemplary embodiment, an antibody of the invention may comprise an Fc variant comprising an amino acid substitution at EU position 268 (e.g., H268D or H268E). In another exemplary embodiment, an antibody of the invention may comprise an amino acid substitution at EU position 239 (e.g., S239D or S239E) and/or EU position 332 (e.g., I332D or I332Q).

In certain embodiments, an antibody of the invention may comprise an Fc variant comprising an amino acid substitution which alters the antigen-independent effector functions of the antibody, in particular the circulating half-life of the antibody. Such antibodies exhibit either increased or decreased binding to FcRn when compared to antibodies lacking these substitutions, therefore, have an increased or decreased half-life in serum, respectively. Fc variants with improved affinity for FcRn are anticipated to have longer serum half-lives, and such molecules have useful applications in methods of treating mammals where long half-life of the administered antibody is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the altered antibodies of the invention exhibit reduced transport across the epithelium of kidney glomeruli from the vasculature. In another embodiment, the altered antibodies of the invention exhibit reduced transport across the blood brain barrier (BBB) from the brain, into the vascular space. In one embodiment, an antibody with altered FcRn binding comprises an Fc domain having one or more amino acid substitutions within the "FcRn binding loop" of an Fc domain. The FcRn binding loop is comprised of amino acid residues 280-299 (according to EU numbering). Exemplary amino acid substitutions which altered FcRn binding activity are disclosed in International PCT Publication No. WO05/047327 which is incorporated by reference herein. In certain exemplary embodiments, the antibodies, or fragments thereof, of the invention comprise an Fc domain having one or more of the following substitutions: V284E, H285E, N286D, K290E and S304D (EU numbering).

In other embodiments, antibodies, for use in the diagnostic and treatment methods described herein have a constant region, e.g., an IgG1 or IgG4 heavy chain constant region, which is altered to reduce or eliminate glycosylation. For example, an antibody of the invention may also comprise an Fc variant comprising an amino acid substitution which alters the glycosylation of the antibody. For example, said Fc variant may have reduced glycosylation (e.g., N- or O-linked glycosylation). In exemplary embodiments, the Fc variant comprises reduced glycosylation of the N-linked glycan normally found at amino acid position 297 (EU numbering). In another embodiment, the antibody has an amino acid substitution near or within a glycosylation motif, for example, an N-linked glycosylation motif that contains the amino acid sequence NXT or NXS. In a particular embodiment, the antibody comprises an Fc variant with an amino acid substitution at amino acid position 228 or 299 (EU numbering). In more particular embodiments, the antibody comprises an IgG1 or IgG4 constant region comprising an S228P and a T299A mutation (EU numbering).

Exemplary amino acid substitutions which confer reduce or altered glycosylation are disclosed in International PCT Publication No. WO05/018572, which is incorporated by reference herein. In preferred embodiments, the antibodies, or fragments thereof, of the invention are modified to eliminate glycosylation. Such antibodies, or fragments thereof, may be referred to as "agly" antibodies, or fragments thereof, (e.g. "agly" antibodies). While not being bound by theory, it is believed that "agly" antibodies, or fragments thereof, may have an improved safety and stability profile in vivo. Exemplary agly antibodies, or fragments thereof, comprise an aglycosylated Fc region of an IgG4 antibody which is devoid of Fc-effector function thereby eliminating the potential for Fc mediated toxicity to the normal vital organs that express Kallidin or des-Arg10-Kallidin. In yet other embodiments, antibodies, or fragments thereof, of the invention comprise an altered glycan. For example, the antibody may have a reduced number of fucose residues on an N-glycan at Asn297 of the Fc region, i.e., is afucosylated. In another embodiment, the antibody may have an altered number of sialic acid residues on the N-glycan at Asn297 of the Fc region.

iii) Covalent Attachment

Anti-Kallidin or des-Arg10-Kallidin antibodies of the invention may be modified, e.g., by the covalent attachment of a molecule to the antibody such that covalent attachment does not prevent the antibody from specifically binding to its cognate epitope. For example, but not by way of limitation, the antibodies, or fragments thereof, of the invention may be modified by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

Antibodies, or fragments thereof, of the invention may further be recombinantly fused to a heterologous polypeptide at the N- or C-terminus or chemically conjugated (including covalent and non-covalent conjugations) to polypeptides or other compositions. For example, anti-Kallidin or des-Arg10-Kallidin antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Anti-Kallidin or des-Arg10-Kallidin antibodies may be fused to heterologous polypeptides to increase the in vivo half life or for use in immunoassays using methods known in the art. For example, in one embodiment, PEG can be conjugated to the anti-Kallidin or des-Arg10-Kallidin antibodies of the invention to increase their half-life in vivo. Leong, S. R., et al., Cytokine 16:106 (2001); Adv. in Drug Deliv. Rev. 54:531 (2002); or Weir et al., Biochem. Soc. Transactions 30:512 (2002).

Moreover, anti-Kallidin or des-Arg10-Kallidin antibodies of the invention can be fused to marker sequences, such as a peptide to facilitate their purification or detection. In preferred embodiments, the marker amino acid sequence is a hexa-histidine peptide (SEQ ID NO: 137), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine (SEQ ID NO: 137) provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Anti-Kallidin or des-Arg10-Kallidin antibodies of the invention may be used in non-conjugated form or may be conjugated to at least one of a variety of molecules, e.g., to improve the therapeutic properties of the molecule, to facilitate target detection, or for imaging or therapy of the patient. Anti-Kallidin or des-Arg10-Kallidin antibodies of the invention can be labeled or conjugated either before or after purification, when purification is performed. In particular, anti-Kallidin or des-Arg10-Kallidin antibodies of the invention may be conjugated to therapeutic agents, prodrugs, peptides, proteins, enzymes, viruses, lipids, biological response modifiers, pharmaceutical agents, or PEG.

The present invention further encompasses anti-Kallidin or des-Arg10-Kallidin antibodies of the invention conjugated to a diagnostic or therapeutic agent. The anti-Kallidin or des-Arg10-Kallidin antibodies can be used diagnostically to, for example, monitor the development or progression of a immune cell disorder (e.g., CLL) as part of a clinical testing procedure to, e.g., determine the efficacy of a given treatment and/or prevention regimen. Detection can be facilitated by coupling the anti-Kallidin or des-Arg10-Kallidin antibodies to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, .beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Anti-Kallidin or des-Arg10-Kallidin antibodies for use in the diagnostic and treatment methods disclosed herein may be conjugated to cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), or PEG.

In another embodiment, an anti-Kallidin or des-Arg10-Kallidin antibody for use in the diagnostic and treatment methods disclosed herein can be conjugated to a molecule that decreases tumor cell growth. In other embodiments, the disclosed compositions may comprise antibodies, or fragments thereof, coupled to drugs or prodrugs. Still other embodiments of the present invention comprise the use of antibodies, or fragments thereof, conjugated to specific biotoxins or their cytotoxic fragments such as ricin, gelonin, *Pseudomonas* exotoxin or diphtheria toxin. The selection of which conjugated or unconjugated antibody to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that, in previous studies, anti-tumor antibodies labeled with isotopes have been used successfully to destroy tumor cells in animal models, and in some cases in humans. Exemplary radioisotopes include: 90Y, 125I, 131I, 123I, 111In, 105Rh, 153Sm, 67Cu, 67Ga, 166Ho, 177Lu, 186Re and 188Re. The radionuclides act by producing ionizing radiation which causes multiple strand breaks in nuclear DNA, leading to cell death. The isotopes used to produce therapeutic conjugates typically produce high energy alpha- or beta-particles which have a short path length. Such radionuclides kill cells to which they are in close proximity, for example neoplastic cells to which the conjugate has attached or has entered. They have little or no effect on non-localized cells. Radionuclides are essentially non-immunogenic.

IV. Expression of Anti-Kallidin or des-Arg10-Kallidin Antibodies, or Antigen Binding Fragments Thereof Following manipulation of the isolated genetic material to provide anti-Kallidin or des-Arg10-Kallidin antibodies of the invention as set forth above, the genes are typically inserted in an expression vector for introduction into host cells that may be used to produce the desired quantity of the claimed antibodies, or fragments thereof.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems may be employed for the purposes of this invention. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals. In particularly preferred embodiments the cloned variable region genes are inserted into an expression vector along with the heavy and light chain constant region genes (preferably human) synthetic as discussed above.

In other preferred embodiments the anti-Kallidin or des-Arg10-Kallidin antibodies, or fragments thereof, of the invention may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980, which is incorporated by reference herein. Those skilled in the art will appreciate that such expression systems may be used to effectively produce the full range of polypeptides disclosed in the instant application.

More generally, once a vector or DNA sequence encoding an antibody, or fragment thereof, has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

In one embodiment, the host cell line used for antibody expression is of mammalian origin; those skilled in the art can determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), BFA-1c1BPT (bovine endothelial cells), RAJI (human lymphocyte), 293 (human kidney). In one embodiment, the cell line provides for altered glycosylation, e.g., afucosylation, of the antibodyexpressed therefrom (e.g., PER.C6® (Crucell) or FUT8-knock-out CHO cell lines (Potelligent® Cells) (Biowa, Princeton, N.J.)). In one embodiment NSO cells may be used. CHO cells are particularly preferred. Host cell lines are typically available from commercial services, the American Tissue Culture Collection or from published literature.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-)affinity chromatography.

Genes encoding the anti-Kallidin or des-Arg10-Kallidin antibodies, or fragments thereof, of the invention can also be expressed non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides can become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan.

V. Pharmaceutical Formulations and Methods of Administration of Anti-Kallidin or des-Arg10-Kallidin Antibodies In another aspect, the invention provides pharmaceutical compositions comprising an anti-Kallidin or des-Arg10-Kallidin antibody, or fragment thereof.

Methods of preparing and administering antibodies, or fragments thereof, of the invention to a subject are well known to or are readily determined by those skilled in the art. The route of administration of the antibodies, or fragments thereof, of the invention may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1 M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an antibody by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338 each of which is incorporated herein by reference. Such articles of manufacture will preferably have labels or package inserts indicating that the associated compositions are useful for treating a subject suffering from, or predisposed to autoimmune or neoplastic disorders.

Effective doses of the stabilized antibodies, or fragments thereof, of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

For passive immunization with an antibody of the invention, the dosage may range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention.

Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered may fall within the ranges indicated.

Antibodies, or fragments thereof, of the invention can be administered on multiple occasions. Intervals between single dosages can be, e.g., daily, weekly, monthly or yearly. Intervals can also be irregular as indicated by measuring blood levels of polypeptide or target molecule in the patient. In some methods, dosage is adjusted to achieve a certain plasma antibody or toxin concentration, e.g., 1-1000 ug/ml or 25-300 ug/ml. Alternatively, antibodies, or fragments thereof, can be administered as a sustained release formulation, in which case less frequent administration is required. Dosage and frequency vary depending on the half-life of the antibody in the patient. In general, humanized antibodies show the longest half-life, followed by chimeric antibodies and nonhuman antibodies. In one embodiment, the antibodies, or fragments thereof, of the invention can be administered in unconjugated form. In another embodiment, the antibodies of the invention can be administered multiple times in conjugated form. In still another embodiment, the antibodies, or fragments thereof, of the invention can be administered in unconjugated form, then in conjugated form, or vise versa.

The dosage and frequency of administration can vary depending on whether the treatment is prophylactic or therapeutic. In prophylactic applications, compositions containing the present antibodies or a cocktail thereof are administered to a patient not already in the disease state to enhance the patients resistance. Such an amount is defined to be a "prophylactic effective dose." In this use, the precise amounts again depend upon the patients state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding a polypeptide of the invention (e.g., in a vector). Doses for nucleic acids encoding polypeptides range from about 10 ng to 1 g, 100 ng to 100 mg, 1 ug to 10 mg, or 30-300 ug DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. Intramuscular injection or intravenous infusion are preferred for administration of a antibody of the invention. In some methods, therapeutic antibodies, or fragments thereof, are injected directly into the cranium. In some methods, antibodies, or fragments thereof, are administered as a sustained release composition or device, such as a Medipad™ device.

Agents of the invention can optionally be administered in combination with other agents that are effective in treating the disorder or condition in need of treatment (e.g., prophylactic or therapeutic). Preferred additional agents are those which are art recognized and are standardly administered for a particular disorder.

Effective single treatment dosages (i.e., therapeutically effective amounts) of 90Y-labeled antibodies of the invention range from between about 5 and about 75 mCi, more preferably between about 10 and about 40 mCi. Effective single treatment non-marrow ablative dosages of 131I-labeled antibodies range from between about 5 and about 70 mCi, more preferably between about 5 and about 40 mCi. Effective single treatment ablative dosages (i.e., may require autologous bone marrow transplantation) of 131I-labeled antibodies range from between about 30 and about 600 mCi, more preferably between about 50 and less than about 500 mCi. In conjunction with a chimeric modified antibody, owing to the longer circulating half life vis-a-vis murine antibodies, an effective single treatment non-marrow ablative dosages of iodine-131 labeled chimeric antibodies range from between about 5 and about 40 mCi, more preferably less than about 30 mCi. Imaging criteria for, e.g., the 111In label, are typically less than about 5 mCi.

While a great deal of clinical experience has been gained with 131I and 0.90Y, other radiolabels are known in the art and have been used for similar purposes. Still other radioisotopes are used for imaging. For example, additional radioisotopes which are compatible with the scope of the instant invention include, but are not limited to, 123I, 125I, 32P, 57Co, 64Cu, 67Cu, 77Br, 81Rb, 81Kr, 87Sr, 113In, 127Cs, 129Cs, 132I, 197Hg, 203Pb, 206Bi, 177Lu, 186Re, 212Pb, 212Bi, 47Sc, 105Rh, 109Pd, 153Sm, 188Re, 199Au, 225Ac, 211A 213Bi. In this respect alpha, gamma and beta emitters are all compatible with in the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include 125I, 123I, 99Tc, 43K, 52Fe, 67Ga, 68Ga, as well as 111In. Antibodies have also been labeled with a variety of radionuclides for potential use in targeted immunotherapy (Peirersz et al. Immunol. Cell Biol. 65: 111-125 (1987)). These radionuclides include 188Re and 186Re as well as 199Au and 67Cu to a lesser extent. U.S. Pat. No. 5,460,785 provides additional data regarding such radioisotopes and is incorporated herein by reference.

As previously discussed, the antibodies, or fragments thereof, of the invention, can be administered in a pharmaceutically effective amount for the in vivo treatment of mammalian disorders. In this regard, it will be appreciated that the disclosed antibodies, or fragments thereof, will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of a antibody of the invention, conjugated or unconjugated to a therapeutic agent, shall be held to mean an amount sufficient to achieve effective binding to a target and to achieve a benefit, e.g., to ameliorate symptoms of a disease or disorder or to detect a substance or a cell. In the case of tumor cells, the polypeptide will be preferably capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the polypeptide.

In keeping with the scope of the present disclosure, the antibodies of the invention may be administered to a human or other animal in accordance with the aforementioned methods of treatment in an amount sufficient to produce a therapeutic or prophylactic effect. The polypeptides of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of polypeptides according to the present invention may prove to be particularly effective.

VI. Methods of Treating Kallidin or des-Arg10-Kallidin-Associated Disease or Disorders The anti-Kallidin or des-Arg10-Kallidin antibodies, or fragments thereof, of the invention are useful for antagonizing Kallidin or des-Arg10-Kallidin activity. Accordingly, in another aspect, the invention provides methods for treating Kallidin or des-Arg10-Kallidin-associated diseases or disorders by administering to a subject in need of thereof a pharmaceutical composition comprising one or more anti-Kallidin or des-Arg10-Kallidin antibody, or antigen binding fragment thereof of the invention.

Kallidin or des-Arg10-Kallidin-associated diseases or disorders amenable to treatment include, without limitation, pathophysiologic conditions such as inflammation, trauma, burns, shock, allergy, acute or chronic pain, and fibrosis, e.g., renal fibrosis. In certain exemplary, embodiments, antibodies of the invention may be issued to treat renal fibrosis and associated acute kidney injury as well as chronic kidney diseases which are the main causes of end-stage renal failure.

One skilled in the art would be able, by routine experimentation, to determine what an effective, non-toxic amount of antibody (or additional therapeutic agent) would be for the purpose of treating a Kallidin or des-Arg10-Kallidin-associated disease or disorder. For example, a therapeutically active amount of a polypeptide may vary according to factors such as the disease stage (e.g., stage I versus stage IV), age, sex, medical complications (e.g., immunosuppressed conditions or diseases) and weight of the subject, and the ability of the antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10, milligrams per kilogram body weight per day.

VII. Exemplification

The present invention is further illustrated by the following examples which should not be construed as further limiting. The contents of Sequence Listing, figures and all references, patents and published patent applications cited throughout this application are expressly incorporated herein by reference.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Example 1: Hybridoma Production: Immunization of Mice with Kallidin Peptide Conjugated to KLH and Antibody Generation against Human BKR1 Ligands The objective was to develop cross-reactive antibodies against Kallidin (KD; SEQ ID NO:1) and des-arg-Kallidin (DAKD; SEQ ID NO:2) that would inhibit these ligands binding to the human BKR1. Generally, immunization of mice with KLH conjugated KD through additional cysteines on either the C- or N-terminus of the peptide was used to obtain mouse splenocytes for fusion with mouse myeloma cell lines as a fusion partner to produce the hybridomas.

Briefly, the immunization protocol was as follows: BALB/c Mice (8-20 week-old naïve female) were immunized intraperitoneally with a mixture of even amounts of KLH-KD and KD-KLH in phosphate buffered saline (PBS) as an antigen total of 100 ug per mouse mixed at 1:1 ratio of Sigma Adjuvant System (Sigma cat #6322) in a total volume of 200 µl per mouse (day 0). On day 21, mice were boosted with a mixture of even amounts of KLH-KD and KD-KLH in PBS as an antigen total of 50 ug per mouse mixed at 1:1 ratio of Sigma Adjuvant System (Sigma cat #6322) in a total volume of 200 µl per mouse. On day 30, blood samples were harvested for KD specific antibody titer evaluation. On day 51, mice were boosted for fusion with a mixture of even amounts of KLH-KD and KD-KLH in PBS as an antigen total of 50 ug per mouse mixed at 1:1 ratio of Sigma Adjuvant System (Sigma cat #6322) in a total volume of 200 µl per mouse. At day 55 mice were sacrificed by CO2 chamber, blood was collected through the cardiac puncture and spleen was harvested for hybridoma production.

Hybridomas were made by fusing mouse myeloma cells that are deficient in adenosine phosphoribosyltransferase (APRT) with spleen cells from mice immunized with specific antigens. A selection system using HAT (hypoxanthine, azaserine, and thymidine) medium eliminates all but the fusion cells that are APRT+. Successful hybridomas must also retain the immunoglobulin (Igh) heavy chain, one of the immunoglobulin light chain loci and secrete functional antibody.

Hybridoma Production Medium (IMDM) was made by combining the following: 500 ml Iscove's Modified Dulbecco's Medium (HyClone SH30259.01), 50 ml fetal bovine serum (HyClone SH30070.03), 5 ml L-glutamine (Gibco Invitrogen cat #25030), 5 ml non-essential amino acids (Gibco Invitrogen cat #11140050), 5 ml sodium pyruvate (Gibco Invitrogen cat #11360070), 5 ml 0.1% penicillin-streptomycin (Gibco Invitrogen cat #15140148). The medium was filtered before use. Expansion medium was made by combining the following: 1000 ml serum free medium (Gibco Hybridoma SFM #12045), 100 ml 10% HyClone SuperLow IgG Defined FBS # SH30898.03 and 10 ml penicillin/streptomycin. Freezing medium was 45 ml heat inactivated FBS (HyClone SH30070.03) and 5 ml DMSO, filter sterilized. Other materials included the following: HAT (50×) was obtained from Sigma-Aldrich (# H0262); Hybridoma Fusion and Cloning Supplement (50×) (Roche Diagnostics 11 363 735 001); Trypan Blue Stain 0.4% (Invitrogen cat #15250-061 or T10282); PEG 1500 in 75 mM Hepes 50% w/v (Roche cat #783641(10783641001). All the reagents except HAT and Hybridoma Fusion and cloning supplement were used at 37° C.

TABLE 2

Peptide Reagents Used in Immunization and Screening

| Peptide No. | SEQ ID NO. | Peptide Sequence | Peptide Name | Alternative Name |
|---|---|---|---|---|
| 1 | 5 | RPPGFSPFR | bradykinin | BK |
| 2 | 117 | biotin-RPPGFSPFR | | b-BK |
| 3 | 71 | RPPGFSPFR-biotin | | BK-b |
| 4 | 72 | KLH-RPPGFSPFR | | KLH-BK |
| 5 | 73 | RPPGFSPFR-KLH | | BK-KLH |
| 6 | 1 | KRPPGFSPFR | kallidin | KD |
| 7 | 74 | biotin-KRPPGFSPFR | | b-KD |
| 8 | 75 | KRPPGFSPFR-biotin | | KD-b |
| 9 | 76 | KLH-KRPPGFSPFR | | KLH-KD |
| 10 | 77 | KRPPGFSPFR-KLH | | KD-KLH |
| 11 | 6 | RPPGFSPF | desArg9bradykinin | DABK |
| 12 | 78 | biotin-RPPGFSPF | | b-DABK |
| 13 | 79 | RPPGFSPF-biotin | | DABK-b |
| 14 | 80 | KLH-RPPGFSPF | | KLHDABK |
| 15 | 81 | RPPGFSPF-KLH | | DABK-KLH |
| 16 | 2 | KRPPGFSPF | desArg10kallidin | DAKD |
| 17 | 82 | biotin-KRPPGFSPF | | b-DAKD |
| 18 | 83 | KRPPGFSPF-biotin | | DAKD-b |
| 19 | 84 | KLH-KRPPGFSPF | | KLH-DAKD |
| 20 | 85 | KRPPGFSPF-KLH | | DAKD-KLH |
| 21 | 3 | RRPPGFSPFR | Kallidin like peptide | KLP |
| 22 | 86 | biotin-RRPPGFSPFR | | b-KLP |
| 23 | 87 | RRPPGFSPFR-biotin | | KLP-b |
| 24 | 88 | KLH-RRPPGFSPFR | | KLH-KLP |
| 25 | 89 | RRPPGFSPFR-KLH | | KLP-KLH |
| 26 | 90 | RRPPGFSPF | desArg10kallidin like peptide | DAKLP |
| 27 | 91 | biotin-RRPPGFSPF | | b-DAKLP |
| 28 | 92 | RRPPGFSPF-biotin | | DAKLP-b |
| 29 | 93 | KLH-RRPPGFSPF | | KLH-DAKLP |
| 30 | 94 | RRPPGFSPF-KLH | | DAKLP-b |
| 31 | 95 | RPPGF | bradykinin1-5 | BK15 |
| 32 | 96 | biotin-RPPGF | | b-BK15 |

Briefly, three or four days before the fusion, the mouse was boosted with an antigen of interest either intraperitonealy or intravenously. On the day of the fusion, the mouse was sacrificed in CO$_2$ chamber, blood was collected by cardiac puncture and the spleen was taken out and placed into 10 ml of serum free IMDM in a Petri dish. Fusion partner cells myeloma: FO (ATCC ref CRL-1646)/X63 Ag8.653 (ATCC ref CRL1580) were grown at a log phase, then split one day before the fusion (1:2 and 1:5), and collected into 20 ml centrifuge tubes, spun and resuspended the pellet in 10 ml IMDM. The pellet was washed two times with serum free IMDM medium. All the centrifugations are performed at 1570 rpm for 5 min. Final resuspension was in 10 ml serum free IMDM. The connective tissue was dissected away from the spleen. The spleen was injected with 1 ml of serum free IMDM preheated to 37° C. by 1 ml syringe and 25-gauge needle. Splenocytes are squeezed out of the fibroelastic coat by forceps and washed two times in 10 ml of serum free IMDM (including initial spin) and were resuspended in 10 ml serum free IMDM. Cells were counted in Countess Automated Cell Counter.

Fusion partner cells and splenocytes were combined in one 50 ml tube at ratio of 1:2 to 1:10 (by cell number) and spun down at 970 rpm for 10 min (slow spin) to form a loose pellet. After the "slow" spin, supernatant was taken out with the precaution not to disturb the pellet, but minimize the amount of liquid over the cells in order not to dilute PEG 1500. The last remaining medium was reserved and added back after the PEG is added (below). Preheated PEG 1500 (37° C., total 1 ml) was added drop by drop to the cell pellet over 1 minute period of time and cells were mixed after every drop of PEG was added. Pellet was incubated with PEG for another 1 minute followed by addition of 10 ml of serum-free IMDM medium over 1 minute, so that the first 1 ml out of 10 is added over 30 sec. Cells underwent slow spin at 970 rpm for 10 min and supernatant decanted. Into (2) 100 ml troughs, the following was added: 70 ml IMDM with 10% FBS, 2 ml HAT and 2 ml Hybridoma and Fusion Cloning Supplement. Cells were resuspended in 10 ml IMDM with 10% FBS and split into (2) 50 ml tubes (5 ml cells/tube) and 25 ml IMDM with 10% FBS was added. The resulting 30 ml was transferred to the troughs containing 70 ml HBSS/HAT/cloning supplement and 200 ul cells/well were pipetted into (10) 96-well plates. Fusion was ready for screening by ELISA (50 ul) about 10 to 14 days later, or when medium in the wells turns yellow. After the primary screening, positive clones are selected, numbered and moved to a 24-well plate in 500 ul per well of IMDM with 10% FBSHI. Hybridoma supernatants were screened by ELISA on streptavidin plated coated with N- and C-term biotinylated peptides (see below).

Example 2: Characterization and Selection of Hybridomas Expressing Antibodies Against Human BKR1 Ligands Hybridoma supernatants were screened by ELISA on streptavidin plated coated with N- and C-term biotinylated peptides (see e.g., those set forth in Table 2) and then antibody binding kinetics were determined for confirmed positive hybridoma clones.

The ability of the antibodies in hybridoma supernatants to bind to BKR1 ligand peptide was evaluated with an ELISA assay. DAKD-biotin or KD-biotin peptides was coated on a 96-well SA plate in phosphate buffered saline (PBS) buffer for an hour at room temperature at 5 ug/ml, and the nonspecific binding sites were blocked with 1% bovine serum albumin (BSA) in PBS buffer. This plate was used to perform primary and secondary screening of the crude hybridoma supernatants. Hybridoma supernatants were added to the plates for binding to the coated KD or DAKD peptides. After 1 hour incubation, the plate was washed and bound antibodies were detected using horseradish peroxidase (HRP) conjugated secondary antibody (HRP-goat anti-mouse IgG (H+L): Jackson ImmunoResearch Labs #115-035-166) and developed using 2,2'-azino-bis(3-ethylbenzothiazoline-6-sulphonic acid) (ABTS) substrate (Roche diagnostics #11 204 521 001). Data was analyzed using Excel. The antibodies showing positive signals (2 fold higher than 1:10000 serum dilution ELISA signal) were selected and re-screened in duplicates for confirmation. Confirmed positive hybridoma clones were selected and subjected to binding dissociation rate ranking by Biacore.

For antibody binding kinetics, the instruments used were the BIACORE 2000 or BIACORE 3000 (GE Healthcare), designed for biomolecular interaction analysis (BIA) in real time. The sensor chip used was SA chip (GE Healthcare) with streptavidin covalently immobilized on a carboxymethylated dextran matrix. Each sensor chip has four parallel flow cells (Fc). Every biotinylated BKR1 or BKR2 ligand peptides were immobilized to one of the flow cells 2 to 4 (Fc2 to Fc4) in the SA chip for binding dissociation rate screening and selectivity screening. Flow cell 1 (Fc1) was reserved and immobilized with a random peptide (biotinylated at one terminus) with equal or close peptide length in comparison to the testing ligand peptides as the negative control. In screening assays, cell culture supernatants of the hybridoma clones selected through primary screening of transiently expressed humanized variants were injected over immobilized peptides. Hybridoma cell culture media was also injected over the chip surface as blank to establish a baseline. After subtracting signals of Fc1 and blank buffer runs, the dissociation rate of the antibodies from the supernatants to each peptide was analyzed and ranked using BIAevaluation software. Only the antibody clones that demonstrated superior (kd<10-4 1/s) binding dissociation rate were selected for subcloning and further characterization. In kinetics analysis, the corresponding biotin-peptides identified in screening for the testing antibody were immobilized in Fc2 to Fc4 while Fc1 with a random peptide used as reference cell. Each purified antibody selected from screenings were made into a series of two fold dilutions in running buffer (1×HBS-EP buffer, GE Healthcare) between 0.1 to 10 nM. Binding association rate, dissociation rate and the overall affinity were calculated in BIAevaluation. Antibody binding kinetics for each antibody was always confirmed in triplicate assays using Biacore.

A total of 8 mice were immunized with mixed KLH-KD/KD-KLH and KLH-DAKD/DAKD-KLH and the spleens were fused using the above protocols. After primary screening of about 7680 hybridoma clones in ELISA with DAKD-biotin and KD-biotin, only 76 clones were confirmed positive and selected for binding dissociation rate ranking in Biacore 3000/2000 over the immobilized DAKD-biotin and KD-biotin on Streptavidin (SA) chips. Among those, 8 hybridoma clones with binding dissociation rate<=of $10^{-4}$ were subcloned, sequenced, purified and further characterized (see Table 3).

TABLE 3

Immunization Results with KLH-KD/KD-KLH and KLH-DAKD/DAKD-KLH

| Ligand | Peptide Used in Assay | Assay | Clone ID | | | | | | | |
|---|---|---|---|---|---|---|---|---|---|---|
| | | | B21 | C63 | F151 | F306 | I2 | I8 | I22** | I54** |
| DAKD | b-DAKD | ELISA | + | + | − | − | + | + | + | + |
| | | Biacore (KD, M) | − | − | − | − | − | − | NS | NS |
| | DAKD-b | ELISA | + | + | + | + | + | + | + | + |
| | | Biacore (KD, M) | 4.15E−11 | 1.42E−10 | 1.60E−10 | 1.60E−10 | 1.10E−10 | 6.25E−10 | NTD | NTD |
| | DAKD (50 nM) | FLIPR (nM) | 22-25, 9 | − | 6.9 | 6.9 | | | 9.4 | 8.1 |
| DABK | b-DABK | ELISA | +/− | +/− | − | − | + | + | + | + |
| | | Biacore (KD, M) | − | − | − | − | − | − | NS | NS |
| | DABK-b | ELISA | + | +/− | − | − | + | + | + | + |
| | | Biacore (KD, M) | −* | − | − | − | − | − | NS | NS |
| | DABK | FLIPR (nM) | | | | | | | | |
| BK | b-BK | ELISA | − | − | − | − | − | − | − | − |
| | | Biacore (KD, M) | − | − | − | − | − | − | NS | NS |
| | BK-b | ELISA | + | − | − | − | + | + | + | + |
| | | Biacore (KD, M) | 8.57E−09 | − | − | − | − | − | NS | NS |
| | BK | FLIPR (nM) | − | − | − | − | | | | |
| KD | b-KD | ELISA | + | − | − | − | − | − | − | − |
| | | Biacore (KD, M) | − | − | − | − | − | − | NS | NS |
| | KD-b | ELISA | + | + | + | + | + | + | + | + |
| | | Biacore (KD, M) | 8.4E−11 | 2.21E−10 | 2.9E−11 | 2.9E−11 | 7.8E−11 | 7.53E−10 | NTD | NTD |
| | KD (15 nM)M) | FLIPR (nM) | 12 | − | 3.0 | 3.0 | 7.3 | 8.3 | 25 | 30 |

NA = not applicable, negative in ELISA
NS = nonspecific binding
NTD = not to be determined
−* = residual binding (low RU in Biacore)

Based on results seen in Table 3, five clones with unique sequences were selected for kinetic studies. These antibodies were highly selective for DAKD-biotin, KD-biotin, DAKLP-biotin and KLP-biotin binding (see Table 4). They do not bind to other kinin peptides or to peptides biotinylated at the N-terminus.

TABLE 4

Summary of Kinetics of Selected anti-DAKD/KD Antibody Candidates

| Antibody | DAKD-b | | KD-b | |
|---|---|---|---|---|
| | koff | KD | koff | KD |
| C63 | 9.36E−05 | 1.42E−10 | 1.00E−04 | 2.21E−10 |
| B21 | 9.89E−05 | 4.15E−11 | 2.04E−04 | 8.40E−11 |
| F151 | 1.36E−04 | 1.62E−10 | 2.00E−05 | 2.88E−11 |
| I22 | 3.19E−04 | 2.17E−10 | 2.10E−05 | 4.40E−12 |
| I54 | 3.06E−05 | 9.53E−12 | 3.88E−05 | 1.12E−11 |

TABLE 4-continued

Summary of Kinetics of Selected anti-DAKD/KD Antibody Candidates

| | DAKLP-b | | KLP-b | |
|---|---|---|---|---|
| | koff | KD | koff | KD |
| C63 | n/b | n/b | n/b | n/b |
| B21 | 2.30E−04 | 1.34E−10 | 1.12E−04 | 1.92E−10 |
| F151 | 6.58E−05 | 2.12E−10 | ≤1.0E−06 | ≈1.66E−11 |
| I22 | ≤1.0E−06 | ≈1.83E−12 | 1.03E−05 | 1.82E−12 |
| I54 | 5.66E−05 | 1.17E−11 | 6.04E−05 | 9.56E−12 | n/b = no binding

Additional immunization were performed with an array of immunogens (see list of peptides, Table 2) for generating antibodies blocking the rodent BKR1 ligands, DABK and DAKD as well as antibodies with other binding specificities against different member of kinin family of peptides. Table 5 lists the heavy and light sequences of the antibodies generated.

TABLE 5

Heavy and Light Chain Sequences of Antibodies

| Antibody | Isotype | SEQ ID NO. | Heavy Chain Sequence |
|---|---|---|---|
| B21 | IgG1/k | 97 | LPEFQVKLEESGAELVRSGASVKLSCTASGFNIKDYYLHWVKQRPEQGLEWIGWIDPENGDTGYARKFQGKATMTADTSSNTVYLHLSSLTSEDTAVYYFNAWEYDGYYDLDYWGQGTSVTVSSAKTTPPSVYGSS |
| C63 |  | 98 | LPEFQVLEESGGGLVQPGGSMKLSCVASGFTFSNYWMNWVRQSPEKGLEWVAEIRSKSNNYATHYAESVKGRFTISRDDSKSSVYLQMNNLRAEDTGIYYCIGEDYGGDYWGQGTSVTVSSAKTTPPSVYGSS |
| F151 |  | 99 | LPEFEVQLEESGPELVKPGTSVKVSCKASGYSFTDYNIYWVKQSHGKSLEWIGYFDPYNGNTGYNQKFRGKATLTVDKSSTAFMHLSSLTSDDSAVYYCANYYRYDDHAMDYWGQGTSVTVSSAKTTPPSVYGSS |
| I22 |  | 100 | LPEFEVKLQESGAELVRSGASVKLSCTASGFNIKDYYMHWVKQRPEQGLEWIGWVDPENGDSDYAPKFQGKATMTADTSSNTVYLQFSSLTSEDTAVYYCNAFEYDGNYSSLDFWGQGTSVTVSSAKTTPPSVYGSS |
| 154 |  | 101 | LPEFEVKLEQSGAELVRSGASVKLSCTASGFNIKDYYMHWVKQRPEQGLEWIGWVDPENGDSDYAPKFQGKATMTADTSSNTVYLQFSSLTSEDTAVYYCNAFEYDGNYSPLDFWGQGTSVTVSSAKTTPPSVYGSS |
| B21 | mIgG1/K | 118 | EVQLQQSGAELVRSGASVKLSCTASGFNIKDYYLHWVKQRPEQGLEWIGWIDPENGDTGYARKFQGKATMTADTSSNTVYLHLSSLTSEDTAVYYFNAWEYDGYYDLDYWGQGTSVTVSSAKTTPPS |
| C63 |  | 119 | EVKLEESGGGLVQPGGSMKLSCVASGFTFSNYWMNWVRQSPEKGLEWVAEIRSKSNNYATHYAESVKGRFTISRDDSKSSVYLQMNNLRAEDTGIYYCIGEDYGGDYWGQGTSVTVSSAKTTPPS |
| F151 |  | 120 | EIQLQQSGPELVKPGTSVKVSCKASGYSFTDYNIYWVKQSHGKSLEWIGYFDPYNGNTGYNQKFRGKATLTVDKSSTAFMHLSSLTSDDSAVYYCANYYRYDDHAMDYWGQGTSVTVSSAKTTPPS |
| I22 |  | 121 | EVQLQQSGAELVRSGASVKLSCTASGFNIKDYYMHWVKQRPEQGLEWIGWVDPENGDSDYAPKFQGKATMTADTSSNTVYLQFSSLTSEDTAVYYCNAFEYDGNYSPLDFWGQGTSVTVSSAKTTPPS |
| 154 |  | 122 | EVQLQQSGAELVRSGASVKLSCTASGFNIKDYYMHWVKQRPEQGLEWIGWVDPENGDSDYAPKFQGKATMTADTSSNTVYLQFSSLTSEDTAVYYCNAFEYDGNYSPLDFWGQGTSVTVSSAKTTPPS |
| B21 | IgG1/k | 102 | ELDIVMTQTTLTLSVTIGQPASISCKSSQSLLYSNGKTYLNWLLQRPGQSPKRLIYLVSKLDSGVPDRFTGSGSGTDFTLKIIRVEAEDLGVYYCLQGTHFPYTFGGGTKLEIKRADAAPTVSIFPPSKLELY |
| C63 |  | 103 | ELDIVLTQSPSSLAVSVGEKVTMSCKSSQSLLYSSDQRNYLAWYQQRSGQSPKLLIYWASTRESGVPDRFTGSGSGTDFTLTISSVKAEDLAVYYCQQYYSYPYTFGGGTKLEIKRADAAPTVSIFPPSKLELY |
| F151 |  | 104 | ELDIVMTQTPSSLAVSVGEKVTMSCKSSQSLLYTSNQKNYLAWYQQKPGQSPKPLIYWASTRESGVPDRFTGSGSGTDFTLTISSVKAEDLAIYYCQQYYSYPWTFGGGTKLEIKRADAAPTVSIFPPSKLELY |
| I22 |  | 105 | ELDIVITQTTLSLSVPIGQPASISCKSRQSLLYSNGETYLNWLLQRPGQSPKRLIYLVSKLDSGVPDRFTGSRSGTDFTLKISRVESEDLGVYYCMQGTHFPYTFGGGTKLEIKRADAAPTVSIFPPSKLELY |
| 154 |  | 106 | ELDIVITQSTLTLSVPIGQPASISCKSSQSLLYSNGETYLNWLLQRPGQSPKRQIYLVSKLDSGVPDRFTGSRSGTDFTLKISRVESEDLGVYYCMQGTHFPYTFGGGTKLEIKRADAAPTVSIFPPSKLELY |
| B21 | mIgG1/K | 123 | DVVMTQTPLTLSVTIGQPASISCKSSQSLLYSNGKTYLNWLLQRPGQSPKRLIYLVSKLDSGVPDRFTGSGSGTDFTLKIIRVEAEDLGVYYCLQGTHFPYTFGGGTKLEIKRADAAPT |
| C63 |  | 124 | DIVMSQSPSSLAVSVGEKVTMSCKSSQSLLYSSDQRNYLAWYQQRSGQSPKLLIYWASTRESGVPDRFTGSGSGTDFTLTISSVKAEDLAVYYCQQYYSYPYTFGGGTKLEIKRADAAPT |
| F151 |  | 125 | DIVMSQSPSSLAVSVGEKVTMSCKSSQSLLYSSNQKNYLAWYQQKPGQSPKPLIYWASTRESGVPDRFTGSGSGTDFTLTISSVKAEDLAIYYCQQYYSYPWTFGGGTKLELKRADAAPT |
| I22 |  | 126 | DIVMTQSPSSLSVSAGEKVTMSCKSSQSLLNSGNQKNYLAWYQQKPGQPPKLLIYGASTRESGVPDRFTGSGSGTDFTLTISSVQAEDLAVYYCQNDHSYPLTFGAGTKLELKRADAAPT |
| 154 |  | 131 | DVVMTQTPLTLSVPIGQPASISCKSSQSLLYSNGETYLNWLLQRPGQSPKRLIYLVSKLDSGVPDRFTGSRSGTDFTLKISRVESEDLGVYYCMQGTHFPYTFGGGTKLEIKRADAAPT |

Single underscore = CDR region;
double underscore = signature amino acids for identifying CDRs Example 3: Generation of Surrogate Antibody for Murine Animal Studies A surrogate antibody to be used in murine animal studies needed to be able to bind and neutralize rodent BKR1 ligands, DABK and DAKLP (mouse equivalent of DAKD). In order to generate the required surrogate antibody, mice were first immunized with DABK and/or DAKD with KLH directly conjugated to the N-terminals of the peptides. Biotin-DABK/biotin-DAKD (biotinylation directly on N-terminus of the peptide) positive hybridoma clones from ELISA screening were selected for scaling up and purification. The antibodies listed in Family 7 (see Table 12) that demonstrated high binding affinities to biotin-DABK, biotin-DAKLP and biotin-DAKD were selected based on Biacore direct binding assay (Table 10). However, these Family 7 antibodies showed no binding to the native, unmodified DABK and DAKD peptides in competitive ELISA, and lacked neutralizing functionality in a calcium influx assay with Functional Drug Screening System (FDSS) (Hamamatsu Photonics K.K., Japan). Moreover, the biotin-DABK and biotin-DAKD completely lost bioactivity in the FDSS assay in comparison to the native, unmodified DABK and DAKD peptides (data not shown).

It was hypothesized that the direct N-terminus conjugation of KLH and biotin prevented the native confirmation of DABK and DAKD to form. With the aim to restore the native conformation in KLH- and biotin-conjugated peptides, linkers were designed and added to the N-terminus of DABK and/or DAKD with the intention to "cushion" the KLH/biotin conjugation effects on peptide conformation. Poly-glycine linkers were first attempted and tested because of their simple, non-polar and neutral properties based on modeling results. The FDSS assay results indicated that the gly-gly-gly (3G) linker was the best according to its ability to restore the bioactivities of KLH and biotin conjugated DABK and DAKD peptides (data not shown). Therefore, KLH-3G-DABK was chosen to immunize mice. And biotin-3G-DABK and biotin-3G-KD were used in binding based screening assays (ELISA and Biacore). Several DABK/DAKD specific antibodies (Family 3, see Table 13) were identified in this new round of surrogate antibody hybridoma selection. EE1 was selected as the lead surrogate antibody based on its superior binding affinity and neutralization activity against native DABK/DAKD and lack of cross-reactivity to other peptides (see Tables 6-12)

Antibodies with different specificities were generated when using the different immunogens listed in Table 13. Family 4 antibodies were specific to the BKR2 receptor ligands, BK and KD. Family 5 antibodies specifically bind to the C terminus of BK and DABK. Family 6 antibodies bind BK, DABK and DAKD but do not bind to KD.

Additional linkers were evaluated for binding to the surrogate EE1 antibody for their ability to fit into the DABK/DAKD binding pocket in EE1, including longer poly-glycine linkers, poly-alanine linkers and preexisting linkers such as polyethylene glycol (PEG2) linker and aminohexanoic acid (Ahx) linker (a 6-carbon inert linker). All linker peptides were custom synthesized by Abgent (Can Diego, Calif.). All tested biotinylated peptides with linkers (biotin-linker-DABK/DAKD) bound well to EE1, indicating that any inert N-terminus linkers helped DABK and DAKD peptides to retain their native bioactive conformation when conjugated with biotin and other molecules. In contrast, no binding or poor binding to EE1 was observed with biotin-DABK and biotin-DAKD, peptides that have direct N-terminal biotin conjugation (see FIG. 1).

The binding kinetics of generated antibodies are summarized in Tables 5-11. Then, all antibodies generated were sorted into families and their binding specificities are summarized below in Table 12. Table 13 provides the heavy and light chain sequences of antibodies that were placed into family 1 and family 2 based on their binding specificity (see Table 12).

TABLE 6

Summary of Antibody Kinetics to b-3G-DABK and b-3G-DAKD Peptides

| | b-3G-DABK | | | b-3G-DAKD | | |
|---|---|---|---|---|---|---|
| Clone | Ka(1/Ms) | Kd(1/s) | KD(M) | Ka(1/Ms) | Kd(1/s) | KD(M) |
| DD20 | 1.5E+06 | 2.3E−04 | 1.6E−10 | 4.7E+05 | 4.0E−04 | 8.8E−10 |
| UR11 | 2.0E+05 | 3.0E−04 | 1.5E−09 | 3.0E+05 | 1.6E−03 | 5.2E−09 |
| DD7 | 2.3E+05 | 6.0E−04 | 2.7E−09 | 2.1E+05 | 1.4E−03 | 6.6E−09 |
| EE1 | 4.4E+05 | 1.2E−04 | 2.8E−10 | 4.4E+05 | 2.0E−04 | 4.5E−10 |
| EE36 | 4.3E+03 | 5.3E−04 | 1.2E−07 | n/b | n/b | n/b |
| UR29 | n/b* | n/b | n/b | n/b | n/b | n/b |
| JK3 | 3.44E+05 | 3.91E−05 | 1.14E−10 | 3.18E+05 | 5.07E−05 | 1.60E−10 |
| LR4 | n/b | n/b | n/b | n/b | n/b | n/b |
| LR16 | n/b | n/b | n/b | n/b | n/b | n/b |
| LR6 | n/b | n/b | n/b | n/b | n/b | n/b |
| LR12 | n/b | n/b | n/b | n/b | n/b | n/b |
| NR1 | n/b | n/b | n/b | n/b | n/b | n/b |
| NR15 | n/b | n/b | n/b | n/b | n/b | n/b | n/b* = non-specific binding,
n/b = no binding

TABLE 7

Summary of Antibody Kinetics to b-3G-DAKLP and b-3G-BK Peptides

| | b-3G-DAKLP | | | b-3G-BK | | |
|---|---|---|---|---|---|---|
| Clone | Ka(1/Ms) | Kd(1/s) | KD(M) | Ka(1/Ms) | Kd(1/s) | KD(M) |
| DD20 | 3.1E+05 | 6.1E−04 | 2.0E−09 | 3.0E+05 | 7.1E−04 | 2.3E−09 |
| UR11 | n/b | n/b | n/b | n/b | n/b | n/b |
| DD7 | 1.7E+05 | 2.1E−03 | 1.2E−08 | 1.3E+05 | 8.8E−04 | 6.8E−09 |
| EE1 | 4.2E+05 | 2.9E−04 | 6.8E−10 | 2.5E+05 | 2.6E−03 | 1.1E−08 |
| EE36 | n/b | n/b | n/b | n/b | n/b | n/b |
| UR29 | n/b | n/b | n/b | n/b | n/b | n/b |
| JK3 | ND | ND | ND | n/b | n/b | n/b |

TABLE 7-continued Summary of Antibody Kinetics to b-3G-DAKLP and b-3G-BK Peptides

| Clone | b-3G-DAKLP | | | b-3G-BK | | |
|---|---|---|---|---|---|---|
| | Ka(1/Ms) | Kd(1/s) | KD(M) | Ka(1/Ms) | Kd(1/s) | KD(M) |
| LR4 | n/b | n/b | n/b | n/b | n/b | n/b |
| LR16 | n/b | n/b | n/b | n/b | n/b | n/b |
| LR6 | n/b | n/b | n/b | n/b | n/b | n/b |
| LR12 | n/b | n/b | n/b | n/b | n/b | n/b |
| NR1 | n/b | n/b | n/b | n/b | n/b | n/b |
| NR15 | n/b | n/b | n/b | n/b | n/b | n/b | n/b = no binding;
ND = not determined

TABLE 8

Summary of Antibody Kinetics to b-3G-KLP and b-3G-KD Peptides

| Clone | b-3G-KLP | | | b-3G-KD | | |
|---|---|---|---|---|---|---|
| | Ka (1/Ms) | Kd (1/s) | KD (M) | Ka (1/Ms) | Kd (1/s) | KD (M) |
| DD20 | 3.8E+05 | 5.7E−04 | 1.5E−09 | n/b | n/b | n/b |
| UR11 | n/b | n/b | n/b | 1.2E+05 | 1.3E−03 | 1.1E−08 |
| DD7 | 1.5E+05 | 2.1E−03 | 1.5E−08 | 2.2E+05 | 1.8E−03 | 8.4E−09 |
| EE1 | 4.0E+05 | 2.1E−03 | 5.3E−09 | n/b | n/b | n/b |
| EE36 | n/b | n/b | n/b | n/b | n/b | n/b |
| UR29 | n/b | n/b | n/b | n/b | n/b | n/b |
| JK3 | ND | ND | ND | n/b | n/b | n/b |
| LR4 | n/b | n/b | n/b | n/b | n/b | n/b |
| LR16 | n/b | n/b | n/b | n/b | n/b | n/b |
| LR6 | n/b | n/b | n/b | n/b | n/b | n/b |
| LR12 | n/b | n/b | n/b | n/b | n/b | n/b |
| NR1 | n/b | n/b | n/b | n/b | n/b | n/b |
| NR15 | n/b | n/b | n/b | n/b | n/b | n/b | n/b = no binding;
ND = not determined

TABLE 9

Summary of Antibody Kinetics to DABK-b and DAKLP-b Peptides

| Clone | DABK-b | | | DAKLP-b | | |
|---|---|---|---|---|---|---|
| | Ka (1/Ms) | Kd (1/s) | KD (M) | Ka (1/Ms) | Kd (1/s) | KD (M) |
| DD20 | n/b | n/b | n/b | n/b | n/b | n/b |
| UR11 | n/b | n/b | n/b | n/b | n/b | n/b |
| DD7 | n/b | n/b | n/b | n/b | n/b | n/b |
| EE1 | n/b | n/b | n/b | n/b | n/b | n/b |
| EE36 | n/b | n/b | n/b | n/b | n/b | n/b |
| UR29 | 1.5E+06 | 5.8E−05 | 3.9E−11 | 3.0E+06 | 2.1E−03 | 6.8E−10 |
| JK3 | n/b | n/b | n/b | n/b | n/b | n/b |
| LR4 | n/b | n/b | n/b | n/b | n/b | n/b |
| LR16 | n/b | n/b | n/b | n/b | n/b | n/b |
| LR6 | n/b | n/b | n/b | n/b | n/b | n/b |
| LR12 | n/b | n/b | n/b | n/b | n/b | n/b |
| NR1 | n/b | n/b | n/b | n/b | n/b | n/b |
| NR15 | n/b | n/b | n/b | n/b | n/b | n/b | n/b = no binding;
ND = not determined

TABLE 10

Summary of Antibody Kinetics to BK-b and b-BK Peptides

| | BK-b | | | b-BK | | |
|---|---|---|---|---|---|---|
| Clone | Ka (1/Ms) | Kd (1/s) | KD (M) | Ka (1/Ms) | Kd (1/s) | KD (M) |
| DD20 | n/b | n/b | n/b | n/b | n/b | n/b |
| UR11 | n/b | n/b | n/b | n/b | n/b | n/b |
| DD7 | n/b | n/b | n/b | n/b | n/b | n/b |
| EE1 | n/b | n/b | n/b | n/b | n/b | n/b |
| EE36 | n/b | n/b | n/b | n/b | n/b | n/b |
| UR29 | 1.5E+06 | 1.0E−04 | 7.2E−11 | n/b | n/b | n/b |
| JK3 | n/b | n/b | n/b | n/b | n/b | n/b |
| LR4 | n/b | n/b | n/b | n/b | n/b | n/b |
| LR16 | n/b | n/b | n/b | n/b | n/b | n/b |
| LR6 | n/b | n/b | n/b | n/b | n/b | n/b |
| LR12 | n/b | n/b | n/b | n/b | n/b | n/b |
| NR1 | n/b | n/b | n/b | 8.69E+04 | 8.77E−04 | 1.01E−08 |
| NR15 | n/b | n/b | n/b | 2.95E+05 | 1.09E−03 | 3.68E−09 | n/b = no binding;
ND = not determined

TABLE 11

Summary of Antibody Kinetics to b-DABK and b-DAKD Peptides

| | b-DABK | | | b-DAKD | | |
|---|---|---|---|---|---|---|
| Clone | Ka (1/Ms) | Kd (1/s) | KD (M) | Ka (1/Ms) | Kd (1/s) | KD (M) |
| DD20 | n/b | n/b | n/b | n/b | n/b | n/b |
| UR11 | n/b | n/b | n/b | n/b | n/b | n/b |
| DD7 | n/b | n/b | n/b | n/b | n/b | n/b |
| EE1 | n/b | n/b | n/b | n/b | n/b | n/b |
| EE36 | n/b | n/b | n/b | n/b | n/b | n/b |
| UR29 | n/b | n/b | n/b | n/b | n/b | n/b |
| JK3 | n/b | n/b | n/b | n/b | n/b | n/b |
| LR4 | 1.48E+05 | 1.04E−03 | 7.15E−09 | 3.27E+05 | 7.63E−04 | 2.36E−09 |
| LR16 | 4.34E+05 | 4.38E−05 | 1.01E−10 | 2.07E+05 | 3.39E−03 | 1.65E−08 |
| LR6 | n/b | n/b | n/b | n/b | n/b | n/b |
| LR12 | 2.91E+05 | 5.40E−04 | 3.63E−09 | n/b | n/b | n/b |
| NR1 | n/b | n/b | n/b | n/b | n/b | n/b |
| NR15 | n/b | n/b | n/b | n/b | n/b | n/b | n/b = no binding;
ND = not determined

TABLE 12

Summary of Antibody Kinetics to b-DAKLP and b-KD Peptides

| | b-DAKLP | | | b-KD | | |
|---|---|---|---|---|---|---|
| Clone | Ka (1/Ms) | Kd (1/s) | KD (M) | Ka (1/Ms) | Kd (1/s) | KD (M) |
| DD20 | n/b | n/b | n/b | n/b | n/b | n/b |
| UR11 | n/b | n/b | n/b | n/b | n/b | n/b |
| DD7 | n/b | n/b | n/b | n/b | n/b | n/b |
| EE1 | n/b | n/b | n/b | n/b | n/b | n/b |
| EE36 | n/b | n/b | n/b | n/b | n/b | n/b |
| UR29 | n/b | n/b | n/b | n/b | n/b | n/b |
| JK3 | n/b | n/b | n/b | n/b | n/b | n/b |
| LR4 | 1.84E+05 | 2.58E−04 | 1.40E−09 | n/b | n/b | n/b |
| LR16 | 2.34E+05 | 1.11E−04 | 4.74E−10 | n/b | n/b | n/b |
| LR6 | 6.80E+05 | 4.01E−04 | 7.45E−10 | n/b | n/b | n/b |
| LR12 | n/b | n/b | n/b | n/b | n/b | n/b |
| NR1 | n/b | n/b | n/b | 1.66E+05 | 5.81E−03 | 3.56E−08 |
| NR15 | n/b | n/b | n/b | 7.66E+05 | 5.66E−03 | 7.41E−09 | n/b = no binding;
ND = not determined

TABLE 13

Summary of Anti-kinin peptide antibody generation

| Antibody Families | Immunogens | Representative antibodies | Binding Specificity |
|---|---|---|---|
| Family 1 | KD-KLH + KLH-KD or DAKD-KLH + KLH-DAKD | F151, B21, I22, I54 | N-terminus of DAKD (DAKLP) and KD (KLP) |
| Family 2 | KD-KLH + KLH-KD or DAKD-KLH + KLH-DAKD | C63 | N-terminus of DAKD and KD |
| Family 3 | KLH-3G-DABK | EE1, DD20, JK3 | C-terminus of DABK and DAKD (DAKLP) |
| Family 4 | KLH-BK and BSA-BK | NR15, NR1 | C-terminus of BK and KD |
| Family 5 | KLH-BK | UR29 | N-terminus of BK and DABK |
| Family 6 | KLH-BK | UR11 | BK, DABK and DAKD |
| Family 7 | KLH-DABK or KLH-DAKD | LR4, LR6, LR12 and LR16 | no binding with native peptides |

Example 4: Characterization of des-arg-Kinin Ligand Depletion using Calcium Mobilization A functional assay was used to further characterize the seven families of generated antibodies. The Bradykinin B1 Receptor signaling is Gq coupled, therefore receptor activation can be monitored using Gq activation of IP3 and downstream calcium mobilization. HEK mBKR1 (recombinant mouse bradykinin B1 receptor) cells or MRC5 (endogenous expression of bradykinin B2 receptors; (ATCC CCL-171)) were used to measure calcium mobilization.

Briefly, the mouse Bdkrb1 gene (sequence provided below) was amplified from mouse lung cDNA (Biochain, Cat# C1334152) using PCR primers 804_cGWY_F: 5'-AAAAGCAGGCTTAGGAGCGGCCGCCATG-GCGTCCAGGCCTCGCTG-3' (SEQ ID NO: 107) and 804_cGWY_R: 5'-CAAGAAAGCTGGGTCGGATCCT-TATAAAGTTCCCAGAACCCTGGTC-3' (SEQ ID NO: 108) and Pfu Polymerase (Agilent Technologies, Cat#600264) and cloned into pDONR201 using BP clonase enzyme mix (Invitrogen, Cat#11789-020). In parallel, the pEAK8 expression vector (EDGE Biosystems) was modified by inserting a N-terminal HA tag (GCATACCCATAC-GACGTCCCAGACTACGCT, GenBank SEQ ID NO:109 CY100443) into pEAK8 linearized with EcoRI and HindIII (vector pEAK8-nHA) and subsequent insertion of the Gateway cassette B (Invitrogen, Cat#11828-029) into pEAK8_nHA digested with EcoRI and NotI and blunt-ended with Klenow polymerase (NEB, cat# M0210S) resulting in vector pEAK8_nHA_DEST. Next mouse Bdkrb1 was subcloned into pEAK8_nHA_DEST using LR clonase (Invitrogen, Cat#11791-100). 293-PSC cells were then transfected with pEAK8-Bdkrb1 plasmid using Fugene 6 transfection reagent. The cells were put under antibiotic (puromycin) selection 24 hours after transfection, and selection was maintained to generate a stable cell line. Presence of the Bdkrb1 gene in the resultant stable cell lines was confirmed using real time RT-PCR, and by agarose gel electrophoresis. Cell surface expression of the Bradykinin B1 receptor was performed by using an antibody against the N-terminal-HA tag (Covance, Cat # MMS-101P) on the Bradykinin B1R on a FACS instrument. Functional activity of the Bradykinin B1 receptor was demonstrated in calcium mobilization assay with selective agonists.

Bdkrb1 gene subcloned into cells:

(GenBank NM_007539; SEQ ID NO: 110)
ATGGCGTCCCAGGCCTCGCTGAAGCTACAGCCTTCTAACCAAAGCCAG

CAGGCCCCTCCCAACATCACCTCCTGCGAGGGCGCCCCGGAAGCCTGG

GATCTGCTGTGTCGGGTGCTGCCAGGGTTTGTCATCACTGTCTGTTTC

TTTGGCCTCCTGGGGAACCTTTTAGTCCTGTCCTTCTTCCTTTTGCCT

TGGCGACGATGGTGGCAGCAGCGGCGGCAGCGCCTAACCATAGCAGAA

ATCTACCTGGCTAACTTGGCAGCTTCTGATCTGGTGTTTGTGCTGGGC

CTGCCCTTCTGGGCAGAGAACGTTGGGAACCGTTTCAACTGGCCCTTT

GGAAGTGACCTCTGCCGGGTGGTCAGCGGGGTCATCAAGGCCAACCTG

TTCATCAGCATCTTCCTGGTGGTGGCCATCAGTCAGGACCGCTACAGG

TTGCTGGTATACCCCATGACCAGCTGGGGGAACCGGCGGCGACGGCAA

GCCCAAGTGACCTGCCTGCTCATCTGGGTAGCTGGGGGCCTCTTGAGC

ACCCCCACGTTCCTTCTGCGTTCCGTCAAAGTCGTCCCTGATCTGAAC

ATCTCTGCCTGCATCCTGCTTTTCCCCCACGAAGCTTGGCACTTTGTA

AGGATGGTGGAGTTGAACGTTTTGGGTTTCCTCCTCCCATTGGCTGCC

ATCCTCTACTTCAACTTTCACATCCTGGCCTCCCTGAGAGGACAGAAG

GAGGCCAGCAGAACCCGGTGTGGGGGACCCAAGGACAGCAAGACAATG

GGGCTGATCCTCACACTGGTAGCCTCCTTCCTGGTCTGCTGGGCCCCT

TACCACTTCTTTGCCTTCCTGGATTTCCTGGTCCAGGTGAGAGTGATC

CAGGACTGCTTCTGGAAGGAGCTCACAGACCTGGGCCTGCAGCTGGCC

AACTTCTTTGCTTTTGTCAACAGCTGCCTGAACCCACTGATTTATGTC

TTTGCAGGCCGGCTCTTTAAGACCAGGGTTCTGGGAACTTTATAA

HEK mBKR1 or MRC5 cells were plated into 384 well clear bottom plates in growth medium, and allowed to attach overnight. Then growth media was removed, cells were washed in assay buffer (HBSS, 20 mM HEPES, 2.5 mM probenecid), then dye-loaded with 0.5 uM Fluo-4AM, a cell permeable calcium sensing dye, with 0.04% Pluronic Acid for 1 hr at 37 C. The AM ester is cleaved, and the calcium dye is retained in the cytoplasm. After 1 hr, the cells were washed to remove excess dye, and 20 ul of residual buffer remained on the cells. Treatments were added as 2x solutions on the Functional Drug Screening System from Hamamatsu (FDSS), and the calcium mobilization was monitored kinetically for at least 4 minutes. B1R or B2R receptor activation results in Galpha q mediated activation of phospholipase C and IP3 mediated calcium mobilization. The Fluo-4 dye chelates the released calcium, and a robust change in fluorescence is observed. The results were exported as max-min relative fluorescence units to normalize for differences between cell density or dye loading across the plate.

Ligand potency was determined each day by running concentration response curves of ligand, and an approximate EC70-80 concentration of ligand was selected for incubation with antibodies. An EC80 concentration was selected because it is on the linear range of the detection curve and there was ample window to see a decrease with antagonists or ligand depleting antibodies. Dose response curve of antibodies were allowed to bind a EC80 concentration ligand, and the extent of ligand depletion was monitored using change in fluorescence. Results were normalized to buffer and EC80 ligand response, and an EC50 for ligand depletion was calculated. The results were then reported as molar ratio which corresponds to the Antibody concentration that reduces depletes 50% of the ligand response (i.e., EC50 of Ab) divided by the ligand concentration used. The theoretical max should be 0.5 because one unit of antibody should be able to deplete 2 units of ligand, but we have seen lower values in practice but that may be a reflection of the insensitivity of the detection method for low ligand concentrations, rather than a stochiometric constraint for the antibody. The results of these experiments are set forth in Tables 14-16.

All family 1 and family 2 antibodies (see Table 13) demonstrated superior binding kinetics by Biacore (Table 3) and neutralization activity as measured by calcium mobilization against DAKD and KD peptides (Tables 14 and 15). The antibodies were further analyzed for their thermal stability and sequence suitability for humanization. F151 was advanced for humanization because it was thermally stable, there were no problematic residues in the CDR regions and it was cross-reactive to the mouse ligand KLP and DAKLP.

TABLE 14

Characterization of des-arg-Kinin Ligand Depletion using Calcium Mobilization in HEK mBKR1 cells

| | | Depletion of DABK | | | Depletion of DAKD | | | Depletion of DAKLP | | |
|---|---|---|---|---|---|---|---|---|---|---|
| Family | Antibody | DABK (Mean Molar Ratio) | SD Molar Ratio | n | DAKD (Mean Molar Ratio) | SD Molar Ratio | n | DAKLP (Mean Molar Ratio) | SD Molar Ratio | n |
| 1 | F151 | IA100 | | 5 | 0.08 | 0.04 | 7 | 0.15 | 0.04 | 4 |
| 1 | B21 | IA100 | | 1 | 0.15 | 0.04 | 3 | 0.67 | | 1 |
| 1 | I22 | IA100 | | 1 | 0.07 | 0.02 | 3 | 0.21 | | 1 |
| 1 | I54 | IA100 | | 1 | 0.15 | 0.05 | 3 | 0.35 | | 1 |
| 2 | C63 | IA100 | | 1 | 0.08 | 0.02 | 3 | 5.85 | | 1 |
| 3 | EE1 | 1.03 | 0.52 | 5 | 0.86 | 0.52 | 3 | 0.57 | 0.36 | 4 |
| 3 | DD20 | 3.45 | 1.34 | 3 | 1.82 | 0.76 | 3 | 1.31 | 0.86 | 3 |
| | DD7 | 2.18 | 0.45 | 3 | 4.22 | 0.95 | 3 | 5.34 | 1.22 | 2 |
| 3 | JK3 | 1.86 | 0.03 | 2 | ND | | | 1.44 | 0.03 | 2 |
| 4 | MBK3 | ND | | | ND | | | ND | | |
| 4 | NR15 | ND | | | ND | | | ND | | |
| 4 | NR1 | ND | | | ND | | | ND | | |
| 5 | UR29 | 0.60 | 0.12 | 5 | IA200 | | 3 | IA300 | | 4 |
| 6 | UR11 | 6.99 | 1.61 | 3 | 19.65 | 14.95 | 3 | 11.09 | 3.13 | 2 |
| 7 | LR4 | IA100 | | 1 | IA400 | | 1 | IA400 | | 1 |
| 7 | LR6 | IA100 | | 1 | IA100 | | 1 | ND | | |
| 7 | LR12 | IA100 | | 1 | IA100 | | 1 | ND | | |
| 7 | LR16 | IA100 | | 1 | IA100 | | 1 | ND | | |

Antibodies were pre-incubated with a set concentration of ligand, usually an EC70-80 for activating calcium mobilization at the Bradykinin B1 Receptor. The antibody-ligand mixture was added to HEK mBKR1 cells pre-loaded with a calcium sensing dye (Fluo-4AM or Fluo-8AM) on the Hamamatsu FDSS6000 instrument, and calcium mobilization was monitored. Data was exported as a max-min relative fluorescence of the biological response, and IC50 for ligand depletion was calculated using sigmoidal curve fit in Graph Pad Prism V4.03. Data reported as molar ratio for ligand depletion by the antibody to standardize the different concentration of ligand that was used for the various experiments.
Molar Ratio for ligand depletion = [IC50 of Antibody]/[Ligand]
SD = Standard Deviation;
ND = not determined;
IA100 = Inactive at 100 nM;
IA200 = Inactive at 200 nM;
IA300 = Inactive at 300 nM;
IA400 = Inactive at 400 nM

TABLE 15

Characterization of Kinin Ligand Depletion using Calcium Mobilization in MRC5 Fetal Lung Fibroblasts cells

| | | Depletion of BK | | | Depletion of KD | | | Depletion of KLP | | |
|---|---|---|---|---|---|---|---|---|---|---|
| Family | Antibody | BK (Mean Molar Ratio) | SD Molar Ratio | n | KD (Mean Molar Ratio) | SD Molar Ratio | n | KLP (Mean Molar Ratio) | SD Molar Ratio | n |
| 1 | F151 | IA100 | | 5 | 0.14 | 0.05 | 5 | 0.15 | 0.02 | 3 |
| 1 | B21 | IA100 | | 1 | 0.33 | | 1 | ND | | |
| 1 | I22 | IA100 | | 1 | 0.22 | | 1 | ND | | |
| 1 | I54 | IA100 | | 1 | 0.30 | | 1 | ND | | |
| 2 | C63 | IA100 | | 1 | 0.23 | | 1 | ND | | |
| 3 | EE1 | IA300 | | 4 | IA300 | | 4 | IA150 | | 1 |

TABLE 15-continued

Characterization of Kinin Ligand Depletion using Calcium
Mobilization in MRC5 Fetal Lung Fibroblasts cells

| Family | Antibody | Depletion of BK | | | Depletion of KD | | | Depletion of KLP | | |
|---|---|---|---|---|---|---|---|---|---|---|
| | | BK (Mean Molar Ratio) | SD Molar Ratio | n | KD (Mean Molar Ratio) | SD Molar Ratio | n | KLP (Mean Molar Ratio) | SD Molar Ratio | n |
| 3 | DD20 | IA600 | | 4 | IA600 | | 5 | IA150 | | 1 |
| | DD7 | 7.11 | 3.62 | 3 | 17.37 | 12.11 | 3 | 4.27 | | 1 |
| 3 | JK3 | IA300 | | 2 | IA300 | | 2 | ND | | |
| 4 | MBK3 | 22.11 | 14.10 | 9 | 3.46 | 2.64 | 6 | 9.45 | | 1 |
| 4 | NR15 | 15.26 | 11.51 | 5 | 4.34 | 2.55 | 5 | 11.18 | | 1 |
| 4 | NR1 | 39.31 | | 1 | 42.15 | | 1 | 32.58 | | 1 |
| 5 | UR29 | 1.15 | 0.86 | 5 | 0.30 | 0.08 | 2 | 0.41 | | 1 |
| 6 | UR11 | 5.41 | 0.80 | 2 | 25.21 | 4.54 | 2 | 1.53 | | 1 |
| 7 | LR4 | IA100 | | 1 | IA100 | | 1 | ND | | |
| 7 | LR6 | IA100 | | 1 | IA100 | | 1 | ND | | |
| 7 | LR12 | IA100 | | 1 | IA100 | | 1 | ND | | |
| 7 | LR16 | IA100 | | 1 | IA100 | | 1 | ND | | |

Antibodies were pre-incubated with a set concentration of ligand, usually an EC70-80 for activating calcium mobilization at the Bradykinin B2 Receptor. The antibody-ligand mixture was added to MRC5 Fetal Lung Fibroblasts (ATCC CCL-171) pre-loaded with a calcium sensing dye (Fluo-4AM or Fluo-8AM) on the Hamamatsu FDSS6000 instrument, and calcium mobilization was monitored. Data was exported as a max-min relative fluorescence of the biological response, and IC50 for ligand depletion was calculated using sigmoidal curve fit in Graph Pad Prism V4.03. Data reported as molar ratio for ligand depletion by the antibody to standardize the different concentration of ligand that was used for the various experiments.
Molar Ratio for ligand depletion = [IC50 of Antibody]/[Ligand]
SD = Standard Deviation;
ND = not determined;
IA100 = Inactive at 100 nM;
IA150 = Inactive at 150 nM;
IA300 = Inactive at 300 nM;
IA400 = Inactive at 400 nM;
IA600 = Inactive at 600 nM Example 5: Engineering of F151: Humanization, Stabilization and Mutation of Unwanted Sequence Motifs 1. Humanization The humanization protocol used has been described in PCT/US08/74381 (US20110027266), herein incorporated by reference in its entirety. The variable light (VL) and variable heavy (VH) sequences of murine F151 were used to build a homology model of anti-DAKD/KD F151 LC and HC in Molecular Operating Environment (MOE; v. 2009.10; Chemical Computing Group). The following templates were used: light chain framework—1SBS (93% identity in the framework regions), heavy chain framework—2VXT (84% identity in the framework regions), L1—1LVE (93% identity), L2—1 EEU (100% identity), L3—2R56 (93% identity), H1—1NJ9 (95% identity), H2—2VXU (76% identity) and H3—1HIL (49% identity). Templates were available at the RCSB Protein Data Bank found on the world wide web at rcsb.org, a website managed by Rutgers and the University of California San Diego (Berman, H. M; Westbrook J.; Feng. Z.; Gilliland, G.; Bhat, T. N.; Weissig, H.; Shindyalov, I. N.; Bourne, P. E. The Protein Data Bank, Nucleic Acids Research, 2000, 28, 235-242.). The homology model was subsequently energy minimized using the standard procedures implemented in MOE. A molecular dynamics (MD) simulation of the minimized 3D homology model of the murine F151 was subsequently performed, with constraints on the protein backbone at 500 K temperature for 1.1 nanoseconds (ns) in Generalized Born implicit solvent. Ten diverse conformations were extracted from this first MD run every 100 picoseconds (ps) for the last 1 ns. These diverse conformations were then each submitted to a MD simulation, with no constraints on the protein backbone and at 300 K temperature, for 2.3 ns. For each of the 10 MD runs, the last 2,000 snapshots, one every ps, from the MD trajectory were then used to calculate, for each murine F151 amino acid, its root mean square deviations (rmsd) compared to a reference medoid position. By comparing the average rmsd on the 10 separate MD runs of a given amino-acid to the overall average rmsd of all F151 murine amino-acids, one decides if the amino-acid is flexible enough, as seen during the MD to be considered as likely to interact with T-cell receptors and responsible for activation of the immune response. 62 amino-acids were identified as flexible in the murine F151 antibody, excluding the CDR and its immediate 5 Å vicinity.

The motion of the 28 most flexible murine F151 amino acids, during the 20 ns (10×2 ns), were then compared to the motion of the corresponding flexible amino-acids of 49 human germline homology models, for each of which were run the 10×2 ns MD simulations. The 49 human germline models were built by systematically combining the 7 most common human germline light chains (vk1, vk2, vk3, vk4, vlambda1, vlambda2, vlambda3) and 7 most common human germline heavy chains (vh1a, vh1b, vh2, vh3, vh4, vh5, vh6). The vk1-vh1b human germline antibody showed 0.80 4D similarity of its flexible amino-acids compared to the flexible amino-acids of the murine F151 antibody; the vk1-vh1b germline antibody was therefore used to humanize F151 antibody focusing on the flexible amino-acids. For the pair wise amino-acid association between murine F151 vk1-vh1b amino-acids, the 2 sequences were aligned based on the optimal 3D superposition of the alpha carbons of the 2 corresponding homology models (see FIG. 15 for an alignment of F151 LC and F151 HC with vk1 and vh1b, respectively).

2. Stabilization

Two approaches were used to improve the stability of the antibody.

A) Knowledge-Based Approach

The amino acids of the light and heavy chains with low frequency of occurrence vs. their respective canonical sequences, excluding the CDRs, were proposed to be mutated into the most frequently found amino acids (ΔΔGth>0.5 kcal/mol; E. Monsellier, H. Bedouelle. J. Mol. Biol. 362, 2006, p. 580-593). This first list of consensus mutations for the light chain (LC) and heavy chain (HC) was restricted to the amino acids found in the closest human germline (vk1-vh1b). Suggested changes in the immediate vicinity of the CDRs (5 Angstroms "Vernier" zone, J. Mol. Biol. 224, 1992, p. 487-499) were removed from consideration. This resulted in 5 stabilizing mutations in the LC (see Table 19) and 4 stabilizing mutations in the HC (see Table 20). Other criteria were taken into account to consider these mutations for potentially stabilizing the anti-DAKD/KD F151 antibody. These criteria were a favorable change of hydropathy at the surface or a molecular mechanics based predicted stabilization of the mutant. Also, additional stabilizing mutations reported to be successful in the literature (E. Monsellier & H. Bedouelle, J. Mol. Biol., 362, 2006, p. 580-593; B. J. Steipe et al. J. Mol. Biol, 1994, 240, 188-192) were considered (see Tables 16-22). One of these changes was incorporated as a stabilizing mutation (D89E) in sequences HC2a, HC2b and HC2c below. Another suggested change (Q62E) was incorporated in variant HC2b.

b) 3D and Md-Based Approaches 3D and MD-based approaches have been previously reported (Seco J, Luque F J, Barril X., J Med Chem. 2009 Apr. 23; 52(8):2363-71; Malin Jonsson et al., J. Phys. Chem. B 2003, 107, 5511-5518). Hydrophobic regions of the antibody were explicitly identified by analyzing the molecular dynamics simulation of the Fab in a binary solvent (20% isopropanol in water, 20 ns production simulation). Lysine mutations were then introduced in the vicinity of these regions as an attempt to prevent the aggregation. Additional analysis using a hydrophobic surface map within Schrodinger's maestro software (v. 8.5.207) was completed. Using a combination of these two techniques, 2 Lys mutations, 1 in the heavy chain and 1 in the light chain, are suggested.

3. Humanization by Grafting

Humanization using grafting techniques has previously been reported (Peter T. Jones, Paul H. Dear, Jefferson Foote, Michael S. Neuberger & Greg Winter Nature, 1986, 321, 522-525). The humanization process which was used started by identifying the closest human germlines to anti-DAKD/KD light and heavy chains. This is done by performing a BLAST search vs. all the human germlines which were systematically enumerated (all possible combinations of the V & J domains for the kappa and lambda chains; V, D and J domains for the heavy chains).

The following closest human germlines were identified with 83% and 62% sequence identity to anti-DAKD/KD F151 light chains (LC) and heavy chains (HC), respectively (see FIG. 16). Using the internal VBASE germline, the light chain is found to be close to V☐IV-B3 (~83% identity) locus and the heavy chain close to 1-08 & 1-18 (~62% identity) locus of the VH1 sub-family. CDR regions (as defined by MOE), and Vernier regions (as defined in Foote & Winter, J. Mol. Biol., 1992, 224, 487-499) are indicated in boldface The humanizing mutations in underlining were obtained by performing a pairwise comparison of the 2 aligned sequences, excluding the CDR & Vernier zone residues as defined above. In another variant of the humanization, only the CDRs were excluded in the comparison.

4. Mutation of Unwanted Sequence Motifs

The following motifs of sequences were considered: Asp-Pro (acid labile bond), Asn-X-Ser/Thr (glycosylation, X=any amino-acid but Pro), Asp-Gly/Ser/Thr (succinimide/iso-asp formation in flexible regions), Asn-Gly/His/Ser/Ala/Cys (exposed deamidation sites), and Met (oxidation in exposed areas). Among other criteria, the VL & VH domains of murine F151 was selected from other murine antibodies because murine F151 did not have exposed unwanted sequence motifs, but they are introduced in some humanized variants.

LC3a, LC3b, HC3a and HC3b each have potentially problematic succinimide sites that were identified. These sites were not modified in the proposed sequences as the residues involved are potentially involved in H-bond network (visual inspection of the homology model). These positions are also found in a number of other antibody structures. Additionally, in both HC3a and HC3b, a strict humanization by grafting would include a substitution of Ser115 to Met. This Methionine is exposed. A substitution to Leucine at this position is suggested as a humanizing mutation as it is a common residue among many close human germline sequences.

The resulting humanized sequences were blasted for sequence similarity against the International Epitope Database (IEDB) database (found on the world wide web at immuneepitope.com; version June 2009; Vita R, Zarebski L, Greenbaum J A, Emami H, Hoof I, Salimi N, Damle R, Sette A, Peters B. The immune epitope database 2.0. Nucleic Acids Res. 2010 January; 38(Database issue):D854-62. Epub 2009 Nov. 11) to ensure that none of the sequences contain any known human B- or T-cell epitopes (sequence identity of 70% used as cut-off for the results obtained through BLAST search and considering only the results from human species).

5. Original Sequences of Murine F151 Variable Domains

CDRs are highlighted in bold and Vernier regions (as defined in Foote & Winter, J. Mol. Biol., 1992, 224, 487-499) are underlined.

```
Light Chain
                                       (SEQ ID NO: 26)
DIVMSQSPSS LAVSVGEKVTMSCKSSQSLLYSSNQKNYLA

WYQQKPGQSP KPLIYWASTRESGVPDRFTGSGSGTDFTLT

ISSVKAEDLA IYYCQQYYSYPWTFGGGTKLEIK
Germinality index = 83% with
Z46615_1_V_X67858_1_J[V☐ IV-B3]

Heavy Chain (SEQ ID NO: 19):
EIQLQQSGPELVKPGTSVKVSCKASGYSFTDYNIYWVKQS

HGKSLEWIGY FDPYNGNTGYNQKFRGKATLTVDKSSSTAF

MHLSSLTSDDSAVYYCANYYRYDDHAMDYWGQGTSVTVSS
Germinality index = 62% with
Z12316_1_VX97051_4_D_X97051_5_J[VH1 1-18]
```

6. Engineered Sequences a) Background 5 versions for the light chain (LC1, LC2a, LC2b, LC3a, and LC3b) and 5 versions of the heavy chain (HC1, HC2a, HC2b, HC3a, and HC3b) were proposed.

LC1 contains 5 humanizing mutations identified using the 4D humanization protocol. LC2a introduced an additional 5 stabilizing mutations. LC2b added 1 Lysine mutations to help prevent aggregation. LC3a contains 15 mutations derived from grafting to the closest human germline sequence and retaining the murine CDR and Vernier zone residues. LC3b contained 16 mutations derived from CDR-grafting with one additional humanizing mutation.

HC1 has 6 humanizing mutations identified by the in-house protocol. HC2a introduced 5 additional stabilizing mutations while HC2b contains 6 additional stabilizing mutations as compared to HC1. HC2c contains 1 Lys mutation, in addition to the stabilizing mutations of HC2a, to help prevent aggregation. HC3a contains 19 mutations derived from grafting to the closest human germline sequence and retaining the murine CDR and Vernier zone residues. HC3b contains 25 mutations derived from CDR grafting.

6 combinations in total were proposed (summarized in Table 16):
- LC1×HC1 (mutations addressing humanization only)
- LC2a×HC2a (mutations addressing humanization and stabilization)
- LC2a×HC2b (mutations addressing humanization and stabilization)
- LC2b×HC2c (mutations addressing humanization, stabilization and "anti-aggregation")
- LC3a×HC3a (mutations addressing mostly humanization by grafting+Vernier)
- LC3b×HC3b (mutations addressing humanization by grafting)

TABLE 16

Summary of the 6 LC × HC combinations proposed

| | (LC1) Humanizing | (LC2a) Humanizing + stabilizing | (LC2b) Humanizing + stabilizing + anti-aggregation | (LC3a) Grafting With Vernier Regions | (LC3b) Grafting |
|---|---|---|---|---|---|
| (HC1) Humanizing | X | | | | |
| (HC2a) Humanizing + stabilizing | | X | | | |
| (HC2b) Humanizing + stabilizing | | X | | | |
| (HC2c) Humanizing + stabilizing + "anti-aggregation" | | | X | | |
| (HC3a) grafting | | | | X | |
| (HC3b) grafting | | | | | X |

TABLE 17

Mutations of the 5 LC variants of the anti-DAKD/KD F151 antibody

| Light Chain Sequential numbering | Light Chain Kabat Numbering | (LC1) Humanizing mutations | (LC2a) Humanizing + stabilizing mutations | (LC2b) Humanizing + stabilizing mutations + anti-aggregation mutations | (LC3a) Grafting CDRs + Vernier residues | (LC3b) Grafting CDRs only |
|---|---|---|---|---|---|---|
| Ser5 | Ser5 | | Thr | Thr | Thr | Thr |
| Ser9 | Ser9 | | | | Asp | Asp |
| Ala12 | Ala12 | | Ser | Ser | | |
| Val13 | Val13 | Ala | Ala | Ala | | |
| Val15 | Val15 | | | | Leu | Leu |
| Glu17 | Glu17 | Asp | Asp | Asp | | |
| Lys18 | Lys18 | Arg | Arg | Arg | Arg | Arg |
| Val19 | Val19 | | | | Ala | Ala |
| Met21 | Met21 | | Ile | Ile | Ile | Ile |
| Ser22 | Ser22 | | | | Asn | Asn |
| Gln48 | Gln42 | Lys | Lys | Lys | | |
| Ser49 | Ser43 | | | | Pro | Pro |
| Pro52 | Pro46 | | | | | Leu |
| Thr69 | Thr63 | | Ser | Ser | Ser | Ser |
| Val84 | Val78 | | | | Leu | Leu |
| Lys85 | Lys79 | Gln | Gln | Gln | Gln | Gln |
| Leu89 | Leu83 | | | Lys | Val | Val |
| Ile91 | Ile85 | | Thr | Thr | Val | Val |
| Gly106 | Gly100 | | | | Gln | Gln |
| Leu110 | Leu104 | | | | Val | Val |
| Mutations: | | 5 | 10 | 11 | 15 | 16 |

TABLE 18

Mutations of the 6 HC variants of the anti-DAKD/KD F151 antibody

| Heavy Chain Sequential numbering | Heavy Chain Kabat numbering | (HC1) Humanizing mutations | (HC2a) Humanizing + stabilizing mutations | (HC2b) Humanizing stabilizing mutations | (HC2c) humanizing + stabilizing mutations + antiaggregation mutations | (HC3a) Grafting CDRs + Vernier residue | (HC3b) Grafting CDRs only |
|---|---|---|---|---|---|---|---|
| Glu1 | Glu1 | | Gln | Gln | Gln | Gln | Gln |
| Ile2 | Ile2 | | | | | | Val |
| Gln5 | Gln5 | Val | Val | Val | Val | Val | Val |
| Pro9 | Pro9 | | Ala | Ala | Ala | Ala | Ala |
| Leu11 | Leu11 | Val | Val | Val | Val | Val | Val |
| Val12 | Val12 | Lys | Lys | Lys | Lys | Lys | Lys |
| Thr16 | Thr16 | Ala | Ala | Ala | Ala | Ala | Ala |
| Lys38 | Lys38 | | | | | Arg | Arg |
| Ser40 | Ser40 | | | | | Ala | Ala |
| His41 | His41 | Pro | Pro | Pro | Pro | Pro | Pro |
| Lys43 | Lys43 | | | | | Gln | Gln |
| Ser44 | Ser44 | | Gly | Gly | Gly | Gly | Gly |
| Ile48 | Ile48 | | | | | | Met |
| Gln62 | Gln61 | | | Glu | | | |
| Lys67 | Lys66 | | | | | Arg | Arg |
| Ala68 | Ala67 | | | | | | Val |
| Leu70 | Leu69 | | | | | | Met |
| Val72 | Val71 | | | | | | Thr |
| Lys74 | Lys73 | | | | | | Thr |
| Ser76 | Ser75 | | | | | Thr | Thr |
| Phe80 | Phe79 | | Tyr | Tyr | Tyr | Tyr | Tyr |
| His82 | His81 | | | | | Glu | Glu |
| Ser84 | Ser82A | | | | | Arg | Arg |
| Leu 86 | Leu82C | | | | Lys | | |
| Thr87 | Thr83 | | | | | Arg | Arg |
| Asp89 | Asp85 | Glu | Glu | Glu | Glu | | |
| Asp90 | Asp86 | | Glu | Glu | Glu | | |
| Ser91 | Ser87 | | | | | Thr | Thr |
| Ser115 | Ser108 | | | | | Leu | Leu |
| Mutations: | | 6 | 11 | 12 | 12 | 19 | 25 | a) Engineered Light Chain Sequences:

No potentially problematic known T-cell or B-cell epitopes were found in all the variants proposed. LC1 (SEQ ID NO:27), humanizing mutations are underlined, CDRs and vernier zones are in bold:

```
DIVMSQSPSSLAASVGDRVTMSCKSSQSLLYSSNQKNYLA

WYQQKPGKSP KPLIYWASTRESGVPDRFTGSGSGTDFTLT

ISSVQAEDLAIYYCQQYYSYPWTFGGGTKLEIK
```

LC2a (SEQ ID NO:28), humanizing mutations are underlined, CDRs and vernier zones are in bold, stabilization mutations are in italics (T at position 5, S at position 12, I at position 21, S at position 69, T at position 91 shown below):

```
DIVMTQSPSSLSASVGDRVTISCKSSQSLLYSSNQKNYLA

WYQQKPGKSPKPLIYWASTRESGVPDRFSGSGSGTDFTLT

ISSVQAEDLA TYYCQQYYSYPWTFGGGTKLEIK
```

LC2b (SEQ ID NO:29) humanizing mutations are underlined, CDRs and vernier zones are in bold, stabilization mutations are in italics (T at position 5, S at position 12, I at position 21, S at position 69, T at position 91 shown below) and an anti-aggregation mutation is K at position 89:

```
DIVMTQSPSSLSASVGDRVTISCKSSQSLLYSSNQKNYLA

WYQQKPGKSPKPLIYWASTRESGVPDRFSGSGSGTDFTLT

ISSVQAEDKA TYYCQQYYSYPWTFGGGTKLEIK
```

LC3a (SEQ ID NO:30), grafted mutations shown in underline and CDRs and vernier zones shown in bold:

```
DIVMTQSPDSLAVSLGERATINCKSSQSLLYSSNQKNYLA

WYQQKPGQPPKPLIYWASTRESGVPDRFSGSGSGTDFTLT

ISSLQAEDVAVYYCQQYYSYPWTFGQGTKVEIK
```

LC3b (SEQ ID NO:31), grafted mutations shown in underline and CDRs and vernier zones shown in bold:

```
DIVMTQSPDSLAVSLGERATINCKSSQSLLYSSNQKNYLA

WYQQKPGQPPKLLIYWASTRESGVPDRFSGSGSGTDFTLT

ISSLQAEDVAVYYCQQYYSYPWTFGQGTKVEIK
```

Note that L at position 52 is a vernier residue that is mutated to human.

c) Engineered Heavy Chain Sequences

HC1 (SEQ ID NO:20), humanizing mutations are underlined, CDRs and vernier zones are in bold:

```
EIQLVQSGPEVKKPGASVKVSCKASGYSFTDYNIYWVKQS

PGKSLEWIGYFDPYNGNTGYNQKFRGKATLTVDKSSSTAF

MHLSSLTSEDSAVYYCANYYRYDDHAMDYWGQGTSVTVSS
```

HC2a (SEQ ID NO:21), humanizing mutations are underlined, CDRs and vernier zones are in bold, stabilization mutations are in italics (Q at position 1, A at position 9, G at position 44, Y at position 80 and E at position 90 shown below):

```
QIQLVQSGAEVKKPGASVKVSCKASGYSFTDYNIYWVKQS

PGKGLEWIGYFDPYNGNTGYNQKFRGKATLTVDKSSSTAY

MHLSSLTSEESAVYYCANYYRYDDHAMDYWGQGTSVTVSS
```

HC2b (SEQ ID NO:22), humanizing mutations are underlined, CDRs and vernier zones are in bold, stabilization mutations are in italics (Q at position 1, A at position 9, G at position 44, E at position 62, Y at position 80 and E at position 90 shown below):

```
QIQLVQSGAEVKKPGASVKVSCKASGYSFTDYNIYWVKQS

PGKGLEWIGYFDPYNGNTGYNEKFRGKATLTVDKSSSTAY

MHLSSLTSEESAVYYCANYYRYDDHAMDYWGQGTSVTVSS
```

No human epitopes were identified for sequence HC2b in IEDB database.

HC2c (SEQ ID NO:23), humanizing mutations are underlined, CDRs and vernier zones are in bold, stabilization mutations are in italics (Q at position 1, A at position 9, G at position 44, Y at position 80 and E at position 90 shown below) and an anti-aggregation mutation at K at position 86:

```
QIQLVQSGAEVKKPGASVKVSCKASGYSFTDYNIYWVKQS

PGKGLEWIGYFDPYNGNTGYNQKFRGKATLTVDKSSSTAY

MHLSSKTSEESAVYYCANYYRYDDHAMDYWGQGTSVTVSS
```

HC3a (SEQ ID NO:24), grafted mutations shown in underline and CDRs and vernier zones shown in bold:

```
QIQLVQSGAEVKKPGASVKVSCKASGYSFTDYNIYWVRQA

PGQGLEWIGYFDPYNGNTGYNQKFRGRATLTVDKSTSTAY

MELRSLRSDDTAVYYCANYYRYDDHAMDYWGQGTLVTVSS
```

LC3b (SEQ ID NO:25), grafted mutations shown in underline and CDRs and vernier zones shown in bold:

```
QVQLVQSGAEVKKPGASVKVSCKASGYSFTDYNIYWVRQA

PGQGLEWMGYFDPYNGNTGYNQKFRGRVTMTTDTSTSTAY

MRLRSLRSDDTAVYYCANYYRYDDHAMDYW

GQGTLVTVSS
```

Note that the following Vernier Residue are mutated to human: V at position 2, M at position 48, V at position 68, M at position 70 and T at position 74.

No human epitopes were identified for sequence HC3b in IEDB database.

HC3b germinality index=83% with Z12316_1_V_J00235_1_D_U42590_1_J[1-18/DP-14].

TABLE 19

Stabilizing Changes Proposed in Light Chain

| Residue | Proposed Change | Calculated ΔΔGth | Accept Change |
|---|---|---|---|
| Ser-5 | Thr | 2.32286 | Yes |
| Ala-12 | Ser | 0.75228 | Yes |
| Met-21 | Ile | 0.768959 | Yes |
| Pro-52 | Leu | 1.70059 | No - Vernier region |
| Thr-69 | Ser | 1.10843 | Yes |
| Lys-86 | Glu | 2.00115 | No - changed to Gln during humanization |
| Ile-91 | Thr | 1.27255 | Yes |

TABLE 20

Stabilizing Changes Proposed in Heavy Chain

| Residue | Proposed Change | Calculated ΔΔGth | Accept Change |
|---|---|---|---|
| Glu-1 | Gln | 0.562423 | Yes |
| Ile-2 | Val | 2.15882 | No - Vernier region |
| Pro-9 | Ala | 0.505324 | Yes |
| Thr-16 | Ala | 1.50552 | Already changed to Ala in humanization |
| Val-20 | Leu | 2.21586 | No - not in germline sequence |
| Ser-40 | Arg | 1.03643 | No - not in germline sequence |
| His-41 | Pro | 1.67738 | Already changed to Pro in humanization |
| Ser-44 | Gly | 1.5068 | Yes |
| Gln-62 | Glu | 0.74934 | No - not in germline sequence |
| Arg-65 | Lys | 2.32314 | No - not in germline sequence |
| Phe-80 | Tyr | 1.30935 | Yes |
| His-82 | Gln | 2.24674 | No - not in germline sequence |
| Asp-89 | Glu | 1.65409 | Already changed to Glu in humanization |
| Asn-98 | Arg | 3.65643 | No - Vernier region |

TABLE 21

Combinations of stabilizing mutations evaluated

| Combination* | Additional changes suggested | Accept Change |
|---|---|---|
| L1 (46->P & 48->Q) | K48->Q | No - K48 humanizing mutation |
| L2 (51->K) | None - already K51 | None |
| L3 (80->T) | None - already T80 | None |
| L4 (82->S) | None - already S82 | None |
| L5 (90->A, 91->T) | None - already A90, T91 suggested above (Table 1) | None |
| H1 (15->G) | None - already G15 | None |
| H2 (62->E, 63->K, 64->F) | Q62->E, already K63 and F64 | Yes - considered in HC2b |
| H3 (87->T, 88->S, 89->D) | D89->E, already T87 and S88 | Yes - potential salt bridges with K63 and K43 |
| S1 (L1 & L5) | K48->Q | No - K48 humanizing mutation |
| S2 (H1 & H3) | D89->E | No (see H3) |

*Note:
Sequential numbering used to refer to residues

TABLE 22

Potential Stabilizing Mutations

| Light Chain Residue* | Additional changes suggested | Accept Change |
|---|---|---|
| 15->L | V15->L | No - V15 in Vk1 germline |
| 96->Q | None - already Q96 | None |
| 38->Y | None - already Y38 | None |
| 112->I | None - already I112 | None |
| 69->S | G69->S | No - G69 is in Vernier Region |
| 21->I | M21->I | Already changed (see Table 19) |

*Note:
Sequential numbering used to refer to residues

Example 6: Characterization of Humanization Variants

Based on the in silico modeling presented in Table 16, the variable region of the light chain (VL) and heavy chain (VH) DNA of humanized F151 were codon optimized for HEK293 expression and gene synthesized by GeneArt (subsidiary of Life Technologies). The synthesized DNA fragments were cloned into the constant region of the light chain (CL) encoding vectors, pFF0362 (A. Human Kappa LC vector) at ApaLI/BsiWI sites and the constant regions of the heavy chain (CH1, CH2 and CH3) encoding vectors, pFF0363 (B. Human IgG1 HC vector) at ApaLI/ApaI sites respectively. The resulted plasmids pFF0460 containing the full sequence of LC and pFF0466 containing the full length of HC of humanized F151 variants were co-transfected and transiently expressed in FreeStyle™ 293 Expression System (Invitrogen/Life Technologies, catalog no. K9000-01).

The six humanized variants shown in Table 16 were characterized by various parameters such as binding kinetics (discussed above) as well as chemical and physical properties such as thermostability that are routinely used in the art.

Figure 2:
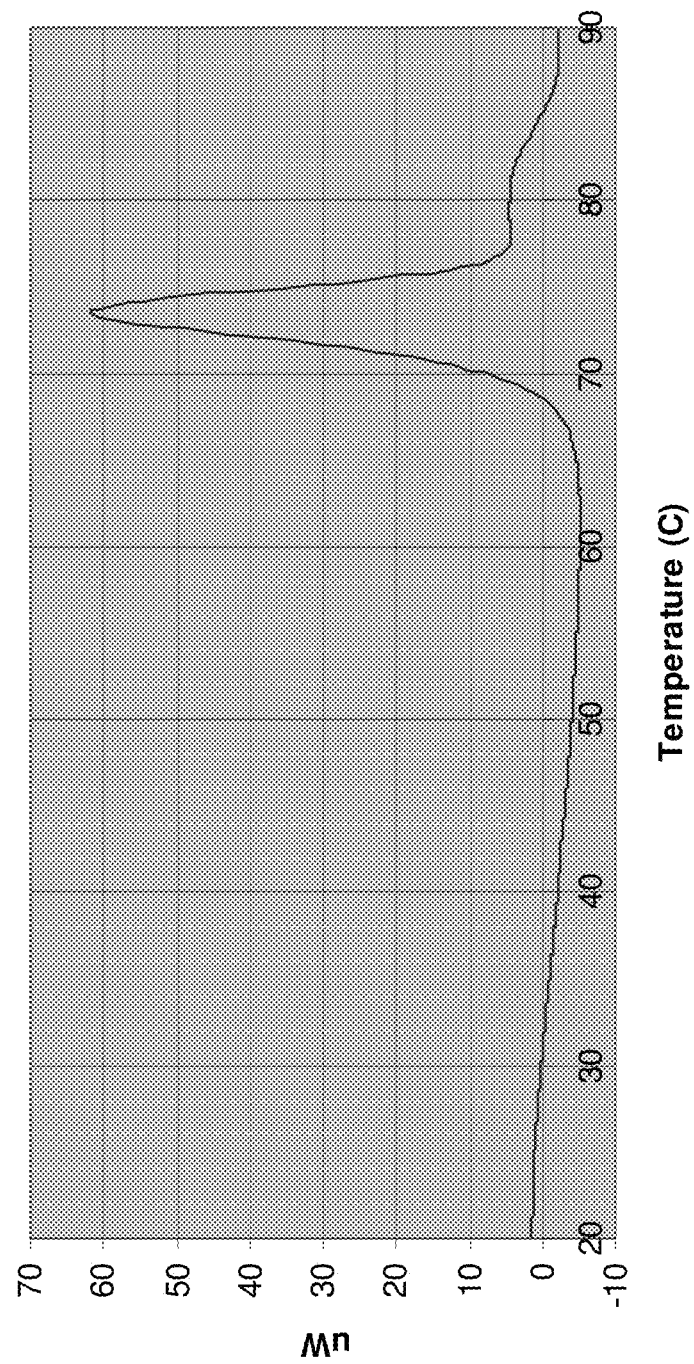
FIG. 2 depicts the results of differential scanning calorimetry measurements of antibody F151.

The characterization was done in two tiers. Tier I included differential scanning calorimetry (DSC) shown in Table 24 and FIG. 2. Briefly, for the DCS experiments, the antibodies were dialyzed against phosphate-buffered saline solution. Antibody concentrations were measured by UV absorbance. The antibodies were diluted to 1 mg/mL using PBS. Scans were performed using a calorimetry Sciences Corporation N-DSC II instrument using a 0.3268 mL capillary cell with PBS in the reference cell. The scan rate was 2° C./min and the samples were scanned from 20° C. to 100° C.

All variants, except for HC3b/LC3b showed comparable binding affinities to the parental antibody. Variant HC3a/LC3a was selected over the other variants based on other physiochemical properties such as SEC data, stability and lack of aggregation (see Tables 23-25).

TABLE 23

Comparison of Kinetics of the Humanized F151 Variants

|  | Ka (1/Ms) | Kd (1/s) | KD (M) | Ka (1/Ms) | Kd (1/s) | KD (M) |
|---|---|---|---|---|---|---|
|  | HC1/LC1 | | | HC2a/LC2a | | |
| DAKD-b | 4.16E+05 | 6.00E−06 | 1.45E−11 | 6.66E+05 | 1.22E−05 | 1.83E−11 |
| KD-b | 4.24E+05 | 1.74E−07 | 3.94E−13 | 7.03E+05 | 6.12E−06 | 8.71E−12 |
| DAKLP-b | 5.00E+05 | 7.96E−06 | 1.60E−11 | 4.10E+05 | 5.67E−06 | 1.38E−11 |
| KLP-b | 4.81E+05 | 2.67E−06 | 5.54E−12 | 6.15E+05 | 2.68E−05 | 4.34E−11 |
|  | HC2b/LC2a | | | HC2c/LC2b | | |
| DAKD-b | 4.17E+05 | 1.05E−05 | 2.57E−11 | 4.81E+05 | 4.34E−05 | 9.01E−11 |
| KD-b | 3.75E+05 | 1.66E−06 | 4.72E−12 | 5.64E+05 | 9.08E−06 | 1.74E−11 |
| DAKLP-b | 4.46E+05 | 1.30E−05 | 2.97E−11 | 9.03E+05 | 1.10E−05 | 1.21E−11 |
| KLP-b | 4.01E+05 | 2.20E−06 | 5.76E−12 | 5.16E+05 | 1.02E−05 | 1.98E−11 |
|  | HC3a/LC3a | | | HC3b/LC3b | | |
| DAKD-b | 5.06E+05 | 1.28E−05 | 2.53E−11 | 3.85E+05 | 5.15E−05 | 1.35E−10 |
| KD-b | 4.27E+05 | 2.95E−06 | 6.78E−12 | 2.51E+05 | 3.02E−06 | 1.44E−11 |
| DAKLP-b | 4.65E+05 | 1.42E−05 | 3.05E−11 | 7.04E+04 | 2.76E−03 | 4.05E−08 |
| KLP-b | 5.02E+05 | 5.43E−07 | 1.06E−12 | 5.39E+05 | 2.72E−04 | 5.26E−10 |

For comparison: Ka (1/Ms) of mF151 was 7.84E+05 for DAKD-b, 8.30E+05 for KD-b, 1.81E+06 for DAKLP-b, and 1.12E+06 for KLP-b

TABLE 24

Tier 1 comparison of humanization variants

| Variant | Protein Conc. (mg/ml) UV Spectroscopy (A280) | Purity 1D-gel (reducing & non-reducing) | SEC | Stability DSC (Tm ° C.) (Tm of parental F151 = 73° C.) | Functional Potency Assay FDSS Assay | FDSS Assay without preincubation | Ligand Affinity Biacore Binding |
|---|---|---|---|---|---|---|---|
| HC1/ LC1 | 1.69 | No Ag/Deg | ≈5% Ag | 81.6 (M) 70.0 (m) | nM potency at DAKD, sub nM | Active at DAKD and KD | Kon 10E5, koffless than or equal |

TABLE 24-continued

Tier 1 comparison of humanization variants

| | Test | | | | | |
|---|---|---|---|---|---|---|
| | Protein Conc. (mg/ml) | Purity | | Stability | Functional Potency Assay | Ligand Affinity |
| | | | | Method | | |
| Variant | UV Spectroscopy (A280) | 1D-gel (reducing & non-reducing) | SEC | DSC (Tm ° C.) (Tm of parental F151 = 73° C.) | FDSS Assay | FDSS Assay without preincubation | Biacore Binding |
| HC2a/LC2a | 2.01 | No Ag/Deg | No Ag | 75.0 (M) 82.5 (m) | potency at KD, comparable among 5 variants | comparable among 5 variants | to 10E−6 comparable among 5 variants |
| HC2b/LC2a | 1.83 | No Ag/Deg | No Ag | 74.6 (M) 83.0 (m) | | | |
| HC2c/LC2b | 0.68 | No Ag/Deg | No Ag | 71.0 (M) 64.0 (m) 82.5 (m) unstable | | | |
| HC3a/LC3a | 1.71 | No Ag/Deg | No Ag | 82.3 (M) 71.8 (m) Most Stable | | | |
| HC3b/LC3b | 1.47 | No Ag/Deg | No Ag | 79.4 (M) 71.4 (m) | Lost potency to KLP & DAKLP | | Decreased affinity to KLP & DAKLP |

Abbreviations:
Ag = aggregation,
Deg = degradation

TABLE 25

Tier 2 comparison of humanization variants

| Variant | Thermostability | | | Stability | Intactness Confirmation (LC, HC) | N-terminal sequence confirmation N-terminal |
|---|---|---|---|---|---|---|
| | 1D-gel | SEC | Biacore | SEC | LC-MS | sequencing |
| HC1/LC1 | No Ag/Deg | No Ag/Deg | 45 C. slightly faster off rate than 4 C. | No Ag/Deg | LC (+1Da off) HC (+1Da off) G0 dominant | N terminal of LC & HC intact |
| HC2a/LC2a | No Ag/Deg | No Ag/Deg | 45 C. slightly faster off rate than 4 C. | No Ag/Deg | LC (spot on) HC (spot on) G0 dominant | N terminal of LC & HC intact |
| HC2b/LC2a | No Ag/Deg | No Ag/Deg | 45 C. slightly faster off rate than 4 C. | No Ag/Deg | LC (+1Da off) HC (+1Da off) G0 dominant | N terminal of LC & HC intact |
| HC2c/LC2b | X | X | X | X | X | X |
| HC3a/LC3a | No Ag/Deg | No Ag/Deg | 45 C. slightly faster off rate than 4 C. | No Ag/Deg | LC (−2Da off) HC (−2Da off) G0 dominant | N terminal of LC & HC intact |
| HC3b/LC3b | X | X | X | X | X | X |

Thermostability = Incubation at 4° C. (control) and 45° C. for 3 days;
1D-gel was under non-reducing conditions;
Stability = 2 cycles of freeze/thaw;
LC-MS = reduced and reduced/deglycosylation
Abbreviations:
Ag = aggregation,
Deg = degradation,
X = no data presented

TABLE 26

Comparison of Parental F151 and humanized variant F151 (HC3a/LC3a)

| | Variable Heavy Chain | Variable Light Chain |
|---|---|---|
| | Parental F151 | |
| Gene | GAGATCCAGCTGCAGCAGTCTGGACCTGAGCTG GTGAAGCCTGGGACTTCAGTGAAGGTGTCCTGC AAGGCTTCTGGTTACTCATTCACTGACTACAAC ATCTACTGGGTGAAACAGAGCCATGGAAAGAGC CTTGAGTGGATTGGATATTTTGATCCTTACAAT GGTAATACTGGCTACAACCAGAAGTTCAGGGGC AAGGCCACATTGACTGTTGACAAGTCCTCCAGC ACAGCCTTCATGCATCTCAGCAGCCTGACATCT GATGACTCTGCAGTCTATTACTGTGCAAACTAC TATAGGTATGACGACCATGCTATGGACTATTGG GGTCAAGGAACCTCAGTCACCGTCTCCTCA (SEQ ID NO: 127) | GACATTGTGATGTCACAGTCTCCATCCT CCCTAGCTGTGTCAGTTGGAGAGAAGGT TACTATGAGCTGCAAGTCCAGTCAGAGC CTTTTATATAGTAGCAATCAAAAGAACT ACTTGGCCTGGTACCAGCAGAAACCAGG GCAGTCTCCTAAACCGCTGATTTACTGG GCATCCACTAGGGAATCTGGGGTCCCTG ATCGCTTCACAGGCAGTGGATCTGGGAC AGATTTCACTCTCACCATCAGCAGTGTG AAGGCTGAAGACCTGGCAATTTATTACT GTCAGCAATATTATAGCTATCCGTGGAC GTTCGGTGGAGGCACCAAGCTGGAAATC AAA (SEQ ID NO: 128) |
| Protein | EIQLQQSGPELVKPGTSVKVS<u>CKAS<u>GYSFTDYN</u> IYW</u>VKQSHGKS<u>LEWIGYFDPYNGNTGYNQKFRG KAT</u>LTVDKSSSTAFMHLSSLTSDDSAVYY<u>C</u>ANY YRYDDHAMDYWG<u>Q</u>GTSVTSS (SEQ ID NO: 19) | DIVMSQSPSSLAVSVGEKVTMS<u>CKSSQSL LYSSNQKNYLA</u>W<u>YQQKPGQSPKPLIYWA STRES</u>GVPDRFTGSGSGTDFTLTISSVK AEDLAIYY<u>C</u>QQYYSYPWT<u>F</u>GGGTKLEIK (SEQ ID NO: 26) |
| | Humanized F151 (HC3a/LC3a) | |
| Gene | CAGATTCAGCTGGTGCAGTCTGGCGCCGAAGTG AAGAAACCTGGCGCCAGCGTGAAGGTGTCCTGC AAGGCCAGCGGCTACAGCTTCACCGACTACAAC ATCTACTGGGTCCGACAGGCTCCAGGCCAGGGA CTGGAATGGATCGGCTACTTCGACCCCTACAAC GGCAACACCGGCTACAACCAGAAGTTCCGGGGC AGAGCCACCCTGACCGTGGACAAGAGCACCAGC ACCGCCTACATGGAACTGCGGAGCCTGAGAAGC GACGACACCGCCGTGTACTACTGCGCCAACTAC TACAGATACGACGACCACGCCATGGACTACTGG GGCCAGGGCACCCTGGTCACCGTGTCCTCT (SEQ ID NO: 129) | GACATCGTGATGACCCAGAGCCCCGACA GCCTGGCCGTGTCTCTGGGCGAGCGGGC CACCATCAACTGCAAGAGCAGCCAGAGC CTGCTGTACTCTAGCAACCAGAAGAACT ACCTGGCCTGGTATCAGCAGAAGCCCGG CCAGCCCCCAAGCCCCTGATCTACTGG GCCAGCACCCGCGAGAGCGGCGTGCCCG ATAGATTTTCCGGCAGCGGCTCCGGCAC CGACTTCACCCTGACCATCAGCAGCCTG CAGGCCGAGGACGTGGCCGTGTACTACT GCCAGCAGTACTACAGCTACCCCTGGAC CTTCGGCCAGGGCACCAAGGTGGAAATC AAG (SEQ ID NO: 130) |
| Protein | QIQLVQSGAEVKKPGASVKVS<u>CKAS<u>GYSFTDYN</u> IYW</u>VRQAPGQG<u>LEWIGYFDPYNGNTGYNQKFRG RAT</u>LTVDKSTSTAYMELRSLRSDDTAVYY<u>C</u>ANY YRYDDHAMDYWG<u>Q</u>GTLVTVSS (SEQ ID NO: 24) | DIVMTQSPDSLAVSLGERATIN<u>CKSSQS LLYSSNQKNYLA</u>W<u>YQQKPGQPPKPLIYW ASTRES</u>GVPDRFSGSGSGTDFTLTISSL QAEDVAVYY<u>C</u>QQYYSYPWT<u>F</u>GQGTKVEI K (SEQ ID NO: 30) |

Single underscore = CDR region;
double underscore = signature amino acids for identifying CDRs For alignment of light and heavy chains of parental F151 to humanized F151 variant (HC3a/LC3a), see FIG. 3.

Example 7: Crystal Structure of Humanized Antibody F151 against BRK1 Ligand Kallidan and des-arg[10]-Kallidin The crystal structures of humanized F151 (HC3a/LC3a) Fab bound to kallidan or des-arg[10]-kallidin was determined and the molecular interactions analyzed.

Kallidin powder was purchased from Phoenix Pharmaceuticals (Cat. No. 009-37). For Fab protein generation, the DNA of heavy chain (HC) VH region from humanized F151 HC3a was cloned into 6×His tagged CH1 vector pFF0366 ("6×His" disclosed as SEQ ID NO: 137). The light chain (LC) plasmid used here was the same as of the original F151 LC3a used in F151 humanization (see Example 5). The two plasmids were co-transfected into free style HEK293 cells for Fab expression. The Fab protein was purified using cobalt-resin, buffer exchanged to 50 mM MES pH6.0, 50 mM NaCl before being concentrated to about 9 mg/mL. Purified F151 Fab protein was mixed with kallidin in a molar ratio of 1:2 and set up for crystallization screening. Crystallization screening was done with a wide range of conditions. The best crystal was observed under condition B10, B12 and G10 of Hampton Research screening kit PEG/ION HT. The crystals were cryo-protected with 20% glycerol in well buffer and frozen for diffraction data collection. The X-ray diffraction data for both complexes were collected at Canadian Light Source, beamline CMCF-08ID. The Rmerge for the F151-KD complex is 8.9% and l/s(l)=20.2, while those for the F151-DAKD are 7.7% and 18.5, respectively. The F151-KD structure was solved by molecular replacement in Phaser using Fab coordinates from PDB entry 3QOS, treating the $V_L$-$V_H$ and $C_L$-$C_H1$ domains as independent units. The structure was refined in autoBuster at 2.07 Å resolution in space group $P2_12_12_1$ to an Rfactor of 0.205 and an Rfree of 0.228. The F151-DAKD structure was solved using the F151-KD coordinates. The structure was refined in autoBuster at 1.86 Å resolution in space group P212121 to an Rfactor of 0.232 and an Rfree of 0.238.

Figure 4:
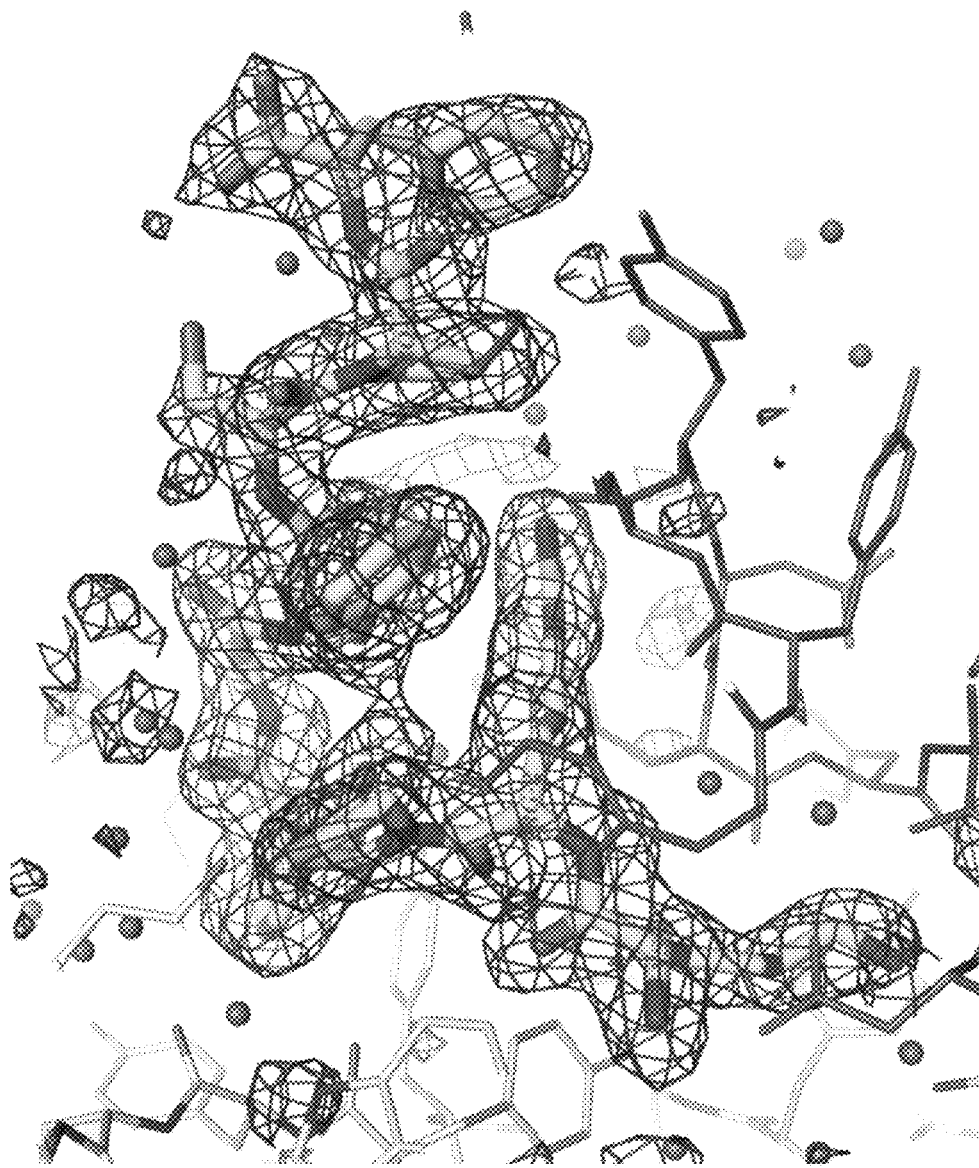
FIG. 4 depicts an electron density map of the antigen binding site of the F151 antibody/kallidin complex.
Figure 5:
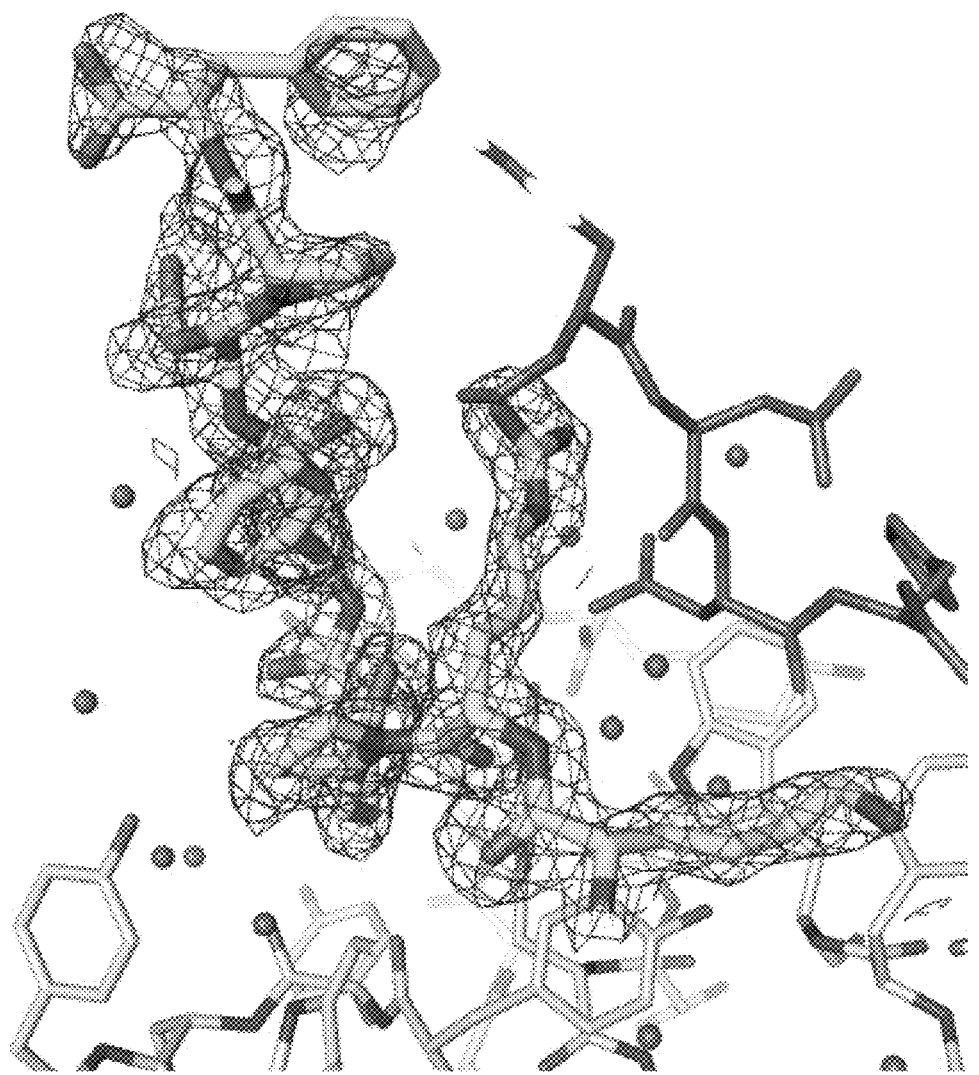
FIG. 5 depicts an electron density map of the antigen binding site of the F151 antibody/des-Arg10-kallidin complex.

The electron density maps shown in FIGS. 4 and 5 depict the binding of kallidin (KD) and Des-Arg$^{10}$-kallidin (DAKD) to the F151 Fab and unambiguously determine the positions of each amino acid. For kallidin, the electron density for the extreme C-terminal residue Arg$^{10}$ is not present. This is in agreement with the observation that DAKD, which is missing the C-terminal residue arginine (shown in Table 27 below), binds equally well to F151 as KD. The IC50 values of F151 in the neutralization FDSS cellular assay towards KD and DAKD are 0.12 nM and 0.09 nM, respectively. In both cases the electron density is weaker towards the C-termini of the peptides. Since Phe$^9$ in KD has slightly better electron density than that in DAKD, it is possible that the presence of the additional arginine at the C-terminus of KD stabilizes the C-terminus of this peptide when binding to F151 although this arginine itself is not stable enough to be observed by X-ray. Since the two structures are essentially identical (rms between KD and DAKD is 0.139 for C atoms and 0.328 for all atoms), all the following discussions are based on the F151-KD structure.

C63 is particularly interesting in its heavy chain, that the loop length in H2 and H3 are more different from all others. Considering the Fab as a whole, B21 and I54 were most closely related.

In the crystal structure, we found that KD is involved in systematic hydrogen bond and hydrophobic interactions with the Fab. The N-terminus of KD is buried in the Fab and harbors more intensive interactions, while the C-terminus is essentially solvent exposed. Except for the first 4 residues (Lys-Arg-Pro-Pro) (SEQ ID NO: 132), the other residues of KD gradually extend into the bulk solvent. The amidinium group of Lys1 sidechain is anchored by Glu-L61 (L: light chain) through salt bridges, while the amino terminal amino group Lys 1 forms a salt bridge with Asp-H108 (H: heavy chain). The amidinium group of Lys1 sidechain also hangs over the aromatic ring of Tyr-L55, involved in cation interactions. Such intensive interactions involved with Lys1 tightly anchor the amino terminus of KD in the Fab. This also accounts for the importance of Lys1 in the binding of KD to F151. Without it (i.e. bradykinin), no detectable

TABLE 27

A selected list of kinin peptides

| Peptide name | SEQ ID NO: | Sequence 1 2 3 4 5 6 7 8 9 10 |
|---|---|---|
| KD (Kallidin) | 1 | Lys-Arg-Pro-Pro-Gly-Phe-Ser-Pro-Phe-Arg |
| DAKD (des-Arg$^{10}$-Kallidin) | 2 | Lys-Arg-Pro-Pro-Gly-Phe-Ser-Pro-Phe |
| KLP (rodent KD ortholog) | 3 | Arg-Arg-Pro-Pro-Gly-Phe-Ser-Pro-Phe-Arg |
| BK (Bradykinin) | 5 | Arg-Pro-Pro-Gly-Phe-Ser-Pro-Phe-Arg |

Figure 6:
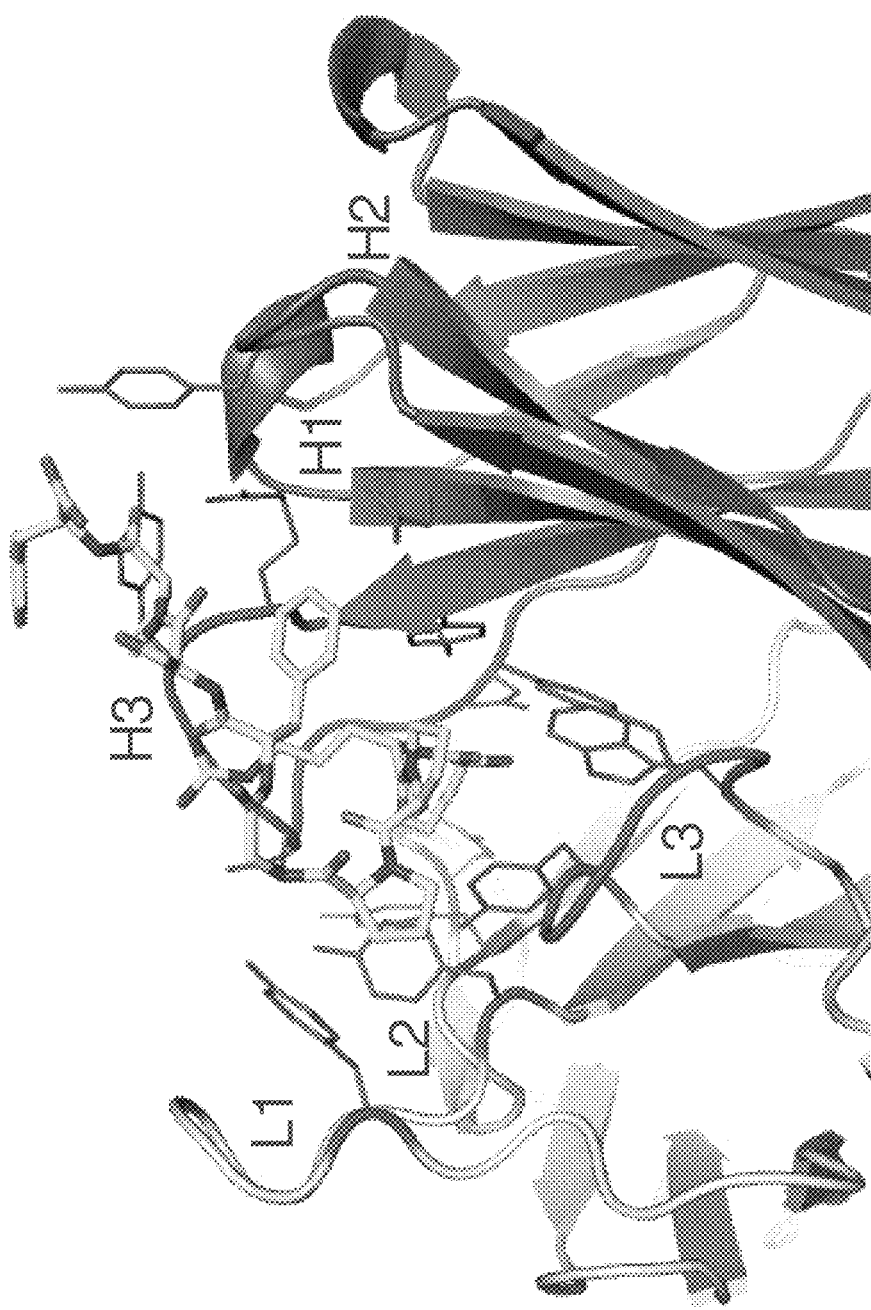
FIG. 6 depicts a ribbon and stick representation of the Fv subunit of F151 bound to kallidin.
Figure 7:
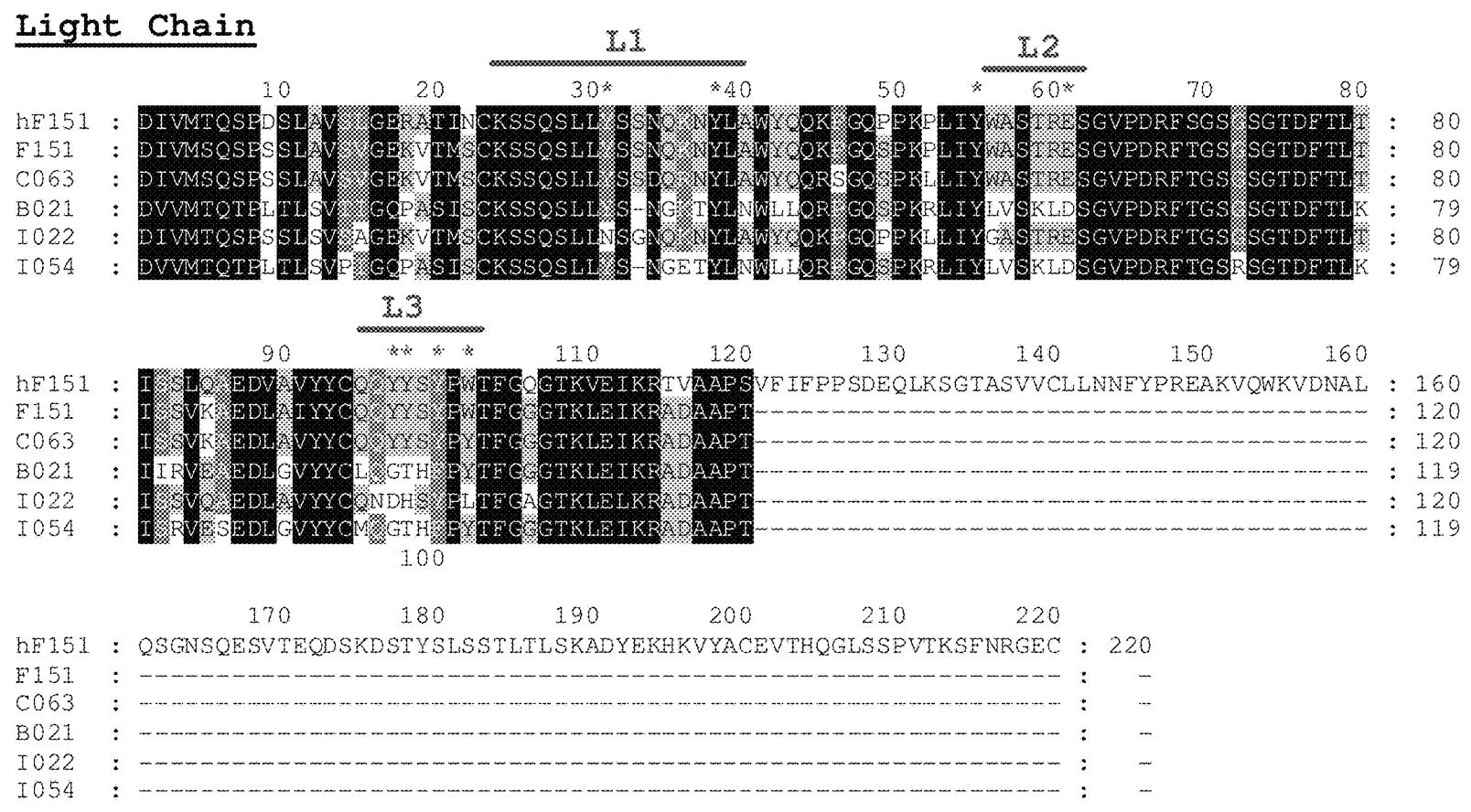
Figure 8:
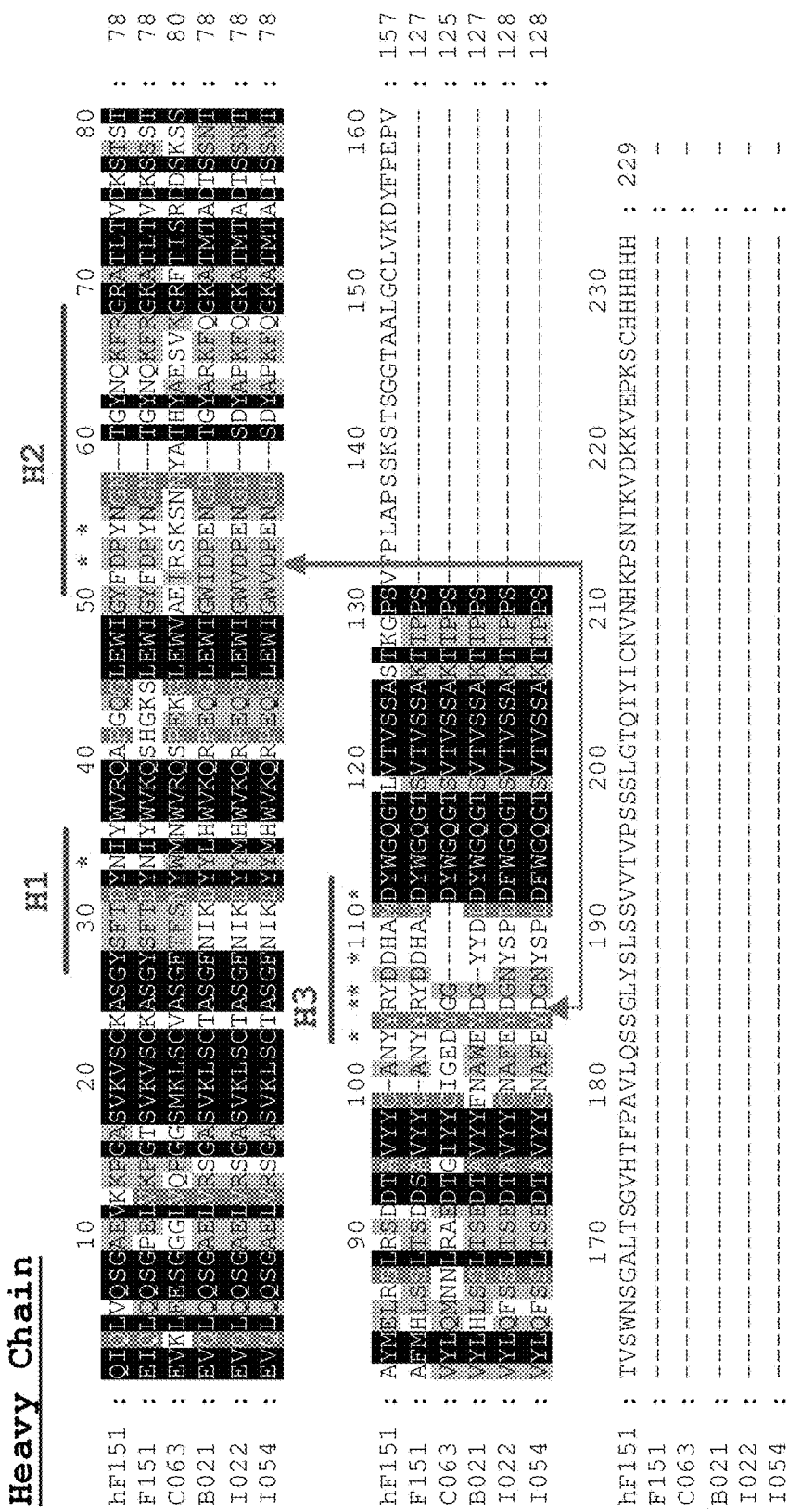
FIG. 8 depicts an amino acid sequence alignment of the heavy chain variable regions of exemplary murine anti-kallidin antibodies of the invention. Amino acid residues that interact with kallidin are marked with asterisks. Figure discloses SEQ ID NOS 135, 120, 119, 118, 121, and 122, respectively, in order of appearance.

KD is bound with its N-terminus buried in the interface between Fv subunits of the light and heavy chains, as shown in FIG. 6. The interface between light and heavy chains are packed with aromatic amino acids, including Tyr-L42, Tyr-L93, Tyr-L100, Trp_L102, Phe-L104 and Tyr-H35, Trp-H47, Tyr-H50, Tyr-H99, Trp-H110, stabilizing each other through stacking and hydrophobic interactions. Residues from each of the CDR's of light and heavy chains contribute to the binding. The residues along the light and heavy chains that are involved in interactions with KD as mapped on the CDRs are shown in FIGS. 7 and 8. CDR H3 of the heavy chain is the longest loop and the one most frequently used in the interactions with KD, forming a side cover for KD. The loop was stabilized mostly through interactions with the other two CDRs, H1 and H2 of the heavy chain, namely, Salt bridge between Asp-H101 and Arg-H52 (stabilizing H1 and H3), arene-H interaction between Tyr-H102 and Tyr-H54 (stabilizing H2 and H3), H-bond between Asp-H108 and Tyr-H35 and H-bond between His-H105 and Tyr-L55 (stabilizing H3 and L2).

Comparing the KD interacting residues among the antibodies generated, it can be seen that there is similarity among the antibodies, and some were more related in use of particular amino acids for KD-interaction than others. For example, in the light chain F151, C63 and I22 use more similar amino acids in their CDRs to bind KD, while B21 and I54 were more similar. In the heavy chain, F151 and C63 were surprisingly unique from each other and from B21, I22 and I54. The latter three appear to form a group in similarity.

binding to hF151 or F151 can be measured. Like Lys1, Arg2 interacts with the Fab through a salt bridge. The guanidium group of Arg2 interacts with the sidechain of Asp-H104. The sidechain of Arg2 is also H-bonded with the mainchain carbonyl oxygen of Arg-H101. Also, the mainchain oxygen of Pro8 is H-bonded to the sidechain of Arg-H101. Tyr-H102 is half-way intercalated into Phe8 and Pro9, involving in hydrophobic interactions with KD. In addition to direct interaction, numerous water-mediated H-bonds between KD and the Fab are also seen. It is also interesting to notice that tyrosine residues are most frequently used in the interaction compared to other amino acids; 9 out of the 16 residues marked with asterisks in FIGS. 7 and 8 are tyrosines. All the residues in F151 surrounding KD appear to play a role in ligand binding, except for Asn-H33, which is close to Phe6 sidechain but incompatible in polarity and lack of other important interactions. Substitution with aromatic/hydrophobic residues, such Trp or Tyr to interaction with Phe8 appears to be a quick pick if affinity maturation is considered. These two aromatic amino acids are in fact seen in other antibodies (Trp in C63, and Tyr in B21, I22, I54). Table 28 below provides a detailed analysis of 16 KD-interacting amino acid residues marked in FIGS. 7 and 8 and sets forth functional substitutions that can be made in the CDR regions that should not disrupt antigen binding.

TABLE 28

A list of amino acid residues found around the KD binding pocket, and their roles in KD binding and potential functional substitutions (light chain residues in grey-colored cells and heavy chain residues in unshaded cells)

| Residue | Role in KD Binding or CDR Stabilization | Functional Substitution |
| --- | --- | --- |
| Tyr-L31 | Edge-on hydrophobic interactions with Pro4<br>Along with Tyr-L38 and Tyr-L98 form three orthogonal planes that surround the 90deg turn of KD at Pro4 | His to add an H-bond with amide N of Pro5<br>other aromatic a.a, such as Trp, and Phe |
| Tyr-L38 | hydrophobic stacking with Pro4<br>Along with Tyr-L31 and Tyr-L98 form three orthogonal planes that surround the 90deg turn of KD at Pro4 | His to add an H-bond with carbonyl O of Arg2 |
| Tyr-L55 | cation-□ interaction with amidinium ion of Lys1 sidechain<br>H-bond with His-H105; Tyr-L55 --His-H105 pairing adds stabilization between L2 and H3 loops | Trp to pair with H105 mutations of Gln, Asn, Glu or Asp (maintaining H-bond); Other variants of His_H105 are Tyr and Ser.<br>Other aromatic a.a., such as Trp, His and Phe |
| Glu-L61 | Forming key salt bridges with Lys1 sidechain | Asp, Gln, ASN (Asp is seen in B21 and I54 already, FIG. 7) |
| Tyr-L97 | H-bond with amide N of Trp-L56<br>Forming pocket for Arg1 extended sidechain | Aromatic a.a. such as Phe or His (too tight space for Trp) |
| Tyr-L98 | Along with Tyr-L31 and Tyr-L38 form three orthogonal planes that surround the 90deg turn of KD at Pro4 | Other aromatic a.a, such as Phe, Trp or His |
| Tyr-L100 | Forming pocket surface for Pro3<br>Part of the aromatic a.a. cluster interface between L/H chains, further including Tyr-L42, Tyr-L93, Trp_L102, Phe-L104 and Tyr-H35, Trp-H47, Tyr-H50, Tyr-H99, Trp-H110<br>Partial stacking with Tyr-H50 | Aromatic a.a., such as Phe (better hydrophobic interactions with Pro3)<br>Other variants seen are Thr (in B21 and I54) and His (in I22) |
| Trp-L102 | Part of the aromatic a.a. cluster interface between L/H chains<br>Stacking with Trp-H47 | Other aromatic a.a, such as Tyr (in C63 and B21), Phe and His<br>Other hydrophobic residue, such as L (in I22) |
| Asn-H33 | Close to Phe6 sidechain but incompatible in polarity, no other roles seen either; can be a target for affinity maturation | Replace with aromatic/hydrophobic a.a., such as Trp (seen in C63) or Tyr (seen in B21, I22, I54) |
| Asp-H52 | Salt bridge with Arg-H101, stabilizing H1 and H3 loops | Mutate as a pair with Arg-H101 to reversely charged a.a., such Arg-H52/Asp-H101, or a pair of hydrophobic a.a. (Leu, Ile, Val, Met, Phe, Tyr, Trp, Ala) to form a cluster with Phe6 of KD |
| Tyr-H54 | Close to Pro8 but no specific interactions<br>Close to Arg-H101, but no charge interactions | Mutated to negatively charged a.a. to stabilize Arg-H101, such D or E (seen in B21, I22 and I54) or N or Q, also provide H-bond with carbonyl O of Pro8 (A Lys in C63, which can be charge-reversed to Glu) |
| Tyr-H99 | Part of aromatic interface between H and L chains<br>H-bond with Asn-H33<br>Tight space | Mutate to small aromatic a.a. except W, such as Phe and His |
| Arg-H101 | H-bond with amide of Pro8<br>supported by Asp-H52 (salt bridge) | Mutate as a pair with Asp-H52 to reversely charged a.a., such as Arg-H52/Asp-H101, or a pair of hydrophobic a.a. to form a cluster with Phe6 of KD |
| Tyr-H102 | Half-way intercalating into Phe9 and Pro8, hydrophobic interactions with KD | Phe can be better, Trp or His may be OK too |
| Asp-H104 | Key residue to salt-bridge with Arg2 | Glu to maintain salt bridge with Arg2<br>Bigger a.a to fill the gap from Pro3, such as Tyr as seen in B21, I22 and I54 |
| Asp-H108 | Key residue to salt bridge with N-term -NH3+ of KD<br>H-bond with Tyr-H33, stabilizing H3 loop<br>Conserved residue! Not in CDR | Glu |

Analysis of the conformational epitope of Kallidin (KD) or desArg10-Kallidin (DAKD) revealed that it adopts a "Pro4 kink" conformation. As depicted in FIG. 17, a hallmark of the "Pro4 kink" conformation is a type II tight turn in the main chain polypeptide backbone of KD or DAKD at Proline 4 (see Richardson J S. "The anatomy and taxonomy of protein structure." Adv Protein Chem. 1981; 34:167-339, which is incorporated by reference herein). The "Pro4 kink" conformation may further defined by all or substantially all of the remaining amino acids of KD (1-2 and 6-9) or DAKD adopting repeats of a sigmoid shape which align the hydrophobic side chains in a spatially stacking mode.

Example 8: In Vivo Pharmacology of Anti-BKR1-Ligand Antibodies in Pain Models

The examples of the present invention illustrate the in vivo efficacy of anti-BKR1 receptor-ligand antibodies in different preclinical models of acute and chronic pain according to modified procedures described in (a) Saddi G M and Abbott F V., Pain (2000), 89:53-63; (b) Chen et al., Molecular Pain (2010), 2:6-13 and (c) Bennett G J and Xie Y K., Pain (1988), 33:87-107.

Animals

Experiments were carried out using adult male OF1 mice (20-30 gr) for formalin studies and adult male C57Bl/6J mice (25-30 gr) for both CFA and CCI studies. The mice were kept in a controlled temperature room under a 12-h light-dark cycle. Food and water were provided ad libitum. For all of the experiments, mice were acclimatized to the laboratory room for at least 2 hours before testing. No randomization was performed for the studies. Experimenters performing the behavioral tests were not blind to treatment; however they were not aware of the study hypothesis. All procedures have been approved by the "Comité d'Expérimentation pour la Protection de l'Animal de Laboratoire" (Animal Care and Use Committee) of sanofi-aventis recherche & développement and were carried out in accordance with French legislation (Decree no 87-848—19 Oct. 1987—and decision—19 Apr. 1988) implementing European directive 86/609/EEC.

A. Formalin-Induced Acute Inflammatory Pain

The formalin test was used to measure nociceptive and inflammatory pain. Indeed, intraplantar injection of formalin induces an initial acute nociceptive behavioral response (0-12 minutes), followed by a second inflammatory-mediated response (15-45 minutes), which is attributed to spinal cord excitability.

Formaldehyde (37%, Sigma) was diluted in saline (v/v) to obtain a 2.5% formaldehyde concentration (i.e. ≅6.25% formalin concentration). Mice were gently restrained and 20 µL of this solution was injected subcutaneously into the dorsal part of one hind paw. Behavioral responses were scored immediately after formalin injection, then at 3 minutes intervals over 45 minutes as follows: (0): normal weight bearing of the injected paw; (1): injected paw resting lightly on floor; (2): lifting-elevation of the injected paw; (3): licking or biting the injected paw. Group sizes were 11-12 male OF1 mice.

Scores were plotted versus time and areas under the curves (AUC) were calculated from the mean scores (±SEM) for both the early (0-12 min) and the late (15-45 min) phases. Reversal of pain-like behaviors was expressed as change in AUC in %.

Figure 9:
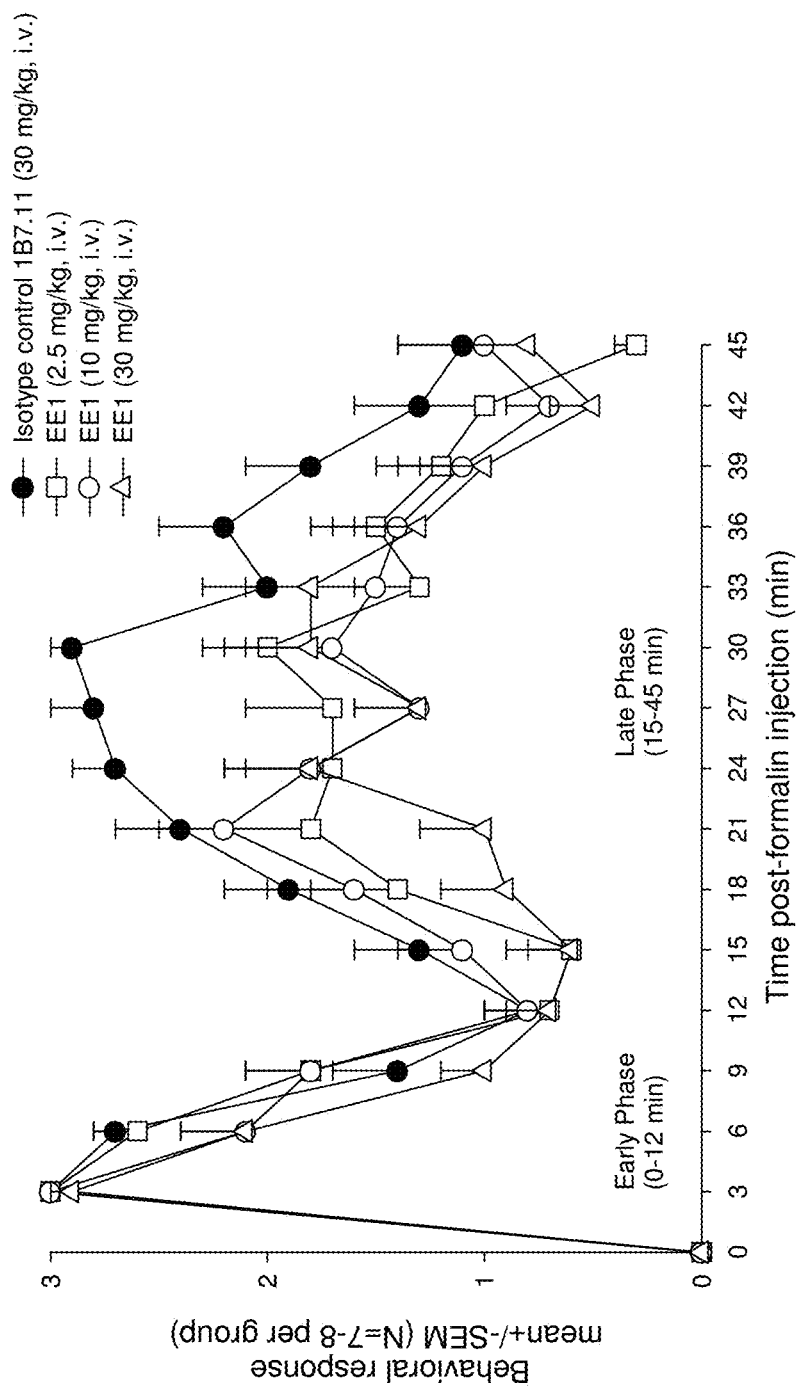
FIG. 9 depicts the results of in vivo experiments determining the effect of EE1 antibody on formalin-induced acute inflammatory pain.

EE1 antibody inhibited the pain-like behavior in the late phase of the formalin test in male OF1 mice. EE1 antibody, when administered intravenously 48 hours before intraplantar injection of formalin, showed a dose dependent reversal of the pain-like behavior only in the late phase with a Minimal Effective Dose (MED)=2.5 mg/kg, as depicted in FIG. 9. Indeed, when administered at 2.5, 10 and 30 mg/kg, EE1 reversed the late phase by 35±5%, 33±5% and 45±7%, respectively, as depicted in Table 29.

In contrast, F151 weakly inhibits the pain-like behavior in the late phase of the formalin test when administered 48 hours before intraplantar injection of formalin. Indeed, when administered at 2.5 and 10 mg/kg, F151 reversed the late phase by 15±7% and 21±5%, respectively, as depicted in Table 29.

TABLE 29

Effect of EE1 and F151 antibodies on formalin-induced pain-like behavior in male OF1 mice

| Group | Dose (mg/kg, i.v.) | A.U.C. ± SEM (15-45 min) | Reversal of pain-like behavior (in %) ± SEM (15-45 min) |
|---|---|---|---|
| Isotype-control 1B7.11 (EE1) | 30 | 63.6 ± 2.9 | 0 ± 5 |
| EE1 | 2.5 | 41.6 ± 3.4 (***) | 35 ± 5 |
|  | 10 | 42.9 ± 2.9 (***) | 33 ± 5 |
|  | 30 | 36.5 ± 4.3 (***) | 45 ± 7 |
| Isotype-control 1B7.11 (F151) | 10 | 57.3 ± 3 | 0 ± 5 |
| F151 | 2.5 | 48.9 ± 3.8 (NS) | 15 ± 7 |
|  | 10 | 45.0 ± 2.8 (*) | 21 ± 5 |

(*) p < 0.05;
(***) p < 0.001: Student's t-test versus adequate control was used.
NS: non significant B. CFA (Complete Freund's Adjuvant)-Induced Chronic Inflammatory Pain Chronic inflammation was induced under brief anesthesia (Isoflurane, 3%) by an intraplantar administration of 25 µL of Complete Freund's Adjuvant (CFA) containing 1 µg/µL heat-killed *Mycobacterium tuberculosis* in mineral oil and mannide monooleate (Sigma). Group sizes were 8 male C57Bl/6 mice.

EE1 antibody was administered intravenously 22 hours after intraplantar CFA injection at 2.5 and 30 mg/kg and mechanical and thermal hypersensitivities were assessed at Day 1 (D1), Day 4 (D4) and Day 7 (D7) post-CFA intraplantar administration.

B1. Mechanical Hypersensitivity

Mechanical hypersensitivity was assessed by measuring the Frequency of withdrawal Response (FR, in %) following 10 applications of a 0.6 g Von Frey filament (Bioseb, France) onto the plantar surface of the injected paw.

To investigate the efficacy of EE1 antibody on pain-like behavior, we calculated the reversal of mechanical hypersensitivity (in %) as follows:

Percent reversals were calculated as (Mean FR-isotype-control$_{postdose}$–FR-Ipsi$_{postdose}$)/(Mean FR-isotype-control$_{postdose}$–Mean FR-sham$_{postdose}$) for each mouse.

Figure 10:
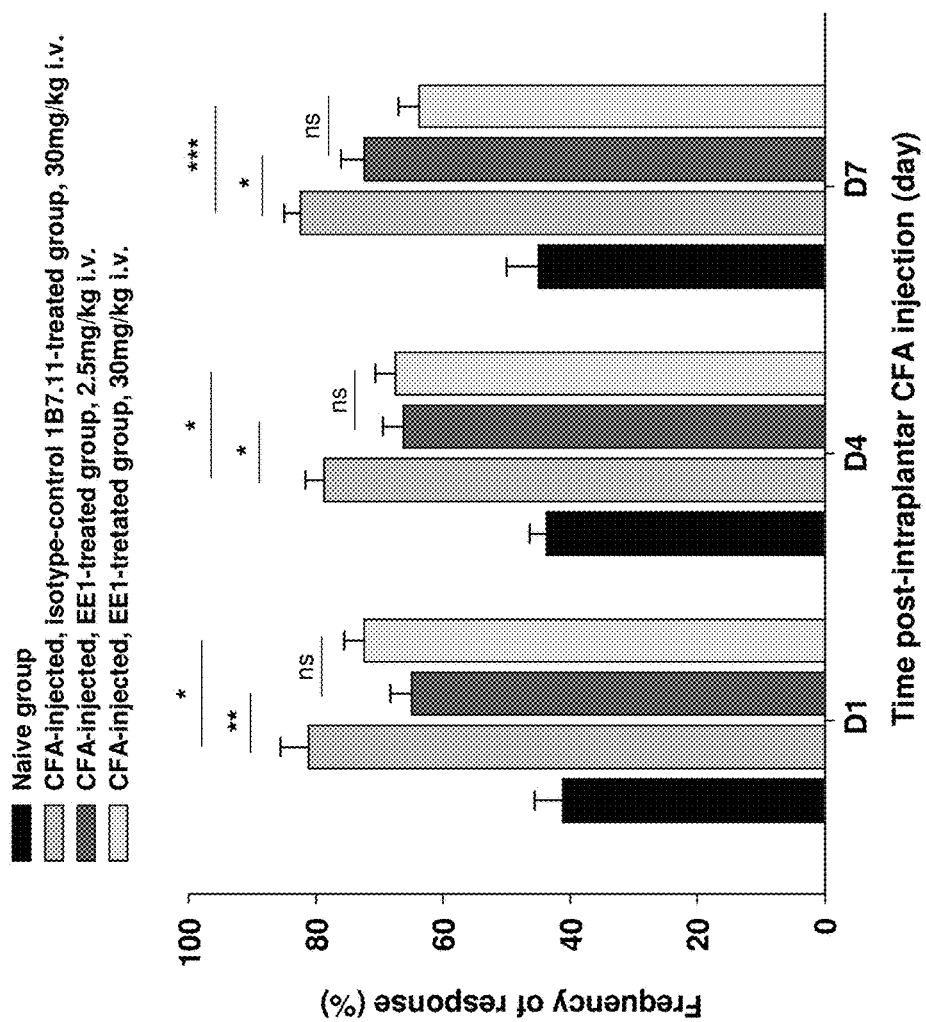
FIG. 10 depicts the results of in vivo experiments determining the effect of EE1 antibody on CFA-induced mechanical hypersensitivity.

At D1, D4 and D7 after intraplantar injection of CFA, a significant increase of FR to the Von Frey filaments was observed in the isotype-control 1B7.11-treated group in comparison with the naive group, demonstrating the development of mechanical hypersensitivity. EE1 antibody, when administered intravenously 22 hours after intraplantar CFA, was able to significantly decrease this FR at the different times studied compared with that obtained in the isotype-control 1B7.11-treated group. (FIG. 10).

Reversal of mechanical hypersensitivity was 41±8% and 22±8% at D1, 36±9% and 32±9% at D4 and 27±10% and 50±9% at D7 for a 2.5 mg/kg and 30 mg/kg intravenous administration of EE1 antibody, respectively (Table 30).

TABLE 30

Effect of EE1 antibody on CFA-induced mechanical hypersensitivity in male C57Bl/6 mice

| Group | Dose (mg/kg, i.v.) | Day 1 post-CFA FR (%) | % effect | Day 4 post-CFA FR (%) | % effect | Day 7 post-CFA FR (%) | % effect |
|---|---|---|---|---|---|---|---|
| Naive | n.a. | 41.3 ± 4.4 | 100 ± 11 | 43.8 ± 2.6 | 100 ± 8 | 45 ± 5 | 100 ± 13 |
| Isotype-control 1B7.11 | 30 | 81.3 ± 4.4 | 0 ± 11 | 78.8 ± 3 | 0 ± 8 | 82.5 ± 2.5 | 0 ± 7 |
| EE1 | 2.5 | 65 ± 3.3 (**) | 41 ± 8 | 66.3 ± 3.2 (*) | 36 ± 9 | 72.5 ± 3.7 (*) | 27 ± 10 |
|  | 30 | 72.5 ± 3.1 (*) | 22 ± 8 | 67.5 ± 3.1 (*) | 32 ± 9 | 63.8 ± 3.2 (***) | 50 ± 9 |

FR: Frequency of Response (in %) ± SEM, % effect ± SEM,
n.a. not applicable
(*), $p < 0.05$, (), $p < 0.01$ and (*), $p < 0.001$, Two-Way ANOVA with time as repeated measure followed by Dunnett's test for factor group for each level of factor time B2. Thermal Hypersensitivity For thermal hypersensitivity, measures of Paw Withdrawal Latencies (PWL, in seconds) in response to a radiant heat using a plantar apparatus (IITC, Woodland Hills, USA) were assessed.

To investigate the efficacy of EE1 antibody on pain-like behavior, we calculated the reversal of thermal hypersensitivity (in %) as follows:

Percent reversals were calculated as ($PWL_{postdose}$−Mean isotype-control$_{postdose}$)/(Mean isotype-control$_{predose}$−Mean isotype-control$_{postdose}$) for each mouse.

Thermal hypersensitivities were not different between all groups at baseline, before intraplantar injection of CFA (data not shown).

At D1, D4 and D7 after intraplantar injection of CFA, a significant decrease in paw withdrawal latency of the injected paw was observed in isotype-control 1B7.11-treated group of mice, demonstrating that CFA induced a thermal hypersensitivity (data not shown).

Figure 11:
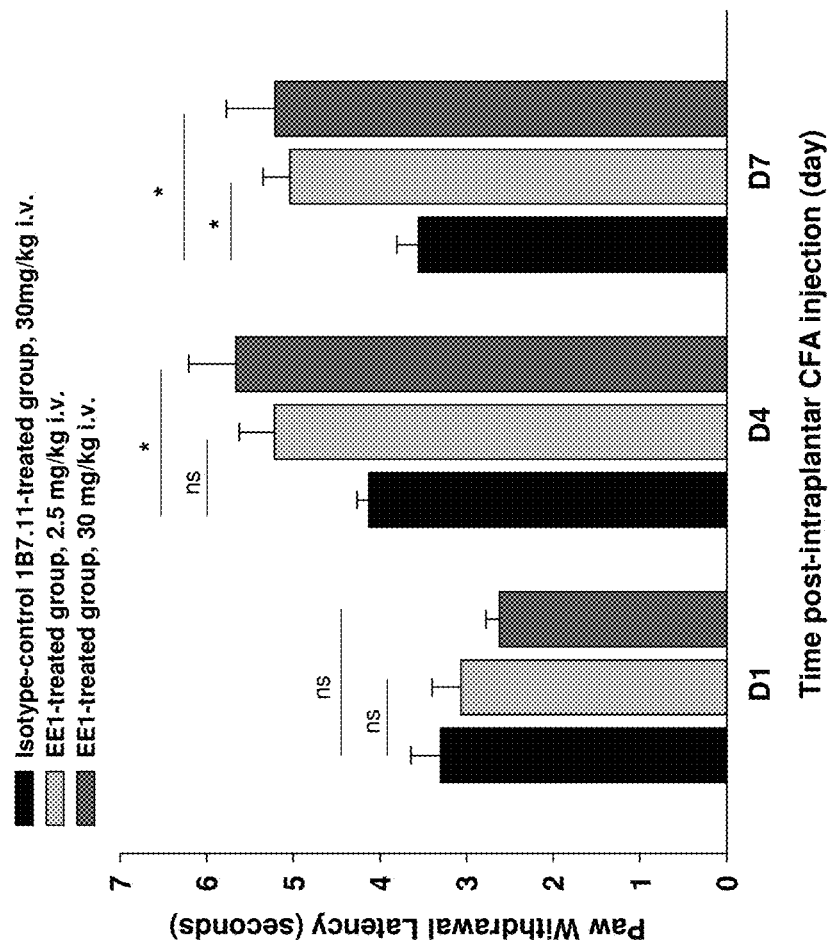
FIG. 11 depicts the results of in vivo experiments determining the effect of EE1 antibody on CFA-induced thermal hypersensitivity.

EE1 antibody, administered intravenously 22 hours after intraplantar CFA injection (i.e. on Day 1 post-intraplantar CFA injection), and was not able to increase the Paw Withdrawal Latency at D1, whatever the dose tested (FIG. 11). However, EE1 significantly increased the Paw Withdrawal Latency at D4 and this effect was also present at D7 (FIG. 11).

Reversal of thermal hypersensitivity was 41±15% and 58±21% at D4 and 46±10% and 52±17% at D7 for a 2.5 mg/kg and 30 mg/kg intravenous administration of EE1, respectively (Table 31).

C. CCI (Chronic Constriction Injury)-Induced Neuropathic-Like Pain (Bennett's Model)

CCI model was used as a model of peripheral nerve injury. Briefly, mice were anesthetized with Isoflurane (3%), and the right sciatic nerve was exposed at mid thigh level through a small incision. Three loose ligatures of 6.0 chromic gut (Ethicon) at 1 mm space were placed around the sciatic nerve. The surgical procedure was completed by closing the muscles and skin. The day of CCI surgery was considered as Day 0. Group sizes were 6-10 male C57Bl/6 mice.

EE1 antibody was administered intravenously at 2.5 and 30 mg/kg on Day 11 post surgery and mechanical and thermal hypersensitivities were assessed on Day 12 (D12), Day 14 (D14) and Day 18 (D18) post-surgery which corresponded to Day 1 (D1), Day 3 (D3) and Day 7 (D7) post-treatment.

C1. Mechanical Hypersensitivity

Mechanical hypersensitivity was assessed by measuring hind paw withdrawal thresholds (on both injured [i.e. Ipsi] and non-injured [i.e. Contra] paws) to an increasing pressure (in g) stimulus using a Dynamic Plantar Aesthesiometer (Ugo-Basile, Italy); a steel rod was applied to the hind paws of the mice with an increasing force (5 grams in 10 seconds).

To investigate the efficacy of EE1 antibody on pain-like behavior, we determined the reversal of mechanical hypersensitivity as follows: percent reversals were calculated as ($Ipsi_{postdose}$−$Ipsi_{predose}$)/($Contra_{predose}$−$Ipsi_{predose}$) for each mouse.

Following surgery, operated mice developed a robust sensitization to mechanical stimulus on the injured paw,

TABLE 31

Effect of EE1 antibody on CFA-induced thermal hypersensitivity in male C57Bl/6 mice

| Group | Dose (mg/kg, i.v.) | Day 1 post-CFA PWL (sec) | % effect | Day 4 post-CFA PWL (sec) | % effect | Day 7 post-CFA PWL (sec) | % effect |
|---|---|---|---|---|---|---|---|
| Isotype-control 1B7.11 | 30 | 3.3 ± 0.3 | n.a. | 4.1 ± 0.1 | n.a. | 3.6 ± 0.3 | n.a. |
| EE1 | 2.5 | 3.1 ± 0.3 | −7 ± 10 | 5.2 ± 0.4 | 41 ± 15 | 5.0 ± 0.3 (*) | 46 ± 10 |
|  | 30 | 2.6 ± 0.2 | −20 ± 5 | 5.7 ± 0.6 (*) | 58 ± 21 | 5.2 ± 0.6 (*) | 52 ± 17 |

PWL: Paw withdrawal latency ± SEM, % effect ± SEM,
n.a. not applicable
(*), $p < 0.05$, Two-Way ANOVA with time as repeated measure followed by Dunnett's test for factor group for each level of factor time whereas the non-injured paw was not affected. At Day 11, the mechanical sensitization on the injured paw reached a plateau (data not shown).

Figure 12:
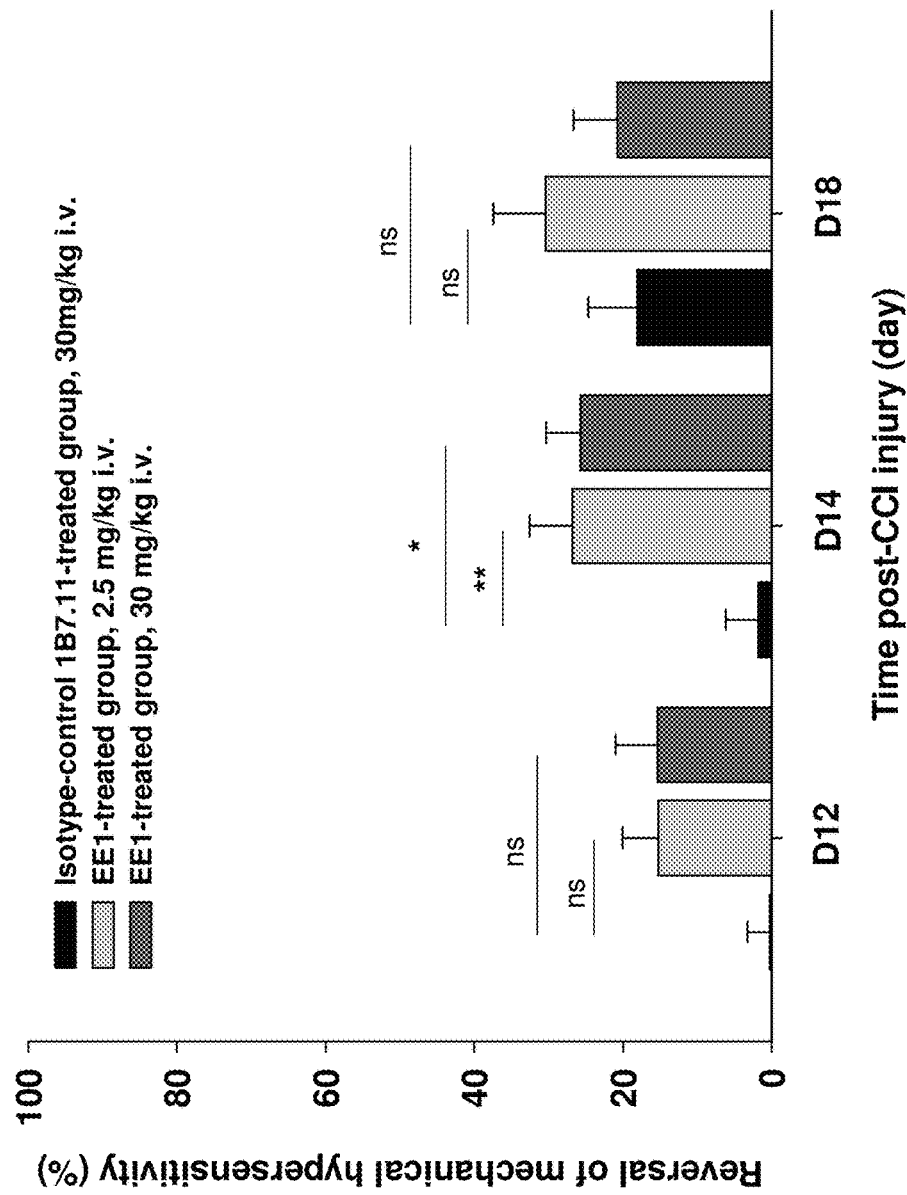
FIG. 12 depicts the results of in vivo experiments determining the effect of EE1 antibody on CCI-induced mechanical hypersensitivity.

EE1 antibody, administered intravenously on Day 11 demonstrated a slight tendency to reverse CCI-induced mechanical hypersensitivity on D12, D14 and D18 with 15.2±4.9% and 15.2±5.7% on D12, 26.8±5.7% and 25.7±4.5% on D14 and 30.3±7.1% and 20.8±5.9% on D18, at 2.5 and 30 mg/kg respectively (FIG. 12 and Table 32).

TABLE 32

Effect of EE1 antibody on CCI-induced mechanical hypersensitivity in male C57Bl/6 mice

| Group | Dose (mg/kg, i.v.) | Day 12 post-CCI % effect ± SEM | Day 14 post-CCI % effect ± SEM | Day 18 post-CCI % effect ± SEM |
|---|---|---|---|---|
| Isotype-control 1B7.11 | 30 | 0.2 ± 3.0 | 1.8 ± 4.3 | 18.1 ± 6.6 |
| EE1 | 2.5 | 15.2 ± 4.9 | 26.8 ± 5.7 (**) | 30.3 ± 7.1 |
|  | 30 | 15.2 ± 5.7 | 25.7 ± 4.5 (*) | 20.8 ± 5.9 |

(*) $p < 0.05$, and
(**) $p < 0.01$ Two-Way ANOVA with time as repeated measure followed by Dunnett's test for factor group for each level of factor time (statistics performed on Delta ipsi values)

C2. Thermal Hypersensitivity

For thermal hypersensitivity, measures of Paw Withdrawal Latencies (in seconds) in response to a radiant heat using a plantar apparatus (IITC, Woodland Hills, USA) were assessed on the injected hind paw.

To investigate the efficacy of EE1 antibody on pain-like behavior, we calculated the reversal of thermal hypersensitivity (in %) as follows:

Percent reversals were calculated as $(Ipsi_{postdose}-\text{Mean isotype-control}_{postdose})/(\text{Mean naive}_{postdose}-\text{Mean isotype-control}_{postdose})$ for each mouse.

Following surgery, operated mice developed a robust sensitization to thermal stimulus on the injured paw, whereas the non-injured paw was not affected. At Day 11, the thermal sensitization on the injured paw reached a plateau (data not shown).

Figure 13:
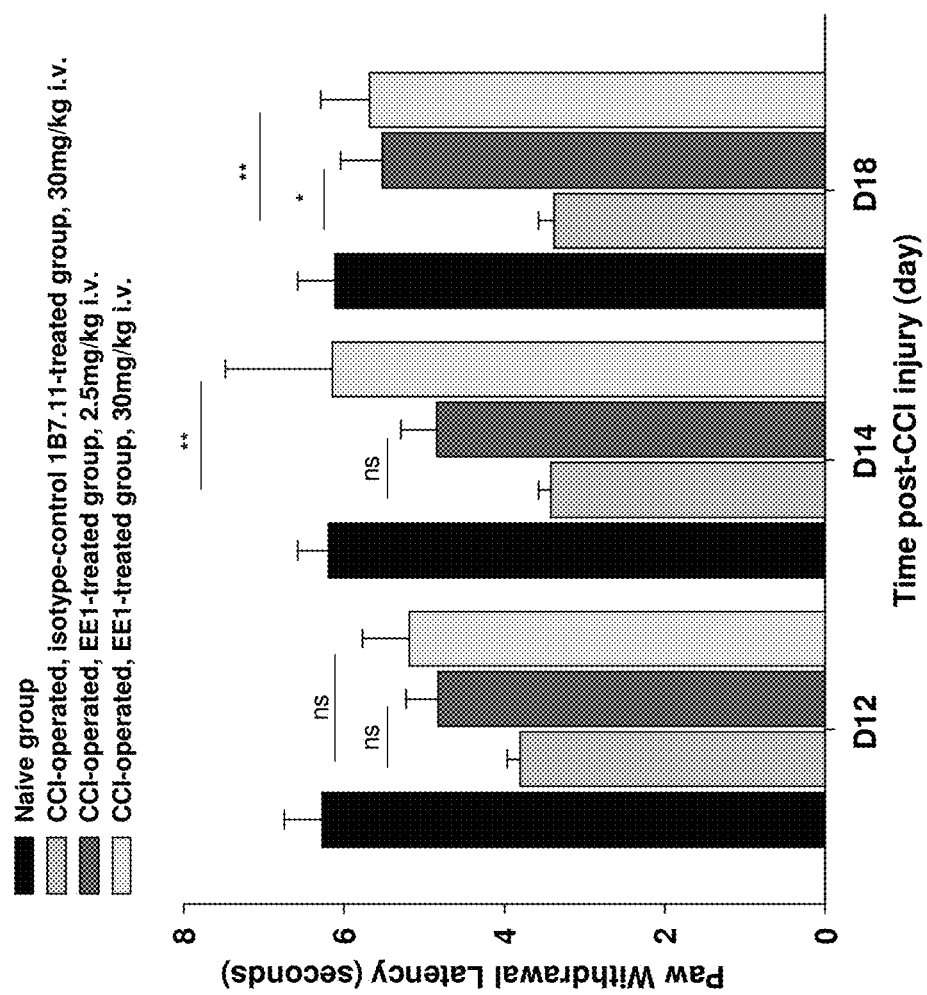
FIG. 13 depicts the results of in vivo experiments determining the effect of EE1 antibody on CCI-induced thermal hypersensitivity.
Figure 14:
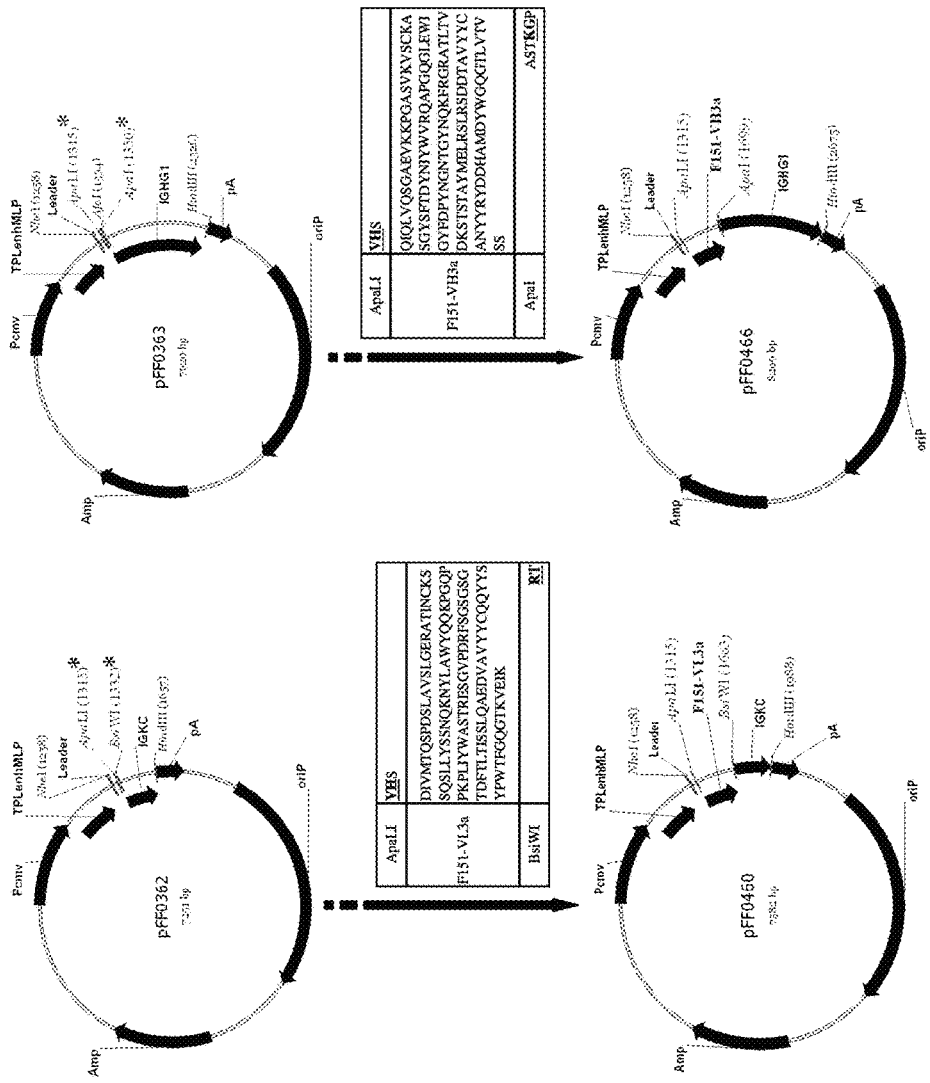
FIG. 14 depicts schematic maps of VL and VH expression constructs for generating humanized F151 variant HC3a/LC3a with the restriction DNA endonuclease sites presented as deduced sequences in bold and underlined. Panel A depicts the light chain and Panel B depicts the heavy chain. Figure discloses SEQ ID NOS 30, 24, and 136, respectively, in order of appearance.

EE1 antibody, administered intravenously on Day 11 did not significantly increase Paw Withdrawal Latency of the injured paw on D12, even if a trend was observed. However, from D14, EE1 antibody significantly increased the Paw Withdrawal (FIG. 13).

Reversal of thermal hypersensitivity was 41±16% and 56±24% at D12 and 51±16% and 98±48% at D14 and 78±19% and 84±22% at D18, for a 2.5 mg/kg and 30 mg/kg intravenous administration of EE1 antibody, respectively (Table 33).

TABLE 33

Effect of EE1 antibody on CCI-induced thermal hypersensitivity in male C57Bl/6 mice
Kinetic evaluation

| Group | Dose (mg/kg, i.v.) | Day 12 post-CCI PWL (sec) | % effect | Day 14 post-CCI PWL (sec) | % effect | Day 18 post-CCI PWL (sec) | % effect |
|---|---|---|---|---|---|---|---|
| naive | n.a. | 6.3 ± 0.5 | 100 ± 19 | 6.2 ± 0.4 | 100 ± 14 | 6.1 ± 0.5 | 100 ± 17 |
| Isotype-control 1B7.11 | 30 | 3.8 ± 0.2 | 0 ± 7 | 3.4 ± 0.2 | 0 ± 5 | 3.4 ± 0.2 | 0 ± 7 |
| EE1 | 2.5 | 4.8 ± 0.4 | 41 ± 16 | 4.8 ± 0.5 | 51 ± 16 | 5.5 ± 0.5 (*) | 78 ± 19 |
|  | 30 | 5.2 ± 0.6 | 56 ± 24 | 6.1 ± 1.3 () | 98 ± 48 | 5.7 ± 0.6 () | 84 ± 22 |

PWL: Paw withdrawal latency ± SEM, % effect ± SEM,
n.a. non applicable
(*), $p < 0.05$, and (**), $p < 0.01$ Two-Way ANOVA with time as repeated measure followed by Dunnett's test for factor group for each level of factor time

SEQUENCE LISTING

<160> NUMBER OF SEQ ID NOS: 137

<210> SEQ ID NO 1
<211> LENGTH: 10
<212> TYPE: PRT
<213> ORGANISM: Homo sapiens

<400> SEQUENCE: 1

Lys Arg Pro Pro Gly Phe Ser Pro Phe Arg
1               5                   10

<210> SEQ ID NO 2
<211> LENGTH: 9
<212> TYPE: PRT
<213> ORGANISM: Homo sapiens

<400> SEQUENCE: 2

Lys Arg Pro Pro Gly Phe Ser Pro Phe
1               5

<210> SEQ ID NO 3
<211> LENGTH: 10
<212> TYPE: PRT
<213> ORGANISM: Mus musculus

<400> SEQUENCE: 3

Arg Arg Pro Pro Gly Phe Ser Pro Phe Arg
1               5                   10

<210> SEQ ID NO 4
<211> LENGTH: 9
<212> TYPE: PRT
<213> ORGANISM: Mus musculus

<400> SEQUENCE: 4

Arg Arg Pro Pro Gly Phe Ser Pro Phe
1               5

<210> SEQ ID NO 5
<211> LENGTH: 9
<212> TYPE: PRT
<213> ORGANISM: Unknown
<220> FEATURE:
<221> NAME/KEY: source
<223> OTHER INFORMATION: /note="Description of Unknown: Bradykinin
      peptide"

<400> SEQUENCE: 5

Arg Pro Pro Gly Phe Ser Pro Phe Arg
1               5

<210> SEQ ID NO 6
<211> LENGTH: 8
<212> TYPE: PRT
<213> ORGANISM: Unknown
<220> FEATURE:
<221> NAME/KEY: source
<223> OTHER INFORMATION: /note="Description of Unknown: Des-Arg9-
      Bradykinin peptide"

<400> SEQUENCE: 6

Arg Pro Pro Gly Phe Ser Pro Phe
1               5

<210> SEQ ID NO 7
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus peptide"
<220> FEATURE:
<221> NAME/KEY: VARIANT
<222> LOCATION: (1)..(1)
<223> OTHER INFORMATION: /replace="Phe" or "His"
<220> FEATURE:
<221> NAME/KEY: misc_feature
<222> LOCATION: (1)..(1)
<223> OTHER INFORMATION: /note="Residue given in the sequence has no
      preference with respect to those in the annotations for said
      position"
<220> FEATURE:
<221> NAME/KEY: VARIANT
<222> LOCATION: (3)..(3)
<223> OTHER INFORMATION: /replace="Asp" or "Ala" or "Val" or "Leu" or
      "Ile" or "Met" or "Phe" or "Tyr" or "Trp"
<220> FEATURE:
<221> NAME/KEY: VARIANT
<222> LOCATION: (4)..(4)

```
<223> OTHER INFORMATION: /replace="Phe" or "Trp" or "His"
<220> FEATURE:
<221> NAME/KEY: misc_feature
<222> LOCATION: (3)..(4)
<223> OTHER INFORMATION: /note="Residues given in the sequence have no
      preference with respect to those in the annotations for said
      positions"
<220> FEATURE:
<221> NAME/KEY: VARIANT
<222> LOCATION: (6)..(6)
<223> OTHER INFORMATION: /replace="Glu" or "Tyr"
<220> FEATURE:
<221> NAME/KEY: misc_feature
<222> LOCATION: (6)..(6)
<223> OTHER INFORMATION: /note="Residue given in the sequence has no
      preference with respect to those in the annotations for said
      position"
<220> FEATURE:
<221> NAME/KEY: VARIANT
<222> LOCATION: (10)..(10)
<223> OTHER INFORMATION: /replace="Glu"
<220> FEATURE:
<221> NAME/KEY: misc_feature
<222> LOCATION: (10)..(10)
<223> OTHER INFORMATION: /note="Residue given in the sequence has no
      preference with respect to that in the annotation for said
      position"

<400> SEQUENCE: 7

Tyr Tyr Arg Tyr Asp Asp His Ala Met Asp Tyr
1               5                   10

<210> SEQ ID NO 8
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus peptide"
<220> FEATURE:
<221> NAME/KEY: VARIANT
<222> LOCATION: (3)..(3)
<223> OTHER INFORMATION: /replace="Arg" or "Ala" or "Val" or "Leu" or
      "Ile" or "Met" or "Phe" or "Tyr" or "Trp"
<220> FEATURE:
<221> NAME/KEY: misc_feature
<222> LOCATION: (3)..(3)
<223> OTHER INFORMATION: /note="Residue given in the sequence has no
      preference with respect to those in the annotations for said
      position"
<220> FEATURE:
<221> NAME/KEY: VARIANT
<222> LOCATION: (5)..(5)
<223> OTHER INFORMATION: /replace="Asp" or "Glu" or "Asn" or "Gln"
<220> FEATURE:
<221> NAME/KEY: misc_feature
<222> LOCATION: (5)..(5)
<223> OTHER INFORMATION: /note="Residue given in the sequence has no
      preference with respect to those in the annotations for said
      position"

<400> SEQUENCE: 8

Tyr Phe Asp Pro Tyr Asn Gly Asn Thr Gly Tyr Asn Gln Lys Phe Arg
1               5                   10                  15

Gly

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

```
    Synthetic consensus peptide"
<220> FEATURE:
<221> NAME/KEY: VARIANT
<222> LOCATION: (8)..(8)
<223> OTHER INFORMATION: /replace="Trp" or "Tyr"
<220> FEATURE:
<221> NAME/KEY: misc_feature
<222> LOCATION: (8)..(8)
<223> OTHER INFORMATION: /note="Residue given in the sequence has no
      preference with respect to those in the annotations for said
      position"

<400> SEQUENCE: 9

Gly Tyr Ser Phe Thr Asp Tyr Asn Ile Tyr
1               5                   10

<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus peptide"
<220> FEATURE:
<221> NAME/KEY: VARIANT
<222> LOCATION: (3)..(3)
<223> OTHER INFORMATION: /replace="Phe" or "His"
<220> FEATURE:
<221> NAME/KEY: VARIANT
<222> LOCATION: (4)..(4)
<223> OTHER INFORMATION: /replace="Phe" or "His" or "Trp"
<220> FEATURE:
<221> NAME/KEY: misc_feature
<222> LOCATION: (3)..(4)
<223> OTHER INFORMATION: /note="Residues given in the sequence have no
      preference with respect to those in the annotations for said
      positions"
<220> FEATURE:
<221> NAME/KEY: VARIANT
<222> LOCATION: (6)..(6)
<223> OTHER INFORMATION: /replace="Phe" or "Thr" or "His"
<220> FEATURE:
<221> NAME/KEY: misc_feature
<222> LOCATION: (6)..(6)
<223> OTHER INFORMATION: /note="Residue given in the sequence has no
      preference with respect to those in the annotations for said
      position"
<220> FEATURE:
<221> NAME/KEY: VARIANT
<222> LOCATION: (8)..(8)
<223> OTHER INFORMATION: /replace="Tyr" or "Phe" or "His" or "Leu"
<220> FEATURE:
<221> NAME/KEY: misc_feature
<222> LOCATION: (8)..(8)
<223> OTHER INFORMATION: /note="Residue given in the sequence has no
      preference with respect to those in the annotations for said
      position"

<400> SEQUENCE: 10

Gln Gln Tyr Tyr Ser Tyr Pro Trp Thr
1               5

<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus peptide"
<220> FEATURE:
<221> NAME/KEY: VARIANT
<222> LOCATION: (6)..(6)
<223> OTHER INFORMATION: /replace="Asp" or "Gln" or "Asn"
```

```
<220> FEATURE:
<221> NAME/KEY: misc_feature
<222> LOCATION: (6)..(6)
<223> OTHER INFORMATION: /note="Residue given in the sequence has no
      preference with respect to those in the annotations for said
      position"

<400> SEQUENCE: 11

Trp Ala Ser Thr Arg Glu
1               5

<210> SEQ ID NO 12
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus peptide"
<220> FEATURE:
<221> NAME/KEY: VARIANT
<222> LOCATION: (8)..(8)
<223> OTHER INFORMATION: /replace="His" or "Tyr" or "Phe"
<220> FEATURE:
<221> NAME/KEY: misc_feature
<222> LOCATION: (8)..(8)
<223> OTHER INFORMATION: /note="Residue given in the sequence has no
      preference with respect to those in the annotations for said
      position"
<220> FEATURE:
<221> NAME/KEY: VARIANT
<222> LOCATION: (15)..(15)
<223> OTHER INFORMATION: /replace="Tyr"
<220> FEATURE:
<221> NAME/KEY: misc_feature
<222> LOCATION: (15)..(15)
<223> OTHER INFORMATION: /note="Residue given in the sequence has no
      preference with respect to that in the annotation for said
      position"

<400> SEQUENCE: 12

Lys Ser Ser Gln Ser Leu Leu Trp Ser Ser Asn Gln Lys Asn His Leu
1               5                   10                  15

Ala

<210> SEQ ID NO 13
<211> LENGTH: 11
<212> TYPE: PRT
<213> ORGANISM: Mus musculus

<400> SEQUENCE: 13

Tyr Tyr Arg Tyr Asp Asp His Ala Met Asp Tyr
1               5                   10

<210> SEQ ID NO 14
<211> LENGTH: 17
<212> TYPE: PRT
<213> ORGANISM: Mus musculus

<400> SEQUENCE: 14

Tyr Phe Asp Pro Tyr Asn Gly Asn Thr Gly Tyr Asn Gln Lys Phe Arg
1               5                   10                  15

Gly

<210> SEQ ID NO 15
<211> LENGTH: 10
<212> TYPE: PRT
<213> ORGANISM: Mus musculus
```

-continued

```
<400> SEQUENCE: 15

Gly Tyr Ser Phe Thr Asp Tyr Asn Ile Tyr
1               5                   10

<210> SEQ ID NO 16
<211> LENGTH: 9
<212> TYPE: PRT
<213> ORGANISM: Mus musculus

<400> SEQUENCE: 16

Gln Gln Tyr Tyr Ser Tyr Pro Trp Thr
1               5

<210> SEQ ID NO 17
<211> LENGTH: 7
<212> TYPE: PRT
<213> ORGANISM: Mus musculus

<400> SEQUENCE: 17

Trp Ala Ser Thr Arg Glu Ser
1               5

<210> SEQ ID NO 18
<211> LENGTH: 17
<212> TYPE: PRT
<213> ORGANISM: Mus musculus

<400> SEQUENCE: 18

Lys Ser Ser Gln Ser Leu Leu Tyr Ser Ser Asn Gln Lys Asn Tyr Leu
1               5                   10                  15

Ala

<210> SEQ ID NO 19
<211> LENGTH: 120
<212> TYPE: PRT
<213> ORGANISM: Mus musculus

<400> SEQUENCE: 19

Glu Ile Gln Leu Gln Gln Ser Gly Pro Glu Leu Val Lys Pro Gly Thr
1               5                   10                  15

Ser Val Lys Val Ser Cys Lys Ala Ser Gly Tyr Ser Phe Thr Asp Tyr
                20                  25                  30

Asn Ile Tyr Trp Val Lys Gln Ser His Gly Lys Ser Leu Glu Trp Ile
            35                  40                  45

Gly Tyr Phe Asp Pro Tyr Asn Gly Asn Thr Gly Tyr Asn Gln Lys Phe
        50                  55                  60

Arg Gly Lys Ala Thr Leu Thr Val Asp Lys Ser Ser Ser Thr Ala Phe
65                  70                  75                  80

Met His Leu Ser Ser Leu Thr Ser Asp Ser Ala Val Tyr Tyr Cys
                85                  90                  95

Ala Asn Tyr Tyr Arg Tyr Asp Asp His Ala Met Asp Tyr Trp Gly Gln
                100                 105                 110

Gly Thr Ser Val Thr Val Ser Ser
            115                 120

<210> SEQ ID NO 20
<211> LENGTH: 120
<212> TYPE: PRT
<213> ORGANISM: Artificial Sequence
<220> FEATURE:
<221> NAME/KEY: source
```

<223> OTHER INFORMATION: /note="Description of Artificial Sequence:
     Synthetic polypeptide"

<400> SEQUENCE: 20

Glu Ile Gln Leu Val Gln Ser Gly Pro Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Ile Tyr Trp Val Lys Gln Ser Pro Gly Lys Ser Leu Glu Trp Ile
        35                  40                  45

Gly Tyr Phe Asp Pro Tyr Asn Gly Asn Thr Gly Tyr Asn Gln Lys Phe
    50                  55                  60

Arg Gly Lys Ala Thr Leu Thr Val Asp Lys Ser Ser Ser Thr Ala Phe
65                  70                  75                  80

Met His Leu Ser Ser Leu Thr Ser Glu Asp Ser Ala Val Tyr Tyr Cys
                85                  90                  95

Ala Asn Tyr Tyr Arg Tyr Asp Asp His Ala Met Asp Tyr Trp Gly Gln
            100                 105                 110

Gly Thr Ser Val Thr Val Ser Ser
        115                 120

<210> SEQ ID NO 21
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 21

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Ile Tyr Trp Val Lys Gln Ser Pro Gly Lys Gly Leu Glu Trp Ile
        35                  40                  45

Gly Tyr Phe Asp Pro Tyr Asn Gly Asn Thr Gly Tyr Asn Gln Lys Phe
    50                  55                  60

Arg Gly Lys Ala Thr Leu Thr Val Asp Lys Ser Ser Ser Thr Ala Tyr
65                  70                  75                  80

Met His Leu Ser Ser Leu Thr Ser Glu Glu Ser Ala Val Tyr Tyr Cys
                85                  90                  95

Ala Asn Tyr Tyr Arg Tyr Asp Asp His Ala Met Asp Tyr Trp Gly Gln
            100                 105                 110

Gly Thr Ser Val Thr Val Ser Ser
        115                 120

<210> SEQ ID NO 22
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 22

Gln Ile Gln Leu Val Gln Ser Gly Ala Glu Val Lys Lys Pro Gly Ala
1               5                   10                  15

```
Ser Val Lys Val Ser Cys Lys Ala Ser Gly Tyr Ser Phe Thr Asp Tyr
            20                  25                  30

Asn Ile Tyr Trp Val Lys Gln Ser Pro Gly Lys Gly Leu Glu Trp Ile
            35                  40                  45

Gly Tyr Phe Asp Pro Tyr Asn Gly Asn Thr Gly Tyr Asn Glu Lys Phe
        50                  55                  60

Arg Gly Lys Ala Thr Leu Thr Val Asp Lys Ser Ser Ser Thr Ala Tyr
65                  70                  75                  80

Met His Leu Ser Ser Leu Thr Ser Glu Glu Ser Ala Val Tyr Tyr Cys
                85                  90                  95

Ala Asn Tyr Tyr Arg Tyr Asp Asp His Ala Met Asp Tyr Trp Gly Gln
            100                 105                 110

Gly Thr Ser Val Thr Val Ser Ser
        115                 120

<210> SEQ ID NO 23
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Ile Tyr Trp Val Lys Gln Ser Pro Gly Lys Gly Leu Glu Trp Ile
            35                  40                  45

Gly Tyr Phe Asp Pro Tyr Asn Gly Asn Thr Gly Tyr Asn Gln Lys Phe
        50                  55                  60

Arg Gly Lys Ala Thr Leu Thr Val Asp Lys Ser Ser Ser Thr Ala Tyr
65                  70                  75                  80

Met His Leu Ser Ser Lys Thr Ser Glu Glu Ser Ala Val Tyr Tyr Cys
                85                  90                  95

Ala Asn Tyr Tyr Arg Tyr Asp Asp His Ala Met Asp Tyr Trp Gly Gln
            100                 105                 110

Gly Thr Ser Val Thr Val Ser Ser
        115                 120

<210> SEQ ID NO 24
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Ile Tyr Trp Val Arg Gln Ala Pro Gly Gln Gly Leu Glu Trp Ile
            35                  40                  45
```

Gly Tyr Phe Asp Pro Tyr Asn Gly Asn Thr Gly Tyr Asn Gln Lys Phe
    50                  55                  60

Arg Gly Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Asn Tyr Tyr Arg Tyr Asp Asp His Ala Met Asp Tyr Trp Gly Gln
                100                 105                 110

Gly Thr Leu Val Thr Val Ser Ser
            115                 120

<210> SEQ ID NO 25
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Asn Ile Tyr Trp Val Arg Gln Ala Pro Gly Gln Gly Leu Glu Trp Met
            35                  40                  45

Gly Tyr Phe Asp Pro Tyr Asn Gly Asn Thr Gly Tyr Asn Gln Lys Phe
    50                  55                  60

Arg Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Asn Tyr Tyr Arg Tyr Asp Asp His Ala Met Asp Tyr Trp Gly Gln
                100                 105                 110

Gly Thr Leu Val Thr Val Ser Ser
            115                 120

<210> SEQ ID NO 26
<211> LENGTH: 113
<212> TYPE: PRT
<213> ORGANISM: Mus musculus

<400> SEQUENCE: 26

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Pro Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Ile Tyr Tyr Cys Gln Gln
                85                  90                  95

Tyr Tyr Ser Tyr Pro Trp Thr Phe Gly Gly Gly Thr Lys Leu Glu Ile
                100                 105                 110

-continued

Lys

<210> SEQ ID NO 27
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Asp Ile Val Met Ser Gln Ser Pro Ser Ser Leu Ala Ala Ser Val Gly
1               5                   10                  15

Asp Arg Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Lys
            35                  40                  45

Ser Pro Lys Pro Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Gln
                85                  90                  95

Tyr Tyr Ser Tyr Pro Trp Thr Phe Gly Gly Gly Thr Lys Leu Glu Ile
                100                 105                 110

Lys

<210> SEQ ID NO 28
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Ile Val Met Thr Gln Ser Pro Ser Ser Leu Ser Ala Ser Val Gly
1               5                   10                  15

Asp Arg Val Thr Ile Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Lys
            35                  40                  45

Ser Pro Lys Pro Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Thr Tyr Tyr Cys Gln Gln
                85                  90                  95

Tyr Tyr Ser Tyr Pro Trp Thr Phe Gly Gly Gly Thr Lys Leu Glu Ile
                100                 105                 110

Lys

<210> SEQ ID NO 29
<211> LENGTH: 113
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 29

Asp Ile Val Met Thr Gln Ser Pro Ser Ser Leu Ser Ala Ser Val Gly
1               5                   10                  15

Asp Arg Val Thr Ile Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Lys
        35                  40                  45

Ser Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Lys Ala Thr Tyr Tyr Cys Gln Gln
                85                  90                  95

Tyr Tyr Ser Tyr Pro Trp Thr Phe Gly Gly Gly Thr Lys Leu Glu Ile
            100                 105                 110

Lys

<210> SEQ ID NO 30
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Trp Thr Phe Gly Gln Gly Thr Lys Val Glu Ile
            100                 105                 110

Lys

<210> SEQ ID NO 31
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Trp Thr Phe Gly Gln Gly Thr Lys Val Glu Ile
            100                 105                 110

Lys

<210> SEQ ID NO 32
<211> LENGTH: 11
<212> TYPE: PRT
<213> ORGANISM: Mus musculus

<400> SEQUENCE: 32

Trp Glu Tyr Asp Gly Tyr Tyr Asp Leu Asp Tyr
1               5                   10

<210> SEQ ID NO 33
<211> LENGTH: 17
<212> TYPE: PRT
<213> ORGANISM: Mus musculus

<400> SEQUENCE: 33

Trp Ile Asp Pro Glu Asn Gly Asp Thr Gly Tyr Ala Arg Lys Phe Gln
1               5                   10                  15

Gly

<210> SEQ ID NO 34
<211> LENGTH: 10
<212> TYPE: PRT
<213> ORGANISM: Mus musculus

<400> SEQUENCE: 34

Gly Phe Asn Ile Lys Asp Tyr Tyr Leu His
1               5                   10

<210> SEQ ID NO 35
<211> LENGTH: 9
<212> TYPE: PRT
<213> ORGANISM: Mus musculus

<400> SEQUENCE: 35

Leu Gln Gly Thr His Phe Pro Tyr Thr
1               5

<210> SEQ ID NO 36
<211> LENGTH: 7
<212> TYPE: PRT
<213> ORGANISM: Mus musculus

<400> SEQUENCE: 36

Leu Val Ser Lys Leu Asp Ser
1               5

<210> SEQ ID NO 37

```
<211> LENGTH: 16
<212> TYPE: PRT
<213> ORGANISM: Mus musculus

<400> SEQUENCE: 37

Lys Ser Ser Gln Ser Leu Leu Tyr Ser Asn Gly Lys Thr Tyr Leu Asn
1               5                   10                  15

<210> SEQ ID NO 38
<211> LENGTH: 120
<212> TYPE: PRT
<213> ORGANISM: Mus musculus

<400> SEQUENCE: 38

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
                20                  25                  30

Tyr Leu His Trp Val Lys Gln Arg Pro Glu Gln Gly Leu Glu Trp Ile
            35                  40                  45

Gly Trp Ile Asp Pro Glu Asn Gly Asp Thr Gly Tyr Ala Arg Lys Phe
        50                  55                  60

Gln Gly Lys Ala Thr Met Thr Ala Asp Thr Ser Asn Thr Val Tyr
65                  70                  75                  80

Leu His Leu Ser Ser Leu Thr Ser Glu Asp Thr Ala Val Tyr Tyr Phe
                85                  90                  95

Asn Ala Trp Glu Tyr Asp Gly Tyr Tyr Asp Leu Asp Tyr Trp Gly Gln
                100                 105                 110

Gly Thr Ser Val Thr Val Ser Ser
            115                 120

<210> SEQ ID NO 39
<211> LENGTH: 112
<212> TYPE: PRT
<213> ORGANISM: Mus musculus

<400> SEQUENCE: 39

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
                20                  25                  30

Asn Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ile Arg Val Glu Ala Glu Asp Leu Gly Val Tyr Tyr Cys Leu Gln Gly
                85                  90                  95

Thr His Phe Pro Tyr Thr Phe Gly Gly Gly Thr Lys Leu Glu Ile Lys
                100                 105                 110

<210> SEQ ID NO 40
<211> LENGTH: 7
<212> TYPE: PRT
<213> ORGANISM: Mus musculus

<400> SEQUENCE: 40

Glu Asp Tyr Gly Gly Asp Tyr
```

<210> SEQ ID NO 41
<211> LENGTH: 19
<212> TYPE: PRT
<213> ORGANISM: Mus musculus

<400> SEQUENCE: 41

Glu Ile Arg Ser Lys Ser Asn Asn Tyr Ala Thr His Tyr Ala Glu Ser
1               5                   10                  15

Val Lys Gly

<210> SEQ ID NO 42
<211> LENGTH: 10
<212> TYPE: PRT
<213> ORGANISM: Mus musculus

<400> SEQUENCE: 42

Gly Phe Thr Phe Ser Asn Tyr Trp Met Asn
1               5                   10

<210> SEQ ID NO 43
<211> LENGTH: 9
<212> TYPE: PRT
<213> ORGANISM: Mus musculus

<400> SEQUENCE: 43

Gln Gln Tyr Tyr Ser Tyr Pro Tyr Thr
1               5

<210> SEQ ID NO 44
<211> LENGTH: 17
<212> TYPE: PRT
<213> ORGANISM: Mus musculus

<400> SEQUENCE: 44

Lys Ser Ser Gln Ser Leu Leu Tyr Ser Ser Asp Gln Arg Asn Tyr Leu
1               5                   10                  15

Ala

<210> SEQ ID NO 45
<211> LENGTH: 118
<212> TYPE: PRT
<213> ORGANISM: Mus musculus

<400> SEQUENCE: 45

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Ser Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ile Gly Glu Asp Tyr Gly Gly Asp Tyr Trp Gly Gln Gly Thr
            100                 105                 110

Ser Val Thr Val Ser Ser
        115

<210> SEQ ID NO 46
<211> LENGTH: 113
<212> TYPE: PRT
<213> ORGANISM: Mus musculus

<400> SEQUENCE: 46

Asp Ile Val Met Ser Gln Ser Pro Ser Ser Leu Ala Val Ser Val Gly
1               5                   10                  15

Glu Lys Val Thr Met Ser Cys Lys Ser Gln Ser Leu Leu Tyr Ser
            20                  25                  30

Ser Asp Gln Arg Asn Tyr Leu Ala Trp Tyr Gln Gln Arg Ser Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys

<210> SEQ ID NO 47
<211> LENGTH: 12
<212> TYPE: PRT
<213> ORGANISM: Mus musculus

<400> SEQUENCE: 47

Phe Glu Tyr Asp Gly Asn Tyr Ser Pro Leu Asp Phe
1               5                   10

<210> SEQ ID NO 48
<211> LENGTH: 16
<212> TYPE: PRT
<213> ORGANISM: Mus musculus

<400> SEQUENCE: 48

Trp Val Asp Pro Glu Asn Gly Asp Ser Asp Tyr Ala Pro Lys Phe Gln
1               5                   10                  15

<210> SEQ ID NO 49
<211> LENGTH: 10
<212> TYPE: PRT
<213> ORGANISM: Mus musculus

<400> SEQUENCE: 49

Gly Phe Asn Ile Lys Asp Tyr Tyr Met His
1               5                   10

<210> SEQ ID NO 50
<211> LENGTH: 9
<212> TYPE: PRT
<213> ORGANISM: Mus musculus

<400> SEQUENCE: 50

Gln Asn Asp His Ser Tyr Pro Leu Thr
1               5

```
<210> SEQ ID NO 51
<211> LENGTH: 7
<212> TYPE: PRT
<213> ORGANISM: Mus musculus

<400> SEQUENCE: 51

Gly Ala Ser Thr Arg Glu Ser
1               5

<210> SEQ ID NO 52
<211> LENGTH: 17
<212> TYPE: PRT
<213> ORGANISM: Mus musculus

<400> SEQUENCE: 52

Lys Ser Ser Gln Ser Leu Leu Asn Ser Gly Asn Gln Lys Asn Tyr Leu
1               5                   10                  15

Ala

<210> SEQ ID NO 53
<211> LENGTH: 121
<212> TYPE: PRT
<213> ORGANISM: Mus musculus

<400> SEQUENCE: 53

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Val Asp Pro Glu Asn Gly Asp Ser Asp Tyr Ala Pro Lys Phe
    50                  55                  60

Gln Gly Lys Ala Thr Met Thr Ala Asp Thr Ser Ser Asn Thr Val Tyr
65                  70                  75                  80

Leu Gln Phe Ser Ser Leu Thr Ser Glu Asp Thr Ala Val Tyr Tyr Cys
                85                  90                  95

Asn Ala Phe Glu Tyr Asp Gly Asn Tyr Ser Pro Leu Asp Phe Trp Gly
            100                 105                 110

Gln Gly Thr Ser Val Thr Val Ser Ser
        115                 120

<210> SEQ ID NO 54
<211> LENGTH: 113
<212> TYPE: PRT
<213> ORGANISM: Mus musculus

<400> SEQUENCE: 54

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
```

```
                    85                  90                  95
Asp His Ser Tyr Pro Leu Thr Phe Gly Ala Gly Thr Lys Leu Glu Leu
                100                 105                 110
Lys

<210> SEQ ID NO 55
<211> LENGTH: 12
<212> TYPE: PRT
<213> ORGANISM: Mus musculus

<400> SEQUENCE: 55

Phe Glu Tyr Asp Gly Asn Tyr Ser Pro Leu Asp Phe
1               5                   10

<210> SEQ ID NO 56
<211> LENGTH: 17
<212> TYPE: PRT
<213> ORGANISM: Mus musculus

<400> SEQUENCE: 56

Trp Val Asp Pro Glu Asn Gly Asp Ser Asp Tyr Ala Pro Lys Phe Gln
1               5                   10                  15
Gly

<210> SEQ ID NO 57
<211> LENGTH: 10
<212> TYPE: PRT
<213> ORGANISM: Mus musculus

<400> SEQUENCE: 57

Gly Phe Asn Ile Lys Asp Tyr Tyr Met His
1               5                   10

<210> SEQ ID NO 58
<211> LENGTH: 9
<212> TYPE: PRT
<213> ORGANISM: Mus musculus

<400> SEQUENCE: 58

Met Gln Gly Thr His Phe Pro Tyr Thr
1               5

<210> SEQ ID NO 59
<211> LENGTH: 7
<212> TYPE: PRT
<213> ORGANISM: Mus musculus

<400> SEQUENCE: 59

Leu Val Ser Lys Leu Asp Ser
1               5

<210> SEQ ID NO 60
<211> LENGTH: 16
<212> TYPE: PRT
<213> ORGANISM: Mus musculus

<400> SEQUENCE: 60

Lys Ser Ser Gln Ser Leu Leu Tyr Ser Asn Gly Glu Thr Tyr Leu Asn
1               5                   10                  15

<210> SEQ ID NO 61
<211> LENGTH: 121
<212> TYPE: PRT
```

<213> ORGANISM: Mus musculus

<400> SEQUENCE: 61

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Val Asp Pro Glu Asn Gly Asp Ser Asp Tyr Ala Pro Lys Phe
    50                  55                  60

Gln Gly Lys Ala Thr Met Thr Ala Asp Thr Ser Ser Asn Thr Val Tyr
65                  70                  75                  80

Leu Gln Phe Ser Ser Leu Thr Ser Glu Asp Thr Ala Val Tyr Tyr Cys
                85                  90                  95

Asn Ala Phe Glu Tyr Asp Gly Asn Tyr Ser Pro Leu Asp Phe Trp Gly
            100                 105                 110

Gln Gly Thr Ser Val Thr Val Ser Ser
        115                 120

<210> SEQ ID NO 62
<211> LENGTH: 112
<212> TYPE: PRT
<213> ORGANISM: Mus musculus

<400> SEQUENCE: 62

Asp Val Val Met Thr Gln Thr Pro Leu Thr Leu Ser Val Pro Ile Gly
1               5                   10                  15

Gln Pro Ala Ser Ile Ser Cys Lys Ser Ser Gln Ser Leu Leu Tyr Ser
            20                  25                  30

Asn Gly Glu Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Arg Ser Gly Thr Asp Phe Thr Leu Lys Ile
65                  70                  75                  80

Ser Arg Val Glu Ser Glu Asp Leu Gly Val Tyr Tyr Cys Met Gln Gly
                85                  90                  95

Thr His Phe Pro Tyr Thr Phe Gly Gly Gly Thr Lys Leu Glu Ile Lys
            100                 105                 110

<210> SEQ ID NO 63
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic consensus peptide"
<220> FEATURE:
<221> NAME/KEY: VARIANT
<222> LOCATION: (1)..(1)
<223> OTHER INFORMATION: /replace="Phe"
<220> FEATURE:
<221> NAME/KEY: misc_feature
<222> LOCATION: (1)..(1)
<223> OTHER INFORMATION: /note="Residue given in the sequence has no preference with respect to that in the annotation for said position"
<220> FEATURE:
<221> NAME/KEY: VARIANT
<222> LOCATION: (6)..(6)

```
<223> OTHER INFORMATION: /replace=" "
<220> FEATURE:
<221> NAME/KEY: misc_feature
<222> LOCATION: (6)..(6)
<223> OTHER INFORMATION: /note="Residue given in the sequence has no
      preference with respect to that in the annotation for said
      position"
<220> FEATURE:
<221> NAME/KEY: VARIANT
<222> LOCATION: (8)..(8)
<223> OTHER INFORMATION: /replace="Ser"
<220> FEATURE:
<221> NAME/KEY: VARIANT
<222> LOCATION: (9)..(9)
<223> OTHER INFORMATION: /replace="Pro"
<220> FEATURE:
<221> NAME/KEY: misc_feature
<222> LOCATION: (8)..(9)
<223> OTHER INFORMATION: /note="Residues given in the sequence have no
      preference with respect to those in the annotations for said
      positions"
<220> FEATURE:
<221> NAME/KEY: VARIANT
<222> LOCATION: (12)..(12)
<223> OTHER INFORMATION: /replace="Tyr"
<220> FEATURE:
<221> NAME/KEY: misc_feature
<222> LOCATION: (12)..(12)
<223> OTHER INFORMATION: /note="Residue given in the sequence has no
      preference with respect to that in the annotation for said
      position"

<400> SEQUENCE: 63

Trp Glu Tyr Asp Gly Asn Tyr Tyr Asp Leu Asp Phe
1               5                   10

<210> SEQ ID NO 64
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus peptide"
<220> FEATURE:
<221> NAME/KEY: VARIANT
<222> LOCATION: (2)..(2)
<223> OTHER INFORMATION: /replace="Val"
<220> FEATURE:
<221> NAME/KEY: misc_feature
<222> LOCATION: (2)..(2)
<223> OTHER INFORMATION: /note="Residue given in the sequence has no
      preference with respect to that in the annotation for said
      position"
<220> FEATURE:
<221> NAME/KEY: VARIANT
<222> LOCATION: (9)..(9)
<223> OTHER INFORMATION: /replace="Ser"
<220> FEATURE:
<221> NAME/KEY: misc_feature
<222> LOCATION: (9)..(9)
<223> OTHER INFORMATION: /note="Residue given in the sequence has no
      preference with respect to that in the annotation for said
      position"
<220> FEATURE:
<221> NAME/KEY: VARIANT
<222> LOCATION: (10)..(10)
<223> OTHER INFORMATION: /replace="Asp"
<220> FEATURE:
<221> NAME/KEY: misc_feature
<222> LOCATION: (10)..(10)
<223> OTHER INFORMATION: /note="Residue given in the sequence has no
      preference with respect to that in the annotation for said
      position"

<400> SEQUENCE: 64
```

```
Trp Ile Asp Pro Glu Asn Gly Asp Thr Gly Tyr Ala Pro Lys Phe Gln
1               5                   10                  15
Gly

<210> SEQ ID NO 65
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus peptide"
<220> FEATURE:
<221> NAME/KEY: VARIANT
<222> LOCATION: (9)..(9)
<223> OTHER INFORMATION: /replace="Met"
<220> FEATURE:
<221> NAME/KEY: misc_feature
<222> LOCATION: (9)..(9)
<223> OTHER INFORMATION: /note="Residue given in the sequence has no
      preference with respect to that in the annotation for said
      position"

<400> SEQUENCE: 65

Gly Phe Asn Ile Lys Asp Tyr Tyr Leu His
1               5                   10

<210> SEQ ID NO 66
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus peptide"
<220> FEATURE:
<221> NAME/KEY: VARIANT
<222> LOCATION: (2)..(2)
<223> OTHER INFORMATION: /replace="Asn"
<220> FEATURE:
<221> NAME/KEY: VARIANT
<222> LOCATION: (3)..(3)
<223> OTHER INFORMATION: /replace="Phe" or "Asp" or "His"
<220> FEATURE:
<221> NAME/KEY: misc_feature
<222> LOCATION: (2)..(3)
<223> OTHER INFORMATION: /note="Residues given in the sequence have no
      preference with respect to those in the annotations for said
      positions"
<220> FEATURE:
<221> NAME/KEY: VARIANT
<222> LOCATION: (4)..(4)
<223> OTHER INFORMATION: /replace="Phe" or "His" or "Trp"
<220> FEATURE:
<221> NAME/KEY: misc_feature
<222> LOCATION: (4)..(4)
<223> OTHER INFORMATION: /note="Residue given in the sequence has no
      preference with respect to those in the annotations for said
      position"
<220> FEATURE:
<221> NAME/KEY: VARIANT
<222> LOCATION: (6)..(6)
<223> OTHER INFORMATION: /replace="Phe" or "Thr" or "His"
<220> FEATURE:
<221> NAME/KEY: misc_feature
<222> LOCATION: (6)..(6)
<223> OTHER INFORMATION: /note="Residue given in the sequence has no
      preference with respect to those in the annotations for said
      position"
<220> FEATURE:
<221> NAME/KEY: VARIANT
<222> LOCATION: (8)..(8)
<223> OTHER INFORMATION: /replace="Tyr" or "Phe" or "His" or "Leu"
<220> FEATURE:
<221> NAME/KEY: misc_feature
```

```
<222> LOCATION: (8)..(8)
<223> OTHER INFORMATION: /note="Residue given in the sequence has no
      preference with respect to those in the annotations for said
      position"

<400> SEQUENCE: 66

Gln Gln Tyr Tyr Ser Tyr Pro Trp Thr
1               5

<210> SEQ ID NO 67
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus peptide"
<220> FEATURE:
<221> NAME/KEY: VARIANT
<222> LOCATION: (1)..(1)
<223> OTHER INFORMATION: /replace="Gly"
<220> FEATURE:
<221> NAME/KEY: misc_feature
<222> LOCATION: (1)..(1)
<223> OTHER INFORMATION: /note="Residue given in the sequence has no
      preference with respect to that in the annotation for said
      position"
<220> FEATURE:
<221> NAME/KEY: VARIANT
<222> LOCATION: (6)..(6)
<223> OTHER INFORMATION: /replace="Asp" or "Gln" or "Asn"
<220> FEATURE:
<221> NAME/KEY: misc_feature
<222> LOCATION: (6)..(6)
<223> OTHER INFORMATION: /note="Residue given in the sequence has no
      preference with respect to those in the annotations for said
      position"

<400> SEQUENCE: 67

Trp Ala Ser Thr Arg Glu
1               5

<210> SEQ ID NO 68
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus peptide"
<220> FEATURE:
<221> NAME/KEY: VARIANT
<222> LOCATION: (8)..(8)
<223> OTHER INFORMATION: /replace="His" or "Tyr" or "Phe"
<220> FEATURE:
<221> NAME/KEY: VARIANT
<222> LOCATION: (9)..(9)
<223> OTHER INFORMATION: /replace="Gly"
<220> FEATURE:
<221> NAME/KEY: misc_feature
<222> LOCATION: (8)..(9)
<223> OTHER INFORMATION: /note="Residues given in the sequence have no
      preference with respect to those in the annotations for said
      positions"
<220> FEATURE:
<221> NAME/KEY: VARIANT
<222> LOCATION: (11)..(11)
<223> OTHER INFORMATION: /replace="Asp"
<220> FEATURE:
<221> NAME/KEY: misc_feature
<222> LOCATION: (11)..(11)
<223> OTHER INFORMATION: /note="Residue given in the sequence has no
      preference with respect to that in the annotation for said
      position"
<220> FEATURE:
```

```
<221> NAME/KEY: VARIANT
<222> LOCATION: (13)..(13)
<223> OTHER INFORMATION: /replace="Arg"
<220> FEATURE:
<221> NAME/KEY: misc_feature
<222> LOCATION: (13)..(13)
<223> OTHER INFORMATION: /note="Residue given in the sequence has no
      preference with respect to that in the annotation for said
      position"
<220> FEATURE:
<221> NAME/KEY: VARIANT
<222> LOCATION: (15)..(15)
<223> OTHER INFORMATION: /replace="Tyr"
<220> FEATURE:
<221> NAME/KEY: misc_feature
<222> LOCATION: (15)..(15)
<223> OTHER INFORMATION: /note="Residue given in the sequence has no
      preference with respect to that in the annotation for said
      position"

<400> SEQUENCE: 68

Lys Ser Ser Gln Ser Leu Leu Trp Ser Ser Asn Gln Lys Asn His Leu
1               5                   10                  15

Ala

<210> SEQ ID NO 69
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus peptide"
<220> FEATURE:
<221> NAME/KEY: VARIANT
<222> LOCATION: (1)..(1)
<223> OTHER INFORMATION: /replace="Met"
<220> FEATURE:
<221> NAME/KEY: misc_feature
<222> LOCATION: (1)..(1)
<223> OTHER INFORMATION: /note="Residue given in the sequence has no
      preference with respect to that in the annotation for said
      position"

<400> SEQUENCE: 69

Leu Gln Gly Thr His Phe Pro Tyr Thr
1               5

<210> SEQ ID NO 70
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus peptide"
<220> FEATURE:
<221> NAME/KEY: VARIANT
<222> LOCATION: (12)..(12)
<223> OTHER INFORMATION: /replace="Glu"
<220> FEATURE:
<221> NAME/KEY: misc_feature
<222> LOCATION: (12)..(12)
<223> OTHER INFORMATION: /note="Residue given in the sequence has no
      preference with respect to that in the annotation for said
      position"

<400> SEQUENCE: 70

Lys Ser Ser Gln Ser Leu Leu Tyr Ser Asn Gly Lys Thr Tyr Leu Asn
1               5                   10                  15

<210> SEQ ID NO 71
```

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="C-term biotin"

<400> SEQUENCE: 71

Arg Pro Pro Gly Phe Ser Pro Phe Arg
1               5

<210> SEQ ID NO 72
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term KLH"

<400> SEQUENCE: 72

Arg Pro Pro Gly Phe Ser Pro Phe Arg
1               5

<210> SEQ ID NO 73
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="C-term KLH"

<400> SEQUENCE: 73

Arg Pro Pro Gly Phe Ser Pro Phe Arg
1               5

<210> SEQ ID NO 74
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term biotin"

<400> SEQUENCE: 74

Lys Arg Pro Pro Gly Phe Ser Pro Phe Arg
1               5                   10

<210> SEQ ID NO 75
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: source
<223> OTHER INFORMATION: /note="C-term biotin"

<400> SEQUENCE: 75

Lys Arg Pro Pro Gly Phe Ser Pro Phe Arg
1               5                   10

<210> SEQ ID NO 76
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term KLH"

<400> SEQUENCE: 76

Lys Arg Pro Pro Gly Phe Ser Pro Phe Arg
1               5                   10

<210> SEQ ID NO 77
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="C-term KLH"

<400> SEQUENCE: 77

Lys Arg Pro Pro Gly Phe Ser Pro Phe Arg
1               5                   10

<210> SEQ ID NO 78
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term biotin"

<400> SEQUENCE: 78

Arg Pro Pro Gly Phe Ser Pro Phe
1               5

<210> SEQ ID NO 79
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="C-term biotin"

<400> SEQUENCE: 79

Arg Pro Pro Gly Phe Ser Pro Phe
```

-continued

<210> SEQ ID NO 80
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
<220> FEATURE:
<221> NAME/KEY: source
<223> OTHER INFORMATION: /note="N-term KLH"

<400> SEQUENCE: 80

Arg Pro Pro Gly Phe Ser Pro Phe
1               5

<210> SEQ ID NO 81
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
<220> FEATURE:
<221> NAME/KEY: source
<223> OTHER INFORMATION: /note="C-term KLH"

<400> SEQUENCE: 81

Arg Pro Pro Gly Phe Ser Pro Phe
1               5

<210> SEQ ID NO 82
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
<220> FEATURE:
<221> NAME/KEY: source
<223> OTHER INFORMATION: /note="N-term biotin"

<400> SEQUENCE: 82

Lys Arg Pro Pro Gly Phe Ser Pro Phe
1               5

<210> SEQ ID NO 83
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
<220> FEATURE:
<221> NAME/KEY: source
<223> OTHER INFORMATION: /note="C-term biotin"

<400> SEQUENCE: 83

Lys Arg Pro Pro Gly Phe Ser Pro Phe
1               5

<210> SEQ ID NO 84
<211> LENGTH: 9
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term KLH"

<400> SEQUENCE: 84

Lys Arg Pro Pro Gly Phe Ser Pro Phe
1               5

<210> SEQ ID NO 85
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="C-term KLH"

<400> SEQUENCE: 85

Lys Arg Pro Pro Gly Phe Ser Pro Phe
1               5

<210> SEQ ID NO 86
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term biotin"

<400> SEQUENCE: 86

Arg Arg Pro Pro Gly Phe Ser Pro Phe Arg
1               5                   10

<210> SEQ ID NO 87
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="C-term biotin"

<400> SEQUENCE: 87

Arg Arg Pro Pro Gly Phe Ser Pro Phe Arg
1               5                   10

<210> SEQ ID NO 88
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term KLH"
```

<400> SEQUENCE: 88

Arg Arg Pro Pro Gly Phe Ser Pro Phe Arg
1               5                   10

<210> SEQ ID NO 89
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="C-term KLH"

<400> SEQUENCE: 89

Arg Arg Pro Pro Gly Phe Ser Pro Phe Arg
1               5                   10

<210> SEQ ID NO 90
<211> LENGTH: 9
<212> TYPE: PRT
<213> ORGANISM: Mus musculus

<400> SEQUENCE: 90

Arg Arg Pro Pro Gly Phe Ser Pro Phe
1               5

<210> SEQ ID NO 91
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term biotin"

<400> SEQUENCE: 91

Arg Arg Pro Pro Gly Phe Ser Pro Phe
1               5

<210> SEQ ID NO 92
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="C-term biotin"

<400> SEQUENCE: 92

Arg Arg Pro Pro Gly Phe Ser Pro Phe
1               5

<210> SEQ ID NO 93
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:

```
        Synthetic peptide"
<220> FEATURE:
<221> NAME/KEY: source
<223> OTHER INFORMATION: /note="N-term KLH"

<400> SEQUENCE: 93

Arg Arg Pro Pro Gly Phe Ser Pro Phe
1               5

<210> SEQ ID NO 94
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: source
<223> OTHER INFORMATION: /note="C-term KLH"

<400> SEQUENCE: 94

Arg Arg Pro Pro Gly Phe Ser Pro Phe
1               5

<210> SEQ ID NO 95
<211> LENGTH: 5
<212> TYPE: PRT
<213> ORGANISM: Unknown
<220> FEATURE:
<221> NAME/KEY: source
<223> OTHER INFORMATION: /note="Description of Unknown: Bradykinin 1-5
        peptide"

<400> SEQUENCE: 95

Arg Pro Pro Gly Phe
1               5

<210> SEQ ID NO 96
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: source
<223> OTHER INFORMATION: /note="N-term biotin"

<400> SEQUENCE: 96

Arg Pro Pro Gly Phe
1               5

<210> SEQ ID NO 97
<211> LENGTH: 136
<212> TYPE: PRT
<213> ORGANISM: Mus musculus

<400> SEQUENCE: 97

Leu Pro Glu Phe Gln Val Lys Leu Glu Glu Ser Gly Ala Glu Leu Val
1               5                   10                  15

Arg Ser Gly Ala Ser Val Lys Leu Ser Cys Thr Ala Ser Gly Phe Asn
            20                  25                  30

Ile Lys Asp Tyr Tyr Leu His Trp Val Lys Gln Arg Pro Glu Gln Gly
        35                  40                  45

Leu Glu Trp Ile Gly Trp Ile Asp Pro Glu Asn Gly Asp Thr Gly Tyr
```

```
                        50                  55                  60
Ala Arg Lys Phe Gln Gly Lys Ala Thr Met Thr Ala Asp Thr Ser Ser
 65                  70                  75                  80

Asn Thr Val Tyr Leu His Leu Ser Ser Leu Thr Ser Glu Asp Thr Ala
                 85                  90                  95

Val Tyr Tyr Phe Asn Ala Trp Glu Tyr Asp Gly Tyr Tyr Asp Leu Asp
                100                 105                 110

Tyr Trp Gly Gln Gly Thr Ser Val Thr Val Ser Ser Ala Lys Thr Thr
            115                 120                 125

Pro Pro Ser Val Tyr Gly Ser Ser
            130                 135

<210> SEQ ID NO 98
<211> LENGTH: 134
<212> TYPE: PRT
<213> ORGANISM: Mus musculus

<400> SEQUENCE: 98

Leu Pro Glu Phe Gln Val Gln Leu Glu Glu Ser Gly Gly Gly Leu Val
  1               5                  10                  15

Gln Pro Gly Gly Ser Met Lys Leu Ser Cys Val Ala Ser Gly Phe Thr
             20                  25                  30

Phe Ser Asn Tyr Trp Met Asn Trp Val Arg Gln Ser Pro Glu Lys Gly
         35                  40                  45

Leu Glu Trp Val Ala Glu Ile Arg Ser Lys Ser Asn Asn Tyr Ala Thr
     50                  55                  60

His Tyr Ala Glu Ser Val Lys Gly Arg Phe Thr Ile Ser Arg Asp Asp
 65                  70                  75                  80

Ser Lys Ser Ser Val Tyr Leu Gln Met Asn Asn Leu Arg Ala Glu Asp
                 85                  90                  95

Thr Gly Ile Tyr Tyr Cys Ile Gly Glu Asp Tyr Gly Gly Asp Tyr Trp
            100                 105                 110

Gly Gln Gly Thr Ser Val Thr Val Ser Ser Ala Lys Thr Thr Pro Pro
        115                 120                 125

Ser Val Tyr Gly Ser Ser
            130

<210> SEQ ID NO 99
<211> LENGTH: 136
<212> TYPE: PRT
<213> ORGANISM: Mus musculus

<400> SEQUENCE: 99

Leu Pro Glu Phe Glu Val Gln Leu Glu Glu Ser Gly Pro Glu Leu Val
  1               5                  10                  15

Lys Pro Gly Thr Ser Val Lys Val Ser Cys Lys Ala Ser Gly Tyr Ser
             20                  25                  30

Phe Thr Asp Tyr Asn Ile Tyr Trp Val Lys Gln Ser His Gly Lys Ser
         35                  40                  45

Leu Glu Trp Ile Gly Tyr Phe Asp Pro Tyr Asn Gly Asn Thr Gly Tyr
     50                  55                  60

Asn Gln Lys Phe Arg Gly Lys Ala Thr Leu Thr Val Asp Lys Ser Ser
 65                  70                  75                  80

Ser Thr Ala Phe Met His Leu Ser Ser Leu Thr Ser Asp Asp Ser Ala
                 85                  90                  95

Val Tyr Tyr Cys Ala Asn Tyr Tyr Arg Tyr Asp Asp His Ala Met Asp
```

```
            100                 105                 110
Tyr Trp Gly Gln Gly Thr Ser Val Thr Val Ser Ser Ala Lys Thr Thr
        115                 120                 125

Pro Pro Ser Val Tyr Gly Ser Ser
    130                 135

<210> SEQ ID NO 100
<211> LENGTH: 137
<212> TYPE: PRT
<213> ORGANISM: Mus musculus

<400> SEQUENCE: 100

Leu Pro Glu Phe Glu Val Lys Leu Gln Glu Ser Gly Ala Glu Leu Val
1               5                   10                  15

Arg Ser Gly Ala Ser Val Lys Leu Ser Cys Thr Ala Ser Gly Phe Asn
            20                  25                  30

Ile Lys Asp Tyr Tyr Met His Trp Val Lys Gln Arg Pro Glu Gln Gly
        35                  40                  45

Leu Glu Trp Ile Gly Trp Val Asp Pro Glu Asn Gly Asp Ser Asp Tyr
    50                  55                  60

Ala Pro Lys Phe Gln Gly Lys Ala Thr Met Thr Ala Asp Thr Ser Ser
65                  70                  75                  80

Asn Thr Val Tyr Leu Gln Phe Ser Ser Leu Thr Ser Glu Asp Thr Ala
                85                  90                  95

Val Tyr Tyr Cys Asn Ala Phe Glu Tyr Asp Gly Asn Tyr Ser Ser Leu
            100                 105                 110

Asp Phe Trp Gly Gln Gly Thr Ser Val Thr Val Ser Ser Ala Lys Thr
        115                 120                 125

Thr Pro Pro Ser Val Tyr Gly Ser Ser
    130                 135

<210> SEQ ID NO 101
<211> LENGTH: 137
<212> TYPE: PRT
<213> ORGANISM: Mus musculus

<400> SEQUENCE: 101

Leu Pro Glu Phe Glu Val Lys Leu Gln Gln Ser Gly Ala Glu Leu Val
1               5                   10                  15

Arg Ser Gly Ala Ser Val Lys Leu Ser Cys Thr Ala Ser Gly Phe Asn
            20                  25                  30

Ile Lys Asp Tyr Tyr Met His Trp Val Lys Gln Arg Pro Glu Gln Gly
        35                  40                  45

Leu Glu Trp Ile Gly Trp Val Asp Pro Glu Asn Gly Asp Ser Asp Tyr
    50                  55                  60

Ala Pro Lys Phe Gln Gly Lys Ala Thr Met Thr Ala Asp Thr Ser Ser
65                  70                  75                  80

Asn Thr Val Tyr Leu Gln Phe Ser Ser Leu Thr Ser Glu Asp Thr Ala
                85                  90                  95

Val Tyr Tyr Cys Asn Ala Phe Glu Tyr Asp Gly Asn Tyr Ser Pro Leu
            100                 105                 110

Asp Phe Trp Gly Gln Gly Thr Ser Val Thr Val Ser Ser Ala Lys Thr
        115                 120                 125

Thr Pro Pro Ser Val Tyr Gly Ser Ser
    130                 135
```

```
<210> SEQ ID NO 102
<211> LENGTH: 133
<212> TYPE: PRT
<213> ORGANISM: Mus musculus

<400> SEQUENCE: 102

Glu Leu Asp Ile Val Met Thr Gln Thr Thr Leu Thr Leu Ser Val Thr
1               5                   10                  15

Ile Gly Gln Pro Ala Ser Ile Ser Cys Lys Ser Ser Gln Ser Leu Leu
            20                  25                  30

Tyr Ser Asn Gly Lys Thr Tyr Leu Asn Trp Leu Leu Gln Arg Pro Gly
        35                  40                  45

Gln Ser Pro Lys Arg Leu Ile Tyr Leu Val Ser Lys Leu Asp Ser Gly
    50                  55                  60

Val Pro Asp Arg Phe Thr Gly Ser Gly Ser Gly Thr Asp Phe Thr Leu
65                  70                  75                  80

Lys Ile Ile Arg Val Glu Ala Glu Asp Leu Gly Val Tyr Tyr Cys Leu
                85                  90                  95

Gln Gly Thr His Phe Pro Tyr Thr Phe Gly Gly Gly Thr Lys Leu Glu
            100                 105                 110

Ile Lys Arg Ala Asp Ala Ala Pro Thr Val Ser Ile Phe Pro Pro Ser
        115                 120                 125

Lys Leu Glu Leu Tyr
    130

<210> SEQ ID NO 103
<211> LENGTH: 134
<212> TYPE: PRT
<213> ORGANISM: Mus musculus

<400> SEQUENCE: 103

Glu Leu Asp Ile Val Leu Thr Gln Ser Pro Ser Ser Leu Ala Val Ser
1               5                   10                  15

Val Gly Glu Lys Val Thr Met Ser Cys Lys Ser Ser Gln Ser Leu Leu
            20                  25                  30

Tyr Ser Ser Asp Gln Arg Asn Tyr Leu Ala Trp Tyr Gln Gln Arg Ser
        35                  40                  45

Gly Gln Ser Pro Lys Leu Leu Ile Tyr Trp Ala Ser Thr Arg Glu Ser
    50                  55                  60

Gly Val Pro Asp Arg Phe Thr Gly Ser Gly Ser Gly Thr Asp Phe Thr
65                  70                  75                  80

Leu Thr Ile Ser Ser Val Lys Ala Glu Asp Leu Ala Val Tyr Tyr Cys
                85                  90                  95

Gln Gln Tyr Tyr Ser Tyr Pro Tyr Thr Phe Gly Gly Gly Thr Lys Leu
            100                 105                 110

Glu Ile Lys Arg Ala Asp Ala Ala Pro Thr Val Ser Ile Phe Pro Pro
        115                 120                 125

Ser Lys Leu Glu Leu Tyr
    130

<210> SEQ ID NO 104
<211> LENGTH: 134
<212> TYPE: PRT
<213> ORGANISM: Mus musculus

<400> SEQUENCE: 104

Glu Leu Asp Ile Val Met Thr Gln Thr Pro Ser Ser Leu Ala Val Ser
1               5                   10                  15
```

-continued

Val Gly Glu Lys Val Thr Met Ser Cys Lys Ser Ser Gln Ser Leu Leu
            20                  25                  30

Tyr Thr Ser Asn Gln Lys Asn Tyr Leu Ala Trp Tyr Gln Gln Lys Pro
        35                  40                  45

Gly Gln Ser Pro Lys Pro Leu Ile Tyr Trp Ala Ser Thr Arg Glu Ser
    50                  55                  60

Gly Val Pro Asp Arg Phe Thr Gly Ser Gly Ser Gly Thr Asp Phe Thr
65                  70                  75                  80

Leu Thr Ile Ser Ser Val Lys Ala Glu Asp Leu Ala Ile Tyr Tyr Cys
                85                  90                  95

Gln Gln Tyr Tyr Ser Tyr Pro Trp Thr Phe Gly Gly Gly Thr Lys Leu
            100                 105                 110

Glu Ile Lys Arg Ala Asp Ala Ala Pro Thr Val Ser Ile Phe Pro Pro
        115                 120                 125

Ser Lys Leu Glu Leu Tyr
    130

<210> SEQ ID NO 105
<211> LENGTH: 133
<212> TYPE: PRT
<213> ORGANISM: Mus musculus

<400> SEQUENCE: 105

Glu Leu Asp Ile Val Ile Thr Gln Thr Thr Leu Ser Leu Ser Val Pro
1               5                   10                  15

Ile Gly Gln Pro Ala Ser Ile Ser Cys Lys Ser Arg Gln Ser Leu Leu
            20                  25                  30

Tyr Ser Asn Gly Glu Thr Tyr Leu Asn Trp Leu Leu Gln Arg Pro Gly
        35                  40                  45

Gln Ser Pro Lys Arg Leu Ile Tyr Leu Val Ser Lys Leu Asp Ser Gly
    50                  55                  60

Val Pro Asp Arg Phe Thr Gly Ser Arg Ser Gly Thr Asp Phe Thr Leu
65                  70                  75                  80

Lys Ile Ser Arg Val Glu Ser Glu Asp Leu Gly Val Tyr Tyr Cys Met
                85                  90                  95

Gln Gly Thr His Phe Pro Tyr Thr Phe Gly Gly Gly Thr Lys Leu Glu
            100                 105                 110

Ile Lys Arg Ala Asp Ala Ala Pro Thr Val Ser Ile Phe Pro Pro Ser
        115                 120                 125

Lys Leu Glu Leu Tyr
    130

<210> SEQ ID NO 106
<211> LENGTH: 133
<212> TYPE: PRT
<213> ORGANISM: Mus musculus

<400> SEQUENCE: 106

Glu Leu Asp Ile Val Ile Thr Gln Ser Thr Leu Thr Leu Ser Val Pro
1               5                   10                  15

Ile Gly Gln Pro Ala Ser Ile Ser Cys Lys Ser Ser Gln Ser Leu Leu
            20                  25                  30

Tyr Ser Asn Gly Glu Thr Tyr Leu Asn Trp Leu Leu Gln Arg Pro Gly
        35                  40                  45

Gln Ser Pro Lys Arg Gln Ile Tyr Leu Val Ser Lys Leu Asp Ser Gly
    50                  55                  60

```
Val Pro Asp Arg Phe Thr Gly Ser Arg Ser Gly Thr Asp Phe Thr Leu
 65                  70                  75                  80

Lys Ile Ser Arg Val Glu Ser Glu Asp Leu Gly Val Tyr Tyr Cys Met
                 85                  90                  95

Gln Gly Thr His Phe Pro Tyr Thr Phe Gly Gly Gly Thr Lys Leu Glu
            100                 105                 110

Ile Lys Arg Ala Asp Ala Ala Pro Thr Val Ser Ile Phe Pro Pro Ser
        115                 120                 125

Lys Leu Glu Leu Tyr
    130
```

```
<210> SEQ ID NO 107
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
aaaagcaggc ttaggagcgg ccgccatggc gtcccaggcc tcgctg            46

<210> SEQ ID NO 108
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
caagaaagct gggtcggatc cttataaagt tcccagaacc ctggtc            46

<210> SEQ ID NO 109
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
gcatacccat acgacgtccc agactacgct                              30

<210> SEQ ID NO 110
<211> LENGTH: 1005
<212> TYPE: DNA
<213> ORGANISM: Mus musculus

<400> SEQUENCE: 110
atggcgtccc aggcctcgct gaagctacag ccttctaacc aaagccagca ggcccctccc     60
aacatcacct cctgcgaggg cgccccggaa gcctgggatc tgctgtgtcg ggtgctgcca    120
gggtttgtca tcactgtctg tttctttggc ctcctgggga accttttagt cctgtccttc    180 ttcctttgc cttggcgacg atggtggcag cagcggcggc agcgcctaac catagcagaa    240
atctacctgg ctaacttggc agcttctgat ctggtgtttg tgctgggcct gcccttctgg    300
gcagagaacg ttgggaaccg tttcaactgg cccttggaa gtgacctctg ccgggtggtc    360
agcggggtca tcaaggccaa cctgttcatc agcatcttcc tggtggtggc catcagtcag    420
```

```
gaccgctaca ggttgctggt atacccatg accagctggg ggaaccggcg gcgacggcaa      480
gcccaagtga cctgcctgct catctgggta gctgggggcc tcttgagcac ccccacgttc      540
cttctgcgtt ccgtcaaagt cgtccctgat ctgaacatct ctgcctgcat cctgcttttc      600
ccccacgaag cttggcactt tgtaaggatg gtggagttga acgttttggg tttcctcctc      660
ccattggctg ccatcctcta cttcaacttt cacatcctgg cctccctgag aggacagaag      720
gaggccagca gaacccggtg tgggggaccc aaggacagca agacaatggg gctgatcctc      780
acactggtag cctccttcct ggtctgctgg gccccttacc acttctttgc cttcctggat      840
ttcctggtcc aggtgagagt gatccaggac tgcttctgga aggagctcac agacctgggc      900
ctgcagctgg ccaacttctt tgcttttgtc aacagctgcc tgaacccact gatttatgtc      960
tttgcaggcc ggctctttaa gaccagggtt ctgggaactt tataa                    1005
```

<210> SEQ ID NO 111
<211> LENGTH: 111
<212> TYPE: PRT
<213> ORGANISM: Mus musculus

<400> SEQUENCE: 111

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Pro Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Ile Tyr Tyr Cys Gln Gln
                85                  90                  95

Tyr Tyr Ser Tyr Pro Trp Thr Phe Gly Gly Gly Thr Lys Leu Glu
            100                 105                 110
```

<210> SEQ ID NO 112
<211> LENGTH: 105
<212> TYPE: PRT
<213> ORGANISM: Homo sapiens

<400> SEQUENCE: 112

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Ser Tyr Ser Thr Pro Pro
                85                  90                  95

Thr Phe Gly Gln Gly Thr Lys Val Glu
            100                 105
```

-continued

<210> SEQ ID NO 113
<211> LENGTH: 120
<212> TYPE: PRT
<213> ORGANISM: Mus musculus

<400> SEQUENCE: 113

Glu Ile Gln Leu Gln Gln Ser Gly Pro Glu Leu Val Lys Pro Gly Thr
1               5                   10                  15

Ser Val Lys Val Ser Cys Lys Ala Ser Gly Tyr Ser Phe Thr Asp Tyr
            20                  25                  30

Asn Ile Tyr Trp Val Lys Gln Ser His Gly Lys Ser Leu Glu Trp Ile
        35                  40                  45

Gly Tyr Phe Asp Pro Tyr Asn Gly Asn Thr Gly Tyr Asn Gln Lys Phe
    50                  55                  60

Arg Gly Lys Ala Thr Leu Thr Val Asp Lys Ser Ser Thr Ala Phe
65                  70                  75                  80

Met His Leu Ser Ser Leu Thr Ser Asp Asp Ser Ala Val Tyr Tyr Cys
                85                  90                  95

Ala Asn Tyr Tyr Arg Tyr Asp Asp His Ala Met Asp Tyr Trp Gly Gln
            100                 105                 110

Gly Thr Ser Val Thr Val Ser Ser
        115                 120

<210> SEQ ID NO 114
<211> LENGTH: 123
<212> TYPE: PRT
<213> ORGANISM: Homo sapiens

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Tyr Asp Tyr Asp Val Phe Tyr Tyr Ala Met Asp Tyr
            100                 105                 110

Trp Gly Gln Gly Thr Leu Val Thr Val Ser Ser
        115                 120

<210> SEQ ID NO 115
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Asp Ile Val Met Thr Gln Ser Pro Asp Ser Leu Ala Val Ser Leu Gly
1               5                   10                  15

```
Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys

<210> SEQ ID NO 116
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Glu Tyr Ser Ser Ser Asp Ala Phe Asp Ile Trp Gly Gln
            100                 105                 110

Gly Thr Met Val Thr Val Ser Ser
        115                 120

<210> SEQ ID NO 117
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term biotin"

<400> SEQUENCE: 117

Arg Pro Pro Gly Phe Ser Pro Phe Arg
 1               5

<210> SEQ ID NO 118
<211> LENGTH: 127
<212> TYPE: PRT
<213> ORGANISM: Mus musculus
```

<400> SEQUENCE: 118

```
Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile
        35                  40                  45

Gly Trp Ile Asp Pro Glu Asn Gly Asp Thr Gly Tyr Ala Arg Lys Phe
    50                  55                  60

Gln Gly Lys Ala Thr Met Thr Ala Asp Thr Ser Ser Asn Thr Val Tyr
65                  70                  75                  80

Leu His Leu Ser Ser Leu Thr Ser Glu Asp Thr Ala Val Tyr Tyr Phe
                85                  90                  95

Asn Ala Trp Glu Tyr Asp Gly Tyr Tyr Asp Leu Asp Tyr Trp Gly Gln
            100                 105                 110

Gly Thr Ser Val Thr Val Ser Ser Ala Lys Thr Thr Pro Pro Ser
        115                 120                 125
```

<210> SEQ ID NO 119
<211> LENGTH: 125
<212> TYPE: PRT
<213> ORGANISM: Mus musculus

<400> SEQUENCE: 119

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Ser Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ile Gly Glu Asp Tyr Gly Gly Asp Tyr Trp Gly Gln Gly Thr
            100                 105                 110

Ser Val Thr Val Ser Ser Ala Lys Thr Thr Pro Pro Ser
        115                 120                 125
```

<210> SEQ ID NO 120
<211> LENGTH: 127
<212> TYPE: PRT
<213> ORGANISM: Mus musculus

<400> SEQUENCE: 120

```
Glu Ile Gln Leu Gln Gln Ser Gly Pro Glu Leu Val Lys Pro Gly Thr
1               5                   10                  15

Ser Val Lys Val Ser Cys Lys Ala Ser Gly Tyr Ser Phe Thr Asp Tyr
            20                  25                  30

Asn Ile Tyr Trp Val Lys Gln Ser His Gly Lys Ser Leu Glu Trp Ile
        35                  40                  45

Gly Tyr Phe Asp Pro Tyr Asn Gly Asn Thr Gly Tyr Asn Gln Lys Phe
    50                  55                  60
```

Arg Gly Lys Ala Thr Leu Thr Val Asp Lys Ser Ser Thr Ala Phe
65                  70                  75                  80

Met His Leu Ser Ser Leu Thr Ser Asp Asp Ser Ala Val Tyr Tyr Cys
                85                  90                  95

Ala Asn Tyr Tyr Arg Tyr Asp Asp His Ala Met Asp Tyr Trp Gly Gln
            100                 105                 110

Gly Thr Ser Val Thr Val Ser Ser Ala Lys Thr Thr Pro Pro Ser
            115                 120                 125

<210> SEQ ID NO 121
<211> LENGTH: 128
<212> TYPE: PRT
<213> ORGANISM: Mus musculus

<400> SEQUENCE: 121

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Val Asp Pro Glu Asn Gly Asp Ser Asp Tyr Ala Pro Lys Phe
    50                  55                  60

Gln Gly Lys Ala Thr Met Thr Ala Asp Thr Ser Ser Asn Thr Val Tyr
65                  70                  75                  80

Leu Gln Phe Ser Ser Leu Thr Ser Glu Asp Thr Ala Val Tyr Tyr Cys
                85                  90                  95

Asn Ala Phe Glu Tyr Asp Gly Asn Tyr Ser Pro Leu Asp Phe Trp Gly
            100                 105                 110

Gln Gly Thr Ser Val Thr Val Ser Ser Ala Lys Thr Thr Pro Pro Ser
            115                 120                 125

<210> SEQ ID NO 122
<211> LENGTH: 128
<212> TYPE: PRT
<213> ORGANISM: Mus musculus

<400> SEQUENCE: 122

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Val Asp Pro Glu Asn Gly Asp Ser Asp Tyr Ala Pro Lys Phe
    50                  55                  60

Gln Gly Lys Ala Thr Met Thr Ala Asp Thr Ser Ser Asn Thr Val Tyr
65                  70                  75                  80

Leu Gln Phe Ser Ser Leu Thr Ser Glu Asp Thr Ala Val Tyr Tyr Cys
                85                  90                  95

Asn Ala Phe Glu Tyr Asp Gly Asn Tyr Ser Pro Leu Asp Phe Trp Gly
            100                 105                 110

Gln Gly Thr Ser Val Thr Val Ser Ser Ala Lys Thr Thr Pro Pro Ser
            115                 120                 125

<210> SEQ ID NO 123
<211> LENGTH: 119

```
<212> TYPE: PRT
<213> ORGANISM: Mus musculus

<400> SEQUENCE: 123

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ile Arg Val Glu Ala Glu Asp Leu Gly Val Tyr Tyr Cys Leu Gln Gly
                85                  90                  95

Thr His Phe Pro Tyr Thr Phe Gly Gly Gly Thr Lys Leu Glu Ile Lys
            100                 105                 110

Arg Ala Asp Ala Ala Pro Thr
            115

<210> SEQ ID NO 124
<211> LENGTH: 120
<212> TYPE: PRT
<213> ORGANISM: Mus musculus

<400> SEQUENCE: 124

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asp Gln Arg Asn Tyr Leu Ala Trp Tyr Gln Gln Arg Ser Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys Arg Ala Asp Ala Ala Pro Thr
            115                 120

<210> SEQ ID NO 125
<211> LENGTH: 120
<212> TYPE: PRT
<213> ORGANISM: Mus musculus

<400> SEQUENCE: 125

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Pro Leu Ile Tyr Trp Ala Ser Thr Arg Glu Ser Gly Val
```

```
                    50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Ile Tyr Tyr Cys Gln Gln
                     85                  90                  95

Tyr Tyr Ser Tyr Pro Trp Thr Phe Gly Gly Gly Thr Lys Leu Glu Ile
                    100                 105                 110

Lys Arg Ala Asp Ala Ala Pro Thr
            115                 120

<210> SEQ ID NO 126
<211> LENGTH: 120
<212> TYPE: PRT
<213> ORGANISM: Mus musculus

<400> SEQUENCE: 126

Asp Ile Val Met Thr Gln Ser Pro Ser Ser Leu Ser Val Ser Ala Gly
 1               5                  10                  15

Glu Lys Val Thr Met Ser Cys Lys Ser Ser Gln Ser Leu Leu Asn Ser
                 20                  25                  30

Gly Asn Gln Lys Asn Tyr Leu Ala Trp Tyr Gln Lys Pro Gly Gln
             35                  40                  45

Pro Pro Lys Leu Leu Ile Tyr Gly Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                     85                  90                  95

Asp His Ser Tyr Pro Leu Thr Phe Gly Ala Gly Thr Lys Leu Glu Leu
                    100                 105                 110

Lys Arg Ala Asp Ala Ala Pro Thr
            115                 120

<210> SEQ ID NO 127
<211> LENGTH: 360
<212> TYPE: DNA
<213> ORGANISM: Mus musculus

<400> SEQUENCE: 127
gagatccagc tgcagcagtc tggacctgag ctggtgaagc ctgggacttc agtgaaggtg      60
tcctgcaagg cttctggtta ctcattcact gactacaaca tctactgggt gaaacagagc     120
catggaaaga gccttgagtg gattggatat tttgatcctt acaatggtaa tactggctac     180
aaccagaagt tcaggggcaa ggccacattg actgttgaca gtcctccag cacagccttc      240 atgcatctca gcagcctgac atctgatgac tctgcagtct attactgtgc aaactactat     300
aggtatgacg accatgctat ggactattgg ggtcaaggaa cctcagtcac cgtctcctca     360

<210> SEQ ID NO 128
<211> LENGTH: 339
<212> TYPE: DNA
<213> ORGANISM: Mus musculus

<400> SEQUENCE: 128
gacattgtga tgtcacagtc tccatcctcc ctagctgtgt cagttggaga gaaggttact      60
atgagctgca agtccagtca gagccttta tatagtagca tcaaaagaa ctacttggcc       120 tggtaccagc agaaaccagg gcagtctcct aaaccgctga tttactgggc atccactagg     180
```

```
gaatctgggg tccctgatcg cttcacaggc agtggatctg ggacagattt cactctcacc    240
atcagcagtg tgaaggctga agacctggca atttattact gtcagcaata ttatagctat    300
ccgtggacgt tcggtggagg caccaagctg gaaatcaaa                           339
```

<210> SEQ ID NO 129
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129

```
cagattcagc tggtgcagtc tggcgccgaa gtgaagaaac ctggcgccag cgtgaaggtg    60
tcctgcaagg ccagcggcta cagcttcacc gactacaaca tctactgggt ccgacaggct    120
ccaggccagg gactgaatg gatcggctac ttcgacccct acaacggcaa caccggctac    180
aaccagaagt tccggggcag agccaccctg accgtggaca gagcaccag caccgcctac    240 atggaactgc ggagcctgag aagcgacgac accgccgtgt actactgcgc caactactac    300
agatacgacg accacgccat ggactactgg ggccagggca ccctggtcac cgtgtcctct    360
```

<210> SEQ ID NO 130
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 130

```
gacatcgtga tgacccagag ccccgacagc ctggccgtgt ctctgggcga gcgggccacc    60
atcaactgca agagcagcca gagcctgctg tactctagca ccagaagaa ctacctggcc    120 tggtatcagc agaagcccgg ccagcccccc aagcccctga tctactgggc agcaccccgc    180
gagagcggcg tgcccgatag attttccggc agcggctccg gcaccgactt cacccctgacc   240 atcagcagcc tgcaggccga ggacgtggcc gtgtactact gccagcagta ctacagctac    300
ccctggacct tcggccaggg caccaaggtg gaaatcaag                           339
```

<210> SEQ ID NO 131
<211> LENGTH: 119
<212> TYPE: PRT
<213> ORGANISM: Mus musculus

<400> SEQUENCE: 131

```
Asp Val Val Met Thr Gln Thr Pro Leu Thr Leu Ser Val Pro Ile Gly
 1               5                  10                  15

Gln Pro Ala Ser Ile Ser Cys Lys Ser Ser Gln Ser Leu Leu Tyr Ser
             20                  25                  30

Asn Gly Glu Thr Tyr Leu Asn Trp Leu Leu Gln Arg Pro Gly Gln Ser
         35                  40                  45

Pro Lys Arg Leu Ile Tyr Leu Val Ser Lys Leu Asp Ser Gly Val Pro
     50                  55                  60

Asp Arg Phe Thr Gly Ser Arg Ser Gly Thr Asp Phe Thr Leu Lys Ile
 65                  70                  75                  80

Ser Arg Val Glu Ser Glu Asp Leu Gly Val Tyr Tyr Cys Met Gln Gly
```

```
                    85                  90                  95
Thr His Phe Pro Tyr Thr Phe Gly Gly Gly Thr Lys Leu Glu Ile Lys
                100                 105                 110
Arg Ala Asp Ala Ala Pro Thr
            115

<210> SEQ ID NO 132
<211> LENGTH: 4
<212> TYPE: PRT
<213> ORGANISM: Homo sapiens

<400> SEQUENCE: 132

Lys Arg Pro Pro
1

<210> SEQ ID NO 133
<211> LENGTH: 6
<212> TYPE: PRT
<213> ORGANISM: Homo sapiens

<400> SEQUENCE: 133

Arg Pro Pro Gly Phe Ser
1               5

<210> SEQ ID NO 134
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Pro Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Trp Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
```

```
            195                 200                 205
Ser Pro Val Thr Lys Ser Phe Asn Arg Gly Glu Cys
    210                 215                 220

<210> SEQ ID NO 135
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Gln Ile Gln Leu Val Gln Ser Gly Ala Glu Val Lys Pro Gly Ala
1               5                   10                  15

Ser Val Lys Val Ser Cys Lys Ala Ser Gly Tyr Ser Phe Thr Asp Tyr
            20                  25                  30

Asn Ile Tyr Trp Val Arg Gln Ala Pro Gly Gln Gly Leu Glu Trp Ile
        35                  40                  45

Gly Tyr Phe Asp Pro Tyr Asn Gly Asn Thr Gly Tyr Asn Gln Lys Phe
    50                  55                  60

Arg Gly Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Asn Tyr Tyr Arg Tyr Asp Asp His Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys His
    210                 215                 220

His His His His
225

<210> SEQ ID NO 136
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Ala Ser Thr Lys Gly Pro
1               5

<210> SEQ ID NO 137
```

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 137

His His His His His His
1               5
```

We claim:

1. An isolated nucleic acid encoding an amino acid sequence of an antibody, or antigen binding fragment thereof, comprising:
   i) a heavy chain variable domain comprising a heavy chain complementarity determining region 3 (HCDR3) amino acid sequence selected from the group consisting of:
      a) SEQ ID NO: 7 [$X_1$Y $X_2$ $X_3$D $X_4$HAM $X_5$Y], wherein
         $X_1$ is Y, F or H,
         $X_2$ is R, D, A, V, L, I, M, F, Y or W,
         $X_3$ is Y, F, W or H,
         $X_4$ is D, E or Y, and
         $X_5$ is D or E;
      b) SEQ ID NO: 63 [$X_1$EYDG$X_2$Y$X_3$$X_4$LD$X_5$], wherein
         $X_1$ is W or F,
         $X_2$ is N or no amino acid,
         $X_3$ is Y or S,
         $X_4$ is D or P, and
         $X_5$ is F or Y;
      c) SEQ ID NO: 13;
      d) SEQ ID NO: 32;
      e) SEQ ID NO: 40;
      f) SEQ ID NO: 47; and
      g) SEQ ID NO: 55;
   ii) a heavy chain variable domain comprising a heavy chain complementarity determining region 2 (HCDR2) amino acid sequence selected from the group consisting of:
      h) SEQ ID NO: 8 [YF$X_1$P$X_2$NGNTGYNQKFRG], wherein
         $X_1$ is D, R, A, V, L, I, M, F, Y or W, and
         $X_2$ is Y, D, E, N, or Q;
      i) SEQ ID NO: 64 [W$X_1$DPENGD$X_2$$X_3$YAPKFQG], wherein
         $X_1$ is I, or V,
         $X_2$ is T, or S, and
         $X_3$ is G, or D;
      j) SEQ ID NO: 14;
      k) SEQ ID NO: 33;
      l) SEQ ID NO: 41;
      m) SEQ ID NO: 48; and
      n) SEQ ID NO: 56;
   iii) a heavy chain variable domain comprising a heavy chain complementarity determining region 1 (HCDR1) amino acid sequence selected from the group consisting of:
      o) SEQ ID NO: 9 [GYSFTDY$X_1$IY], wherein $X_1$ is N, W or Y;
      p) SEQ ID NO: 65 [GFNIKDYY$X_1$H], wherein $X_1$ is L, or M;
      q) SEQ ID NO: 15;
      r) SEQ ID NO: 34;
      s) SEQ ID NO: 42;
      t) SEQ ID NO: 49; and
      u) SEQ ID NO: 57;
   iv) a light chain variable domain comprising a light chain complementarity determining region 3 (LCDR3) amino acid sequence selected from the group consisting of:
      v) SEQ ID NO: 10 [QQ $X_1$ $X_2$S $X_3$P $X_4$T], wherein
         $X_1$ is Y, F or H,
         $X_2$ is Y, F, H or W,
         $X_3$ is Y, F, T or H, and
         $X_4$ is W, Y, F, H or L;
      w) SEQ ID NO: 66 [Q$X_1$$X_2$$X_3$S$X_4$P$X_5$T], wherein
         $X_1$ is Q or N,
         $X_2$ is Y, F, D or H,
         $X_3$ is Y, F, H or W,
         $X_4$ is Y, F, T or H, and
         $X_5$ is W, Y, F, H or L;
      x) SEQ ID NO: 69 [$X_1$QGTHFPYT], wherein $X_1$ is L or M;
      y) SEQ ID NO: 16;
      z) SEQ ID NO: 35;
      aa) SEQ ID NO: 43;
      bb) SEQ ID NO: 50; and
      cc) SEQ ID NO: 58;
   v) a light chain variable domain comprising a light chain complementarity determining region 2 (LCDR2) amino acid sequence selected from the group consisting of:
      dd) SEQ ID NO: 11 [WASTR$X_1$], wherein $X_1$ is E, D, Q or N;
      ee) SEQ ID NO: 67 [$X_1$ASTR$X_2$], wherein
         $X_1$ is W or G, and
         $X_2$ is E, D, Q or N;
      ff) SEQ ID NO: 17;
      gg) SEQ ID NO: 36;
      hh) SEQ ID NO: 51; and
      ii) SEQ ID NO: 59;
   and
   vi) a light chain variable domain comprising a light chain complementarity determining region 1 (LCDR1) amino acid sequence selected from the group consisting of:
      jj) SEQ ID NO: 12 [KSSQSLL $X_1$SSNQKN $X_2$LA], wherein
         $X_1$ is W, H, Y or F, and
         $X_2$ is H or Y;
      kk) SEQ ID NO: 68 [KSSQSLL$X_1$$X_2$S$X_3$Q$X_4$N$X_5$LA], wherein
         $X_1$ is W, H, Y or F,
         $X_2$ is S or G,
         $X_3$ is N or D,
         $X_4$ is K or R,
         $X_5$ is H or Y; and
      ll) SEQ ID NO: 70 [KSSQSLLYSNG$X_1$TYLN], wherein
         $X_1$ is K or E;

mm) SEQ ID NO: 18;
nn) SEQ ID NO: 37;
oo) SEQ ID NO: 44;
pp) SEQ ID NO: 52; and
qq) SEQ ID NO: 60.

2. The isolated nucleic acid of claim 1, wherein:
the antibody or antigen binding fragment thereof comprises: a) a heavy chain variable domain comprising the consensus HCDR3, HCDR2 and HCDR1 region amino sequences set forth in SEQ ID NOs: 7, 8, and 9, respectively; and b) a light chain variable domain comprising the consensus LCDR3, LCDR2 and LCDR1 region amino sequences set forth in SEQ ID NOs: 10, 11, and 12, respectively; or
the antibody or antigen binding fragment thereof comprises: a) a heavy chain variable domain comprising the HCDR3, HCDR2 and HCDR1 region amino sequences set forth in SEQ ID NOs: 13, 14, and 15, respectively; and b) a light chain variable domain comprising the LCDR3, LCDR2 and LCDR1 region amino sequences set forth in SEQ ID NOs: 16, 17, and 18, respectively; or
the antibody or antigen binding fragment thereof comprises: a) a heavy chain variable domain comprising the HCDR3, HCDR2 and HCDR1 region amino sequences set forth in SEQ ID NOs: 32, 33, and 34, respectively; and b) a light chain variable domain comprising the LCDR3, LCDR2 and LCDR1 region amino sequences set forth in SEQ ID NOs: 35, 36, and 37, respectively; or
the antibody or antigen binding fragment thereof comprises: a) a heavy chain variable domain comprising the HCDR3, HCDR2 and HCDR1 region amino sequences set forth in SEQ ID NOs: 40, 41 and 42, respectively; and b) a light chain variable domain comprising the LCDR3, LCDR2 and LCDR1 region amino sequences set forth in SEQ ID NOs: 43, 17, and 44, respectively.

3. The isolated nucleic acid of claim 1, wherein the antibody or antigen binding fragment thereof comprises: a) a heavy chain variable domain comprising the HCDR3, HCDR2 and HCDR1 region amino sequences set forth in SEQ ID NOs: 47, 48, and 49, respectively; and b) a light chain variable domain comprising the LCDR3, LCDR2 and LCDR1 region amino sequences set forth in SEQ ID NOs: 50, 51, and 52, respectively.

4. The isolated nucleic acid of claim 1, wherein the antibody or antigen binding fragment thereof comprises: a) a heavy chain variable domain comprising the HCDR3, HCDR2 and HCDR1 region amino sequences set forth in SEQ ID NOs: 55, 56, and 57, respectively; and b) a light chain variable domain comprising the LCDR3, LCDR2 and LCDR1 region amino sequences set forth in SEQ ID NOs: 58, 59, and 60, respectively.

5. The isolated nucleic acid of claim 1, wherein the antibody or antigen binding fragment thereof comprises: a) a heavy chain variable domain comprising the HCDR3, HCDR2 and HCDR1 region amino sequences set forth in SEQ ID NOs: 13, 14, and 15, respectively, and one or more amino acid substitution at positions selected from the group consisting of H1, H5, H9, H11, H12, H16, H38, H40, H41, H43, H44, H66, H75, H79, H81, H82A, H83, H87, and H108, according to Kabat; and b) a light chain variable domain comprising the LCDR3, LCDR2 and LCDR1 region amino sequences set forth in SEQ ID NOs: 16, 17, and 18, respectively, and one or more amino acid substitution at positions selected from the group consisting of L5, L9, L15, L18, L19, L21, L22, L43, L63, L78, L79, L83, L85, L100 and L104, according to Kabat.

6. A recombinant expression vector comprising the nucleic acid of claim 1.

7. A host cell comprising the recombinant expression vector of claim 6.

8. A method of producing an antibody, or an antigen binding fragment thereof, that binds specifically to Kallidin and des-$Arg_{10}$-Kallidin, comprising culturing the host cell of claim 7 under conditions such that the antibody, or antigen binding fragment thereof, that binds specifically to Kallidin and des-$Arg_{10}$-Kallidin is produced by the host cell.

9. The method of claim 8, wherein the antibody or antigen binding fragment thereof comprises: a) a heavy chain variable domain comprising the consensus HCDR3, HCDR2 and HCDR1 region amino sequences set forth in SEQ ID NOs: 7, 8, and 9, respectively; and b) a light chain variable domain comprising the consensus LCDR3, LCDR2 and LCDR1 region amino sequences set forth in SEQ ID NOs: 10, 11, and 12, respectively.

10. The method of claim 8, wherein the antibody or antigen binding fragment thereof comprises: a) a heavy chain variable domain comprising the HCDR3, HCDR2 and HCDR1 region amino sequences set forth in SEQ ID NOs: 13, 14, and 15, respectively; and b) a light chain variable domain comprising the LCDR3, LCDR2 and LCDR1 region amino sequences set forth in SEQ ID NOs: 16, 17, and 18, respectively.

11. The method of claim 8, wherein the antibody or antigen binding fragment thereof comprises: a) a heavy chain variable domain comprising the HCDR3, HCDR2 and HCDR1 region amino sequences set forth in SEQ ID NOs: 32, 33, and 34, respectively; and b) a light chain variable domain comprising the LCDR3, LCDR2 and LCDR1 region amino sequences set forth in SEQ ID NOs: 35, 36, and 37, respectively.

12. The method of claim 8, wherein the antibody or antigen binding fragment thereof comprises: a) a heavy chain variable domain comprising the HCDR3, HCDR2 and HCDR1 region amino sequences set forth in SEQ ID NOs: 40, 41 and 42, respectively; and b) a light chain variable domain comprising the LCDR3, LCDR2 and LCDR1 region amino sequences set forth in SEQ ID NOs: 43, 17, and 44, respectively.

13. The method of claim 8, wherein the antibody or antigen binding fragment thereof comprises: a) a heavy chain variable domain comprising the HCDR3, HCDR2 and HCDR1 region amino sequences set forth in SEQ ID NOs: 47, 48, and 49, respectively; and b) a light chain variable domain comprising the LCDR3, LCDR2 and LCDR1 region amino sequences set forth in SEQ ID NOs: 50, 51, and 52, respectively.

14. The method of claim 8, wherein the antibody or antigen binding fragment thereof comprises: a) a heavy chain variable domain comprising the HCDR3, HCDR2 and HCDR1 region amino sequences set forth in SEQ ID NOs: 55, 56, and 57, respectively; and b) a light chain variable domain comprising the LCDR3, LCDR2 and LCDR1 region amino sequences set forth in SEQ ID NOs: 58, 59, and 60, respectively.

15. The method of claim 8, wherein the antibody or antigen binding fragment thereof comprises: a) a heavy chain variable domain comprising the HCDR3, HCDR2 and HCDR1 region amino sequences set forth in SEQ ID NOs: 13, 14, and 15, respectively, and one or more amino acid substitution at positions selected from the group consisting of H1, H5, H9, H11, H12, H16, H38, H40, H41, H43, H44, H66, H75, H79, H81, H82A, H83, H87, and H108, according to Kabat; and b) a light chain variable domain comprising the LCDR3, LCDR2 and LCDR1 region amino acid sequences set forth in SEQ ID NOs: 16, 17, and 18, respectively, and one or more amino acid substitution at positions selected from the group consisting of L5, L9, L15, L18, L19, L21, L22, L43, L63, L78, L79, L83, L85, L100 and L104, according to Kabat.

* * * * *